US012214020B2

(12) United States Patent
Sprogøe et al.

(10) Patent No.: US 12,214,020 B2
(45) Date of Patent: *Feb. 4, 2025

(54) PTH PRODRUGS

(71) Applicant: ASCENDIS PHARMA BONE DISEASES A/S, Hellerup (DK)

(72) Inventors: Kennett Sprogøe, Holte (DK); Felix Cleemann, Mainz (DE); Guillaume Maitro, Mannheim (DE); Mathias Krusch, Hirschhorn (DE); Thomas Wegge, Heidelberg (DE); Joachim Zettler, Heidelberg (DE)

(73) Assignee: ASCENDIS PHARMA BONE DISEASES A/S, Hellerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/464,046

(22) Filed: Sep. 8, 2023

(65) Prior Publication Data

US 2024/0123038 A1 Apr. 18, 2024

Related U.S. Application Data

(63) Continuation of application No. 18/053,693, filed on Nov. 8, 2022, now Pat. No. 11,793,861, which is a continuation of application No. 17/488,137, filed on Sep. 28, 2021, now abandoned, which is a continuation of application No. 16/118,155, filed as application No. PCT/EP2017/054550 on Feb. 28, 2017, now abandoned.

(30) Foreign Application Priority Data

| Mar. 1, 2016 | (EP) | 16158048 |
| Jul. 13, 2016 | (EP) | 16179294 |
| Sep. 29, 2016 | (EP) | 16191484 |
| Feb. 13, 2017 | (EP) | 17155839 |

(51) Int. Cl.
*A61K 38/29* (2006.01)
*A61K 9/00* (2006.01)
*A61K 47/54* (2017.01)
*A61K 47/60* (2017.01)

(52) U.S. Cl.
CPC ............ *A61K 38/29* (2013.01); *A61K 9/0019* (2013.01); *A61K 47/54* (2017.08); *A61K 47/545* (2017.08); *A61K 47/60* (2017.08)

(58) Field of Classification Search
CPC ...... A61K 38/29; A61K 47/54; A61K 47/545; A61K 47/60; A61K 9/0019; A61P 1/02; A61P 17/14; A61P 19/02; A61P 19/10; A61P 29/00; A61P 5/18; A61P 7/04; C07K 14/575
See application file for complete search history.

(56) References Cited

U.S. PATENT DOCUMENTS

| 5,567,439 | A | 10/1996 | Myers et al. |
| 5,744,444 | A | 4/1998 | Forssmann et al. |
| 7,585,837 | B2 | 9/2009 | Schechter et al. |
| 7,820,179 | B2 | 10/2010 | Brown-Augsburger et al. |
| 8,101,729 | B2 | 1/2012 | Niemczyk et al. |
| 8,618,124 | B2 | 12/2013 | Greenwald et al. |
| 8,754,190 | B2 | 6/2014 | Ashley et al. |
| 8,865,220 | B2 | 10/2014 | Ho et al. |
| 8,906,847 | B2 * | 12/2014 | Cleemann ............... A61K 38/26 514/1.3 |
| 8,946,405 | B2 | 2/2015 | Ashley et al. |
| 10,980,860 | B2 | 4/2021 | Vetter et al. |
| 11,590,207 | B2 | 2/2023 | Holten-Andersen et al. |
| 11,759,504 | B2 * | 9/2023 | Sprogøe .................. A61K 9/00 514/11.8 |
| 11,793,861 | B2 * | 10/2023 | Sprogøe .................. A61P 19/02 |
| 11,857,603 | B2 | 1/2024 | Sprogøe et al. |
| 11,890,326 | B2 * | 2/2024 | Sprogøe .................. A61K 47/54 |
| 2003/0166581 | A1 | 9/2003 | Almarsson et al. |
| 2005/0124537 | A1 | 6/2005 | Kostenuik et al. |
| 2005/0148763 | A1 | 7/2005 | Sekimori et al. |
| 2006/0045912 | A1 | 3/2006 | Truog |
| 2006/0069021 | A1 | 3/2006 | Costantino et al. |
| 2010/0129341 | A1 | 5/2010 | Sakon et al. |
| 2011/0112021 | A1 | 5/2011 | Rau et al. |
| 2011/0195900 | A1 | 8/2011 | Schteingart et al. |
| 2011/0229580 | A1 | 9/2011 | Srivastava et al. |
| 2011/0305766 | A1 | 12/2011 | Ho et al. |
| 2012/0035101 | A1 | 2/2012 | Fares et al. |
| 2012/0040320 | A1 | 2/2012 | Nadeau |
| 2012/0322721 | A1 * | 12/2012 | Rasmussen ............... A61K 9/19 514/1.3 |
| 2013/0116180 | A1 | 5/2013 | Gardella et al. |
| 2013/0183349 | A1 | 7/2013 | Ho et al. |
| 2014/0011739 | A1 | 1/2014 | Klatzmann et al. |

(Continued)

FOREIGN PATENT DOCUMENTS

| CN | 1597697 A | 3/2005 |
| CN | 1739795 A | 3/2006 |

(Continued)

OTHER PUBLICATIONS

U.S. Appl. No. 17/428,608, filed Aug. 4, 2021, Skands et al.
U.S. Appl. No. 17/488,137, filed Sep. 28, 2021, Sprogøe et al.
U.S. Appl. No. 18/028,989, filed Mar. 28, 2023, Sprogøe et al.
U.S. Appl. No. 18/053,701, filed Nov. 8, 2022, Sprogøe et al.
U.S. Appl. No. 18/176,372, filed Feb. 28, 2023, Sprogøe et al.
U.S. Appl. No. 18/355,223, filed Jul. 19, 2023, Sprogøe et al.
Abate, et al., "Review of Hypoparathyroidism," Frontiers Endocrimolgy, vol. 7, Art. 172, (Jan. 2017).

(Continued)

*Primary Examiner* — Randall L Beane
(74) *Attorney, Agent, or Firm* — Alston & Bird LLP

(57) ABSTRACT

The present invention relates to PTH prodrugs, pharmaceutical compositions comprising such PTH prodrugs and their uses.

9 Claims, No Drawings
Specification includes a Sequence Listing.

(56) References Cited

U.S. PATENT DOCUMENTS

| | | |
|---|---|---|
| 2014/0248365 A1 | 9/2014 | Rademacher et al. |
| 2015/0065423 A1 | 3/2015 | Laulicht et al. |
| 2015/0290337 A1 | 10/2015 | Vetter et al. |
| 2016/0264636 A1 | 9/2016 | Rebollo Garcia |
| 2019/0224329 A1 | 7/2019 | Sprogøe et al. |
| 2019/0282668 A1 | 9/2019 | Sprogøe et al. |
| 2020/0023041 A1 | 1/2020 | Holten-Andersen et al. |
| 2020/0046725 A1 | 2/2020 | Cleeman et al. |
| 2020/0276270 A1 | 9/2020 | Holten-Anderson et al. |
| 2020/0276276 A1 | 9/2020 | Sprogøe et al. |
| 2020/0360487 A1 | 11/2020 | Sprogøe et al. |
| 2020/0360488 A1 | 11/2020 | Sprogøe et al. |
| 2020/0376089 A1 | 12/2020 | Sprogøe et al. |
| 2021/0196801 A1 | 7/2021 | Sprogøe et al. |
| 2022/0008516 A1 | 1/2022 | Cleemann et al. |
| 2022/0088149 A1 | 3/2022 | Skands et al. |
| 2023/0042670 A1 | 2/2023 | Sprogøe et al. |
| 2023/0121525 A1 | 4/2023 | Sprogøe et al. |
| 2023/0218722 A1 | 7/2023 | Sprogøe et al. |
| 2023/0248836 A1 | 8/2023 | Sprogøe et al. |
| 2023/0321198 A1 | 10/2023 | Sprogøe et al. |
| 2023/0381284 A1 | 11/2023 | Sprogøe et al. |

FOREIGN PATENT DOCUMENTS

| | | |
|---|---|---|
| EP | 0920873 A2 | 6/1999 |
| EP | 1 477 496 A1 | 11/2001 |
| EP | 1 536 334 | 6/2005 |
| EP | 1534334 B1 | 6/2014 |
| WO | WO 02/089789 | 11/2002 |
| WO | WO 2003/064462 A1 | 8/2003 |
| WO | WO 2005/027978 | 3/2005 |
| WO | WO 2005/099768 | 10/2005 |
| WO | WO 2005/099768 A2 | 10/2005 |
| WO | WO 2005/115441 A2 | 12/2005 |
| WO | WO 2006/003014 | 1/2006 |
| WO | WO 2006/136586 | 12/2006 |
| WO | WO 2006/136586 A2 | 12/2006 |
| WO | WO 2007/106597 A3 | 9/2007 |
| WO | WO 2008/034122 | 3/2008 |
| WO | WO 2008/048784 A1 | 4/2008 |
| WO | WO 2008/155134 | 12/2008 |
| WO | WO 2009/009712 | 1/2009 |
| WO | WO 2009/009712 A1 | 1/2009 |
| WO | WO 2009/053106 A1 | 4/2009 |
| WO | WO 2009/095479 | 8/2009 |
| WO | WO 2009/095479 A1 | 8/2009 |
| WO | WO 2009/143412 | 11/2009 |
| WO | WO 2009/156481 | 12/2009 |
| WO | WO 2010/091122 A1 | 8/2010 |
| WO | WO 2011/012715 | 2/2011 |
| WO | WO 2011/012715 A1 | 2/2011 |
| WO | WO 2011/012718 A1 | 2/2011 |
| WO | WO 2011/012719 A1 | 2/2011 |
| WO | WO 2011/012721 A1 | 2/2011 |
| WO | WO 2011/012722 | 2/2011 |
| WO | WO 2011/012722 A1 | 2/2011 |
| WO | WO 2011/012723 A1 | 2/2011 |
| WO | WO 2011/042450 A1 | 4/2011 |
| WO | WO 2011/082368 | 7/2011 |
| WO | WO 2011/082368 A2 | 7/2011 |
| WO | WO 2011/089214 | 7/2011 |
| WO | WO 2011/089215 | 7/2011 |
| WO | WO 2011/089215 A1 | 7/2011 |
| WO | WO 2011/089216 | 7/2011 |
| WO | WO 2011/089216 A1 | 7/2011 |
| WO | WO 2011/123813 | 10/2011 |
| WO | WO 2011/144756 | 11/2011 |
| WO | WO 2012/035139 A1 | 3/2012 |
| WO | WO 2012/002047 | 5/2012 |
| WO | WO 2013/024048 | 2/2013 |
| WO | WO 2013/024049 | 2/2013 |
| WO | WO 2013/024051 A1 | 2/2013 |
| WO | WO 2013/024052 | 2/2013 |
| WO | WO 2013/024053 | 2/2013 |
| WO | WO 2013/024053 A1 | 2/2013 |
| WO | WO 2013/036857 | 3/2013 |
| WO | WO 2013/053856 A1 | 4/2013 |
| WO | WO 2013/108235 A1 | 7/2013 |
| WO | WO 2013/160340 | 10/2013 |
| WO | WO 2014/033540 | 3/2014 |
| WO | WO 2014/056915 A1 | 4/2014 |
| WO | WO 2014/056923 A1 | 4/2014 |
| WO | WO 2014/056926 | 4/2014 |
| WO | WO 2014/056926 A1 | 4/2014 |
| WO | WO 2014/060512 | 4/2014 |
| WO | WO 2014/086961 A1 | 6/2014 |
| WO | WO 2014/173759 A1 | 10/2014 |
| WO | WO 2015/052155 A1 | 4/2015 |
| WO | WO 2016/020373 | 2/2016 |
| WO | WO 2016/020373 A1 | 2/2016 |
| WO | WO 2016/065042 A1 | 4/2016 |
| WO | WO 2016/110577 A1 | 7/2016 |
| WO | WO 2016/193371 A1 | 12/2016 |
| WO | WO 2017/148883 A1 | 9/2017 |
| WO | WO 2018/060310 A1 | 4/2018 |
| WO | WO 2018/060311 A1 | 4/2018 |
| WO | WO 2018/060312 A1 | 4/2018 |
| WO | WO 2018/100174 A1 | 6/2018 |
| WO | WO 2019/219896 A1 | 11/2019 |
| WO | WO 2020/165087 A1 | 8/2020 |

OTHER PUBLICATIONS

Aouchiche, et al., "Teriparatide administration by the Omnipod pump: preliminary experience from two cases with refractory hypoparathyroidism," Endocrine, 76:179-188, (Jan. 2022).

Arrighi, et al., "Bone healing induced by local delivery of an engineered parathyroid hormone prodrug", Biomaterials, Mar. 1, 2009. 1763-1771, 30(9), Elsevier Science Publishers BV., Barking, GB, XP025928044.

Beauchamp, et al., "A New Procedure for the Synthesis of Poly-ethylene Glycol-Protein Aducts; Effects on Functin Receptor Recognition, and clearance of Superoxide Dismutase, Lactoferrin, and α2-Macroglobulin," Analytical Biochemistry, 131, 25-33, (1983).

Belikov, "2.6 Relation between chemical structure, properties of substances and their effect on the organism," Pharmaceutical chemistry: study guide, fourth edition, revised and enlarged edition, M.: MEDpress-inform, p. 27-28, (2007), English translation only.

Bilezikean, et al., "Management of Hypoparathyroidism: Present and Future," J Clin Endocrinol Metab, 101(6):2313-2324, (Jun. 2016).

Bowie, et al., Deciphering the Message in Protein Sequences: Tolerance to Amino Acid Substitutions, Science, 1990, 1306-1310, 247.

Chamow, et al., "Modification of CD4 Immunoadhesin with Monomethoxypoly(ethylene glycol) Aldehyde via Reductive Alkylation," Bioconjugate Chem. 5, 133-140, (1994).

Cheng, et al., "Teriparatide—Indications beyond osteoporosis," Indian Journal of Endocrinology and Metabolisum, vol. 16, Issue 3, pp. 343-348, (May-Jun. 2012).

Cuchert, et al., "Summary Report: Indirect comparisons Mehtods and validity," HAS Department of Medecines Assessment, 66 pages, (Jul. 2009).

Cusano et al., "Use of parathyroid hormone in hypoparathyroidism," J Endocrinol Invest., 36(11): 1121-1127, (Dec. 2013).

Dyson, et al., "May's Chemistry of Synthetic Drugs," Longmans, Greens and Co., Ltd., 5th edition, May 1959, 1-20.

Filpula, et al., "Releasable PEGylation of proteins with customized linkers", Nov. 30, 2007, 29-49, 60(1), Advanced drug delivery reviews, Elsevier, Amsterdam, NL.

Finkelstein, et al., "Effects of Teriparatide Retreatment in Osteoporotic Men and Women," J. Clin Endocrinol Metab, 94(7), 2495-2501, (Jul. 2009).

Florence, et al., Attwood D. Physicochemical principles of pharmacy. 3rd ed.—1998—Easton, Bristol: Aarontype Limited, pp. 18-21, paragraph 1.4.1.

Forteo (teriparatide injection) Label, Highlights of Prescribing Information, Lilly USA, Llc, Initial U.S. Approval: 1987, updated Nov. 2020, revised Sep. 2021.

(56) References Cited

OTHER PUBLICATIONS

Gafni, et al., "Daily Parathyroid Hormone 1-34 Replacement Therapy for Hypoparathyroidism Induces Marked Changes in Bone Turnover and Structure," Journal of Bone and Mineral Research, vol. 27, No. 8, pp. 1811-1820, (Aug. 2012).

Harkevic, "Dependence of the Pharmacotherapeutic Effect on the Properties of Drugs and Conditions of their Use," Pharmacology: textbook, tenth edition, revised, enlarged and corrected edition, M.: GEOTARMedia, p. 72-74, (2010), English translation only.

Hohenstein, et al., "Development and validation of a novel cell-based assay for potency determination of human parathyroid honnone (PM)", Journal of Pharmaceutical and Biomedical Analysis, Sep. 2014, 345-350, 98.

Holten-Anderson, et al., "Design and Preclinical Development of TransCon PTH, an Investigational Sustained-Release PTH Replacement Therapy for Hypoparathyroidism," J Bone Miner Res, doi: 10.1002/jbmr.3824, (Nov. 2019).

Horwitz, et al., "A 7-Day Continuous Infusion of PTH or PTHrP Suppresses Bone Fromation and Uncouples Bone Turnover," Journal of Bone and Mineral Research, vol. 26, No. 9, pp. 2287-2297, (Sep. 2011).

Jakubke, et al., "Amioacids, peptides and proteins," M. Mir Publishers, p. 456 (partial English translation of D6) (1985).

JenKem Technology, USA (accessed by download from http://www,,w.jenkerusa.com/Pages,PEGProducts.aspx on Dec. 18, 2014).

Kahn, et al., Efficacy and Safety of Parathyroid Hormone Replacement With TransCon PTH in Hypoparathyroidism: 26 Week Results From the Phase 3 PaTHway Trial,' Journal of Bone and Mineral Research, 38(1):14-25. doi: 10.1002/jbmr.4726 (Jan. 2023).

Karpf, et al., "A Randomized Double-Blind Placebo-Controled First-In-Human Phase 1 Trial of TransCon PTH in Healthy Adults," Journal of Bone and Mineral Research, Vo. 35, No. 8, pp. 1430-1440, (Aug. 2020).

Khan, et al., "Path Forward: A Randomized, Double-Blind Placebo-Controlled Phase 2 Trial of TransCon PTH in Adult Hypoparathyroidism," The Journal of Clinical Endocrinology & Metabolism, vol. 107: e372-e385 (Aug. 2021).

Kostenuik, et al., "Infrequent Delivery of a Long-Acting PTH-Fc Fusion Protein Has Potent Anabolic Effects on Cortical and Cancellous Bone", Journal of Bone and Mineral Research, 2007, 1534-1547, 22(10).

Levine, et al., "Intrinsic bioconjugation for site-specific protein PEGylation at N-terminal serine", Chemical Communications—Chemcom, Jan. 1, 2014, 6909-6912, 50 (52), XP055305086.

Liu, et al., "PEGylation Site-Dependent Structural Heterogeneity Study of MonoPEGylated Human Parathyroid Hormone Fragment hPTH(1-34)" Langmuir, Sep. 30, 2014, 11421-11427, 30(38), XP05505083.

Lui, et al., "PEGylation Site-Dependent Structura Heterogeneity Study of MonoPEGylated Human Parathyroid hormone Fragment hPTH(1-34)," Langmuir, 30, 11421-11427, (2014).

Mannstadt, et al., "Efficacy and safety of recombinant human parthyroid hormone (1-84) in hypoparathyroidism (REPLACE): a double-blind, placebo-controlled, randomised, phase 3 study," Lancet Diabetes Endocrinol, 1: 275-283, (2013).

Mannstadt, et al., "Safety and Efficacy of 5 Years of Treatment with Recombinant Human Parathyroid Hormone in Adults with Hypoparathyroidism," J Clin Endocrinol Metab, 104(11):5136-5147 (Aug. 2019).

Marx, et al., "Solution Structures of Human Parathyroid Hormone Fragments hPTH(1-34) and hPTH(1-39) and Bovine Parathyroid Hormone Fragment bPTH(1-37)," Biochemical and Biophysical Research Communications, 267, 213-220, (2000).

Maschkowskij, et al., "Maschkowskij M.D. Drugs," M. New Wave Publishers, The Sixteenth Edition, p. 1216, (2012) (Partial English Translation of D5 cited in RU 17038 on Mar. 22, 2021).

Mills, et al., "Estimating the power of indirect Comparisons: A Simulation Study," PLoS ONE, vol. 6, Issue 1, e16237, (Jan. 2011).

Mirza, et al., "Secondary Osteoporosis: Pathophysilolgy and Management," Eur J. Endocrinol. 173(3): R131-R151, doi: 10/. 1530/EJE-15-0118, (Sep. 2015). Part 1.

Mirza, et al., "Secondary Osteoporosis: Pathophysilolgy and Management," Eur J. Endocrinol. 173(3): R131-R151, doi: 10/. 1530/EJE-15-0118, (Sep. 2015). Part 2.

Mitchell, et al., "Long-Term Follow-Up of Patients with Hypoparathyroidism," J Clin Endocrinol Metab, 97: 4507-4514, (2012).

Na, et al., "Capillary electrophoretic characterization of PEGylated human parathyroid hormone with matrix-assisted laser desorption/ionization time-of-flight mass spectrometry", Analytical Biochemistry, Aug. 15, 2004, 322-328, 331(2), Elsevier, Amsterdam, NL.

Nair, et al., "A simple practice guide for dose conversion between animals and human," J Basicc Clin Pharma, 7:27-31, (Mar. 2016).

NOF Corporation Catalog, NOF Corporation, Drug Delivery Systems Catalogue, Ver. 8, 60 pages, (Apr. 2006).

Pan, et al., "Research progress in hormone replacement therapy for hypoparathyroidism after thyroid surgery," Chinese Journal of General Surgery, vol. 24, No. 5, pp. 728-732, (May 2015).

Pekkolay, et al., "Alternative treatment of resistant hypoparathyroidism by intermittent infusion of teriparatide using an insulin pump: A case report," Turk J Phys Med Rehab, 65(2):198-201, (May 2019).

Ponnapakkam, et al., "Treating osteoporosis by targeting parathyroid hormone to bone" Drug Discov Today, Mar. 2014, 204-208, 19(3).

Rejnmark, et al., "PTH replacement therapy of hypoparathyroidism", Bone, Dept. of Endocrinology and Internal Medicine, Aarhus University Hospital, Aarhus, Denmark, May 1, 2012, 50, XP028922570.

Shah, et al., "Teriparatide Therapy and Reduced Postoperative Hospitalization for Postsurgical Hypoparathyroidism," JAMA Otoaryngol Head Neck Surg., 141(9):822-827, (Aug. 2015).

Sikjaer, et al., "Effects of PTH(1-84) therapy on muscle function and quality of life in hypoparathyroidism: results from a randomized controlled trial," Osteoporos Int, 25:1717-1726, (2014).

Sikjaer, et al., "The Effect of Adding PTH(1-84) to onventional Treatment of Hypoparathyroidism: A Randomized, Placebo-Controlled Study," Journal of Bone and Mineral Research, vol. 26, No. 10, pp. 2358-2370, (Oct. 2011).

Smith, et al., "Relevance of Half-Life in Drug Design," J. Med. Chem., 61, 4273-4282, (May 2018).

Smith, et al., "The pH-Rate Profile for the Hydrosysis of a Peptide Bond," J. Am. Chem. Soc., 120, 8910-8913, (1998).

Song, et al., "Validity of indirect comparison for estimating efficacy of competing interventions: empirical evidence from published meta-analyses," BMJ, vol. 326, (Mar. 2003).

Starkova, "Clinical endocrinology: Guidance", edited by N. T. Starkova, third edition, revised and enlarged edition, SPb: Piter, p. 182 , (2002), English translation only.

Thiruchelvam, et al., "Teriparatide Induced Delayed Persistent Hypecalcemia," Case Reports in Endocrinology, vol. 2014, Article IDS 802473, (2014).

Vilardaga, "Molecular basis of parathyroid hormone receptor signaling and trafficking: a family B GPR paradigm," Cell Mol. Life, Sci., 68(1): 1-13, (2011).

Vokes, et al., "Reombinant Human Parathyroid Hormone Effect on Health-Related Quality of Life in Adults With Chronic Hypoparathyroidism," J Clin Endocrinol Metab, 103: 722-731, (Nov. 2018).

Watchorn, "CCLV. The Normal Serum-Calcium and Magnesium of the Rat: Their Relation to Sex and Age," Biochemical Laboratory, Cambridge, 1875-1878, (Nov. 1, 1933).

Wei, et al., The release profiles and bioactivity of parathyroid hormone from poly(lactic-co-glycolic acid) microspheres, Biomaterials, 25, 345-352, (2004).

Winer, et al., "Effects of Pump versus Twice-Daily Injection Delivery of Synthetic Parathyroid Hormone 1-34 in Children with Severe congenital Hypoparathyroidism", J Pediatr., 2014, 556-563, 165(3), NIH, Bethesda, Maryland.

Winer, et al., "Long-Term Treatment of Hypoparathyroidism: A Randomized Controlled Study Comparing Parthyroid Hormone-(1-34) versus Calcitroil and Calcium," The Journal of Clinical Endocrinology & Metabolism, 88(9): 4214-4220, (Sep. 2003).

(56) References Cited

OTHER PUBLICATIONS

Winer, et al., "Synthetic Human Parathyroid Hormone 1-34 Replacement Therapy: A Randomized Crossover Trial Comparing Pumb Versus Injections in the Treatment of Chronic Hypoparathyroidism," J Clin Endocrinol Metab, 97(2):391-399, (2012).

Winer, et al., Synthetic Human Parathyroid Hormone 1-34 vs Calcitriol and Calcium in the Treatment of Hypoparathyroidism, JAMA, 276:631-636, (1996).

Wu, et al., "Disruption of YPS1 and PEP4 genes reduces proteolytic degration of secreted HSA/PTH in Pichia pastoris GS115," J. Ind Microbiol Biotechnol., 40:589-599, (2013).

Zhang, et al., "Molecular-Target-Based Anticancer Photosensitizer: Synthesis and in vitro Photodynamic Activity of Erlotinib-Zinc(II) Phthalocyanine Conjugates," ChemMedChem, 10. 312-320, (Feb. 2015).

Zulenko, et al., "2.3 Dosage of Drugs," Pharmacology. M.: Kolos S, p. 34-35, (2008), English translation only.

New Zealand 751745 Patent examination report 2 dated Jan. 26, 2023.

U.S. Appl. No. 16/118,155, Non-Final Office Action mailed Feb. 11, 2021.

U.S. Appl. No. 16/118,155, Requirement for Restriction/Election mailed Oct. 7, 2020.

U.S. Appl. No. 16/337,713, Final Office Action mailed Aug. 23, 2021.

U.S. Appl. No. 16/337,713, Final Office Action mailed Sep. 1, 2020.

U.S. Appl. No. 16/337,713, Final Office Action mailed Sep. 1, 2022.

U.S. Appl. No. 16/337,713, Non-Final Office Action mailed Feb. 22, 2021.

U.S. Appl. No. 16/337,713, Non-Final Office Action mailed Mar. 25, 2020.

U.S. Appl. No. 16/337,713, Non-Final Office Action mailed May 27, 2022.

U.S. Appl. No. 16/337,713, Notice of Allowance mailed Oct. 26, 2022.

U.S. Appl. No. 16/337,803, Final Office Action mailed Feb. 28, 2023.

U.S. Appl. No. 16/337,803, Final Office Action mailed May 3, 2021.

U.S. Appl. No. 16/337,803, Final Office Action mailed Sep. 21, 2022.

U.S. Appl. No. 16/337,803, Non-Final Office Action mailed Jan. 12, 2021.

U.S. Appl. No. 16/337,803, Non-Final Office Action mailed Mar. 7, 2022.

U.S. Appl. No. 16/337,803, Requirement for Restriction/Election mailed Jun. 10, 2020.

U.S. Appl. No. 16/337,955, Corrected Notice of Allowance mailed Dec. 5, 2022.

U.S. Appl. No. 16/337,955, Final Office Action mailed Jan. 7, 2022.

U.S. Appl. No. 16/337,955, Final Office Action mailed Apr. 15, 2022.

U.S. Appl. No. 16/337,955, Final Office Action mailed Jul. 14, 2022.

U.S. Appl. No. 16/337,955, Non-Final Office Action mailed Jul. 16, 2020.

U.S. Appl. No. 16/337,955, Non-Final Office Action mailed Sep. 7, 2021.

U.S. Appl. No. 16/337,955, Notice of Allowability mailed Apr. 19, 2023.

U.S. Appl. No. 16/337,955, Notice of Allowance mailed Mar. 3, 2023.

U.S. Appl. No. 16/337,955, Notice of Allowance mailed Sep. 6, 2022.

U.S. Appl. No. 16/337,955, Notice of Allowance mailed Oct. 19, 2022.

U.S. Appl. No. 16/988,302, Final Office Action mailed Apr. 27, 2023.

U.S. Appl. No. 16/988,302, Requirement for Restriction/Election mailed Jan. 14, 2022.

U.S. Appl. No. 16/988,386, Non-Final Office Action mailed Oct. 6, 2022.

U.S. Appl. No. 16/988,386, Requirement for Restriction/Election mailed Jul. 6, 2022.

U.S. Appl. No. 16/989,225, Non-Final Office Action mailed Sep. 7, 2021.

U.S. Appl. No. 16/989,225, Requirement for Restriction/Election mailed May 14, 2021.

U.S. Appl. No. 17/055,695, Final Office Action mailed May 19, 2023.

U.S. Appl. No. 17/055,695, Non-Final Office Action mailed Aug. 25, 2023.

U.S. Appl. No. 17/055,695, Requirement for Restriction/Election mailed Jul. 21, 2022.

U.S. Appl. No. 17/488,137, Final Office Action mailed May 13, 2022.

U.S. Appl. No. 17/488,137, Non-Final Office Action mailed Feb. 4, 2022.

U.S. Appl. No. 17/488,137, Requirement for Restriction/Election mailed Nov. 9, 2021.

U.S. Appl. No. 18/053,693, Non-Final Office Action mailed Mar. 20, 2023.

U.S. Appl. No. 18/053,693, Notice of Allowance and Interview Summary mailed Jul. 19, 2023.

U.S. Appl. No. 18/053,693, Requirement for Restriction/Election mailed Jan. 27, 2023.

U.S. Appl. No. 18/053,701, Non-Final Office Action mailed Jun. 22, 2023.

U.S. Appl. No. 18/053,701, Notice of Allowance mailed Oct. 2, 2023.

U.S. Appl. No. 18/063,294, Corrected Notice of Allowance mailed Oct. 2, 2023.

U.S. Appl. No. 18/063,294, Non-Final Office Action mailed Aug. 23, 2023.

U.S. Appl. No. 18/063,294, Notice of Allowance mailed Jun. 20, 2023.

U.S. Appl. No. 18/063,294, Notice of Allowance mailed Sep. 11, 2023.

U.S. Appl. No. 18/355,223, Non-Final Office Action mailed Sep. 21, 2023.

U.S. Appl. No. 18/355,223, Notice of Allowance mailed Nov. 2, 2023.

U.S. Appl. No. 18/053,701, Notice of Allowance mailed Oct. 5, 2023.

U.S. Appl. No. 16/118,155, Final Office Action mailed Sep. 28, 2018.

U.S. Appl. No. 16/988,302, Non-Final Office Action mailed Oct. 3, 2022.

U.S. Appl. No. 16/988,386, Final Office Action mailed May 2, 2023.

U.S. Appl. No. 17/055,695, Non-Final Office Action mailed Nov. 21, 2022.

U.S. Appl. No. 18/063,294, Non-Final Office Action mailed Apr. 28, 2023.

U.S. Appl. No. 16/337,955 Advisory Action mailed Feb. 16, 2021.

U.S. Appl. No. 16/337,955 Final Office Action mailed Dec. 3, 2020.

WIPO Application No. PCT/EP2017/054550, PCT International Preliminary Report on Patentability mailed Sep. 4, 2018.

WIPO Application No. PCT/EP2017/054550, PCT International Search Report and Written Opinion of the International Searching Authority mailed Sep. 8, 2017.

WIPO Application No. PCT/EP2017/074592, PCT International Preliminary Report on Patentability mailed Apr. 2, 2019.

WIPO Application No. PCT/EP2017/074592, PCT International Search Report and Written Opinion of the International Searching Authority mailed Apr. 5, 2018.

WIPO Application No. PCT/EP2017/074594, PCT International Preliminary Report on Patentability mailed Apr. 2, 2019.

WIPO Application No. PCT/EP2017/074594, PCT International Search Report and Written Opinion of the International Searching Authority mailed Apr. 5, 2018.

WIPO Application No. PCT/EP2019/062773, PCT International Preliminary Report on Patentability mailed Nov. 24, 2020.

(56) References Cited

OTHER PUBLICATIONS

WIPO Application No. PCT/EP2019/062773, PCT International Search Report and Written Opinion of the International Searching Authority mailed Nov. 21, 2019.
WIPO Application No. PCT/EP2020/053316, PCT International Search Report and Written Opinion of the International Searching Authority mailed Sep. 4, 2020.
U.S. Appl. No. 16/118,155, filed Aug. 30, 2018, 2020-0276276.
U.S. Appl. No. 17/488,137, filed Sep. 28, 2021, 2022-0008516.
U.S. Appl. No. 18/053,693, filed Nov. 8, 2022, now U.S. Pat. No. 11,793,861.
U.S. Appl. No. 17/055,695, Final Office Action mailed Feb. 7, 2024.
U.S. Appl. No. 16/337,803, Non- Final Office Action mailed Feb. 15, 2024.
U.S. Appl. No. 18/176,372, Non-Final Office Action mailed Apr. 5, 2024.
U.S. Appl. No. 17/055,695, Advisory Action mailed Jun. 24, 2024.

\* cited by examiner

PTH PRODRUGS

CROSS-REFERENCE TO RELATED APPLICATIONS

This application is a continuation of U.S. application Ser. No. 18/053,693 filed Nov. 8, 2022, which is a continuation of U.S. application Ser. No. 17/488,137 filed Sep. 28, 2021, which is a continuation of U.S. application Ser. No. 16/118, 155 filed Aug. 30, 2018, which is the US national stage entry of International Application No. PCT/EP2017/054550 filed Feb. 28, 2017, each of which is incorporated by reference in its entirety for all purposes, and which PCT/EP2017/054550 claims the benefit of EP application Ser. No. 16/158,048.5 filed Mar. 1, 2016, EP application Ser. No. 16/179,294.0 filed Jul. 13, 2016, EP application Ser. No. 16/191,484.1 filed Sep. 29, 2016, and EP application Ser. No. 17/155, 839.8 filed Feb. 13, 2017.

REFERENCE TO SEQUENCE LISTING

This application includes an electronic sequence listing in a file named 601384SEQLST.XML, created on Sep. 8, 2023, and containing 181,931 bytes, which is incorporated by reference.

FIELD OF THE INVENTION

The present invention relates to PTH prodrugs, pharmaceutical compositions comprising such PTH prodrugs and their uses.

BACKGROUND

Hypoparathyroidism is a rare endocrine disease with low serum calcium and inappropriately low (insufficient) circulating parathyroid hormone levels, most often in adults secondary to thyroid surgery. Standard treatment includes activated vitamin D analogues and calcium supplementation, which increases calcium and phosphorus absorption and serum levels at the expense of abnormally increased urinary calcium excretion. Hypoparathyroidism is the only major endocrine condition today, where the hormonal insufficiency in general is not treated by substitution of the missing hormone (PTH).

The prevalence of hypoparathyroidism has recently been systematically studied in Denmark, where a total of more than 2000 patients were identified giving a prevalence of ~24/100 000 inhabitants, among whom only a minority (2/100 000) had hypoparathyroidism due to non-surgical causes. These estimates are in agreement with recent data from the USA, showing a prevalence of the same magnitude for patients with chronic hypoparathyroidism. Endogenous PTH is synthesized and secreted by the parathyroid glands and is the principal endocrine hormone regulating systemic calcium and phosphorus homeostasis. Physiological actions of PTH include releasing calcium and phosphorus from bone, retaining calcium but not phosphorus in the kidney by increasing renal tubular reabsorption of calcium but decreasing renal tubular reabsorption of phosphate, and stimulating the renal production of active vitamin D ($1,25(OH)_2$vitamin D3) which in turn enhances intestinal calcium and phosphorus absorption.

Without the renal actions of PTH to conserve calcium and excrete phosphorus, conventional therapy with vitamin D analogs and calcium supplementation may lead to renal insufficiency or failure due to progressive nephrocalcinosis, as well as ectopic calcifications (in the basal ganglia, the lens of the eye, and the vascular system) due to a chronically increased calcium x phosphorus product, which precipitates out as calcium phosphate crystals when this product is maintained elevated for long periods.

Recently Natpara®, PTH(1-84) was approved by the FDA for the treatment of hypoparathyroidism. Historically Forteo® PTH(1-34) has also been used as once, twice or thrice daily injections for hypoparathyroidism, despite not being approved for this indication.

When PTH is delivered intermittently, such as by current daily or multiple daily injections of PTH(1-84) or PTH(1-34) it acts on bone as an anabolic agent by preferentially activating osteoblasts over osteoclasts. This anabolic effect of intermittent PTH exposure contrasts with the net bone catabolism that can occur with continuous exposure to PTH. The anabolic potential of intermittent administration of PTH agonists has successfully been utilized for the treatment of osteoporosis, where bone turnover is usually high and bone mineral density (BMD) is low, whereas the converse is the case for hypoparathyroidism.

A major complication of hypoparathyroidism is hypercalciuria, due to the lack of PTH dependent calcium reabsorption in the distal renal tubules. Hypercalciuria is associated with an increased risk of nephrocalcinosis, nephrolithiasis and kidney failure. According to the FDAs review of Natpara, daily injections of PTH failed to provide adequate control of urinary calcium excretion, due to the short half-life of this PTH agonist in the body.

Furthermore, unphysiological levels of PTH may be associated with hypercalcemia and hypocalcemia. Treatment with Natpara did not improve the incidence of these complications compared to placebo. This can in part be explained by the unfavorable PK of Natpara. For example, administration of the currently approved doses of Natpara results in greatly supraphysiological levels of PTH with a $C_{max}$ of 300 pg/ml, which returns to baseline at 12 hours. As a result patients are over treated in the initial phase following administration and under treated in the phase leading up to subsequent dosing.

Hypocalcemia is associated with numerous symptoms, some of which can be life threatening, including: tetany; paresthesias; impaired cognition; loss of consciousness with convulsions (grand mal seizures); impaired kidney function; heart arrhythmias and fainting, and even heart failure.

As such, there is a high unmet need for a more physiological PTH therapy, providing a sustained exposure to PTH that enables alleviation of symptoms relating to hypocalcemia, hypercalciuria, and hyperphosphatemia, without causing hypercalcemia.

PTH replacement therapy would be more physiologic if delivered by continuous infusion, such as using an insulin pump. This has for example been demonstrated by Winer et al. (J Pediatr, 2014, 165(3), 556-563), where pump delivery simultaneously normalized bone turnover markers and urine and serum mineral levels, whereas intermittent injection delivery did not.

The normal PTH range is 15-50 pg/ml, and it is important to appreciate that intermittent PTH agonist administration does not constitute physiological replacement therapy. PTH polypeptides have inherently short circulating half-lives because of rapid hepatic metabolism. The rapid clearance of the drug from the body prevents sufficient drug coverage throughout the dosing interval, despite initial supraphysiological drug levels.

Several approaches have been applied to create longer acting version of PTH, including encapsulation of PTH in PLGA microparticles and permanent conjugation of the PTH molecule to either synthetic or peptidic polymers. Kostenuik et al. (J Bone Miner Res, 2007, 22(10), 1534-1547), described a PTH-Fc fusion protein with a longer half-life than PTH(1-34) and studies were conducted in osteopenic ovariectomized rats and mice to determine whether intermittent (one to two per week) injections of PTH-Fc would increase bone mass, density, and strength despite the prolonged duration of exposure to PTH. It was demonstrated that a PTH-derived molecule with a sustained circulating half-life provided comparable anabolic effects on cortical and cancellous bone to daily PTH, but with a reduced dosing frequency.

Another approach has been suggested by Ponnapakkam et al. (Drug Discov Today, 2014, 19(3), 204.208), in which a hybrid polypeptide of PTH and a collagen binding domain caused long-term (up to 12 months) increases in bone mineral density in normal female mice after a single dose.

Patients with hypoparathyroidism typically demonstrate an abnormally low rate of bone turnover resulting in increased bone mineral density, and as such the anabolic effects of PTH should be avoided when treating Hypoparathyroidism, and optimally treatment should normalize their rate of bone turnover, but not increase it to above the normal range, as has been demonstrated with daily treatment with PTH(1-34) and PTH(1-84).

SUMMARY OF THE INVENTION

In summary, there is a need for a more efficacious PTH treatment.

It is therefore an object of the present invention to at least partially overcome the shortcomings described above.

This object is achieved with a PTH prodrug or a pharmaceutically acceptable salt thereof, wherein the prodrug is of formula (Ia) or (Ib)

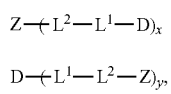

(Ia)

(Ib)

wherein
- -D is a PTH moiety;
- -$L^1$- is a reversible prodrug linker moiety connected to the PTH moiety -D through a functional group of PTH;
- -$L^2$- is a single chemical bond or a spacer moiety;
- —Z is a water-soluble carrier moiety;
- x is an integer selected from the group consisting of 1, 2, 3, 4, 5, 6, 7, 8, 9, 10, 11, 12, 13, 14, 15 or 16; and
- y is an integer selected from the group consisting of 1, 2, 3, 4 and 5.

It was surprisingly found that the PTH prodrugs of the present invention exhibit a low residual activity of the prodrug and provide a sustained release of PTH. As a result, administration of the PTH prodrugs of the present invention leads to a concurrent normalization of serum calcium and a reduction in serum phosphate and thus to an increased serum calcium to serum phosphate ratio compared to treatment with PTH1-84, the current standard of care. At the same time no adverse effects on bone resorption and formation markers and overall bone health in the relevant animal model for the human condition were observed upon administration of physiological doses.

It was also surprisingly found that such PTH prodrugs are capable of achieving a stable plasma profile of PTH which ensures physiological serum and urinary calcium levels or even lower than normal urinary calcium levels.

DETAILED DESCRIPTION

Within the present invention the terms are used having the meaning as follows.

As used herein the term "PTH" refers to all PTH polypeptides, preferably from mammalian species, more preferably from human and mammalian species, more preferably from human and murine species, as well as their variants, analogs, orthologs, homologs, and derivatives and fragments thereof, that are characterized by raising serum calcium and renal phosphorus excretion, and lowering serum phosphorus and renal calcium excretion. The term "PTH" also refers to all PTHrP polypeptides, such as the polypeptide of SEQ ID NO:121, that bind to and activate the common PTH/PTHrP1 receptor. Preferably, the term "PTH" refers to the PTH polypeptide of SEQ ID NO:51 as well as its variants, homologs and derivatives exhibiting essentially the same biological activity, i.e. raising serum calcium and renal phosphorus excretion, and lowering serum phosphorus and renal calcium excretion.

Preferably, the term "PTH" refers to the following polypeptide sequences:

```
(PTH 1-84)
                                    SEQ ID NO: 1
SVSEIQLMHNLGKHLNSMERVEWLRKKLQDVHNFV

ALGAPLAPRDAGSQRPRKKEDNVLVESHEKSLGEA

DKADVNVLTKAKSQ (PTH 1-83)
                                    SEQ ID NO: 2
SVSEIQLMHNLGKHLNSMERVEWLRKKLQDVHNFV

ALGAPLAPRDAGSQRPRKKEDNVLVESHEKSLGEA

DKADVNVLTKAKS (PTH 1-82)
                                    SEQ ID NO: 3
SVSEIQLMHNLGKHLNSMERVEWLRKKLQDVHNFV

ALGAPLAPRDAGSQRPRKKEDNVLVESHEKSLGEA

DKADVNVLTKAK (PTH 1-81)
                                    SEQ ID NO: 4
SVSEIQLMHNLGKHLNSMERVEWLRKKLQDVHNFV

ALGAPLAPRDAGSQRPRKKEDNVLVESHEKSLGEA

DKADVNVLTKA (PTH 1-80)
                                    SEQ ID NO: 5
SVSEIQLMHNLGKHLNSMERVEWLRKKLQDVHNFV

ALGAPLAPRDAGSQRPRKKEDNVLVESHEKSLGEA

DKADVNVLTK (PTH 1-79)
                                    SEQ ID NO: 6
SVSEIQLMHNLGKHLNSMERVEWLRKKLQDVHNFV
```

-continued

ALGAPLAPRDAGSQRPRKKEDNVLVESHEKSLGEA

DKADVNVLT (PTH 1-78)

SEQ ID NO: 7
SVSEIQLMHNLGKHLNSMERVEWLRKKLQDVHNFV

ALGAPLAPRDAGSQRPRKKEDNVLVESHEKSLGEA

DKADVNVL (PTH 1-77)

SEQ ID NO: 8
SVSEIQLMHNLGKHLNSMERVEWLRKKLQDVHNFV

ALGAPLAPRDAGSQRPRKKEDNVLVESHEKSLGEA

DKADVNV (PTH 1-76)

SEQ ID NO: 9
SVSEIQLMHNLGKHLNSMERVEWLRKKLQDVHNFV

ALGAPLAPRDAGSQRPRKKEDNVLVESHEKSLGEA

DKADVN (PTH 1-75)

SEQ ID NO: 10
SVSEIQLMHNLGKHLNSMERVEWLRKKLQDVHNFV

ALGAPLAPRDAGSQRPRKKEDNVLVESHEKSLGEA

DKADV (PTH 1-74)

SEQ ID NO: 11
SVSEIQLMHNLGKHLNSMERVEWLRKKLQDVHNFV

ALGAPLAPRDAGSQRPRKKEDNVLVESHEKSLGEA

DKAD (PTH 1-73)

SEQ ID NO: 12
SVSEIQLMHNLGKHLNSMERVEWLRKKLQDVHNFV

ALGAPLAPRDAGSQRPRKKEDNVLVESHEKSLGEA

DKA (PTH 1-72)

SEQ ID NO: 13
SVSEIQLMHNLGKHLNSMERVEWLRKKLQDVHNFV

ALGAPLAPRDAGSQRPRKKEDNVLVESHEKSLGEA

DK (PTH 1-71)

SEQ ID NO: 14
SVSEIQLMHNLGKHLNSMERVEWLRKKLQDVHNFV

ALGAPLAPRDAGSQRPRKKEDNVLVESHEKSLGEA

D (PTH 1-70)

SEQ ID NO: 15
SVSEIQLMHNLGKHLNSMERVEWLRKKLQDVHNFV

ALGAPLAPRDAGSQRPRKKEDNVLVESHEKSLGEA (PTH 1-69)

SEQ ID NO: 16
SVSEIQLMHNLGKHLNSMERVEWLRKKLQDVHNFV

ALGAPLAPRDAGSQRPRKKEDNVLVESHEKSLGE (PTH 1-68)

SEQ ID NO: 17
SVSEIQLMHNLGKHLNSMERVEWLRKKLQDVHNFV

ALGAPLAPRDAGSQRPRKKEDNVLVESHEKSLG (PTH 1-67)

SEQ ID NO: 18
SVSEIQLMHNLGKHLNSMERVEWLRKKLQDVHNFV

ALGAPLAPRDAGSQRPRKKEDNVLVESHEKSL (PTH 1-66)

SEQ ID NO: 19
SVSEIQLMHNLGKHLNSMERVEWLRKKLQDVHNFV

ALGAPLAPRDAGSQRPRKKEDNVLVESHEKS (PTH 1-65)

SEQ ID NO: 20
SVSEIQLMHNLGKHLNSMERVEWLRKKLQDVHNFV

ALGAPLAPRDAGSQRPRKKEDNVLVESHEK (PTH 1-64)

SEQ ID NO: 21
SVSEIQLMHNLGKHLNSMERVEWLRKKLQDVHNFV

ALGAPLAPRDAGSQRPRKKEDNVLVESHE (PTH 1-63)

SEQ ID NO: 22
SVSEIQLMHNLGKHLNSMERVEWLRKKLQDVHNFV

ALGAPLAPRDAGSQRPRKKEDNVLVESH (PTH 1-62)

SEQ ID NO: 23
SVSEIQLMHNLGKHLNSMERVEWLRKKLQDVHNFV

ALGAPLAPRDAGSQRPRKKEDNVLVES (PTH 1-61)

SEQ ID NO: 24
SVSEIQLMHNLGKHLNSMERVEWLRKKLQDVHNFV

ALGAPLAPRDAGSQRPRKKEDNVLVE (PTH 1-60)

SEQ ID NO: 25
SVSEIQLMHNLGKHLNSMERVEWLRKKLQDVHNFV

ALGAPLAPRDAGSQRPRKKEDNVLV (PTH 1-59)

SEQ ID NO: 26
SVSEIQLMHNLGKHLNSMERVEWLRKKLQDVHNFV

ALGAPLAPRDAGSQRPRKKEDNVL (PTH 1-58)

SEQ ID NO: 27
SVSEIQLMHNLGKHLNSMERVEWLRKKLQDVHNFV

ALGAPLAPRDAGSQRPRKKEDNV (PTH 1-57)

SEQ ID NO: 28
SVSEIQLMHNLGKHLNSMERVEWLRKKLQDVHNFV

ALGAPLAPRDAGSQRPRKKEDN (PTH 1-56)

SEQ ID NO: 29
SVSEIQLMHNLGKHLNSMERVEWLRKKLQDVHNFV

ALGAPLAPRDAGSQRPRKKED (PTH 1-55)

SEQ ID NO: 30
SVSEIQLMHNLGKHLNSMERVEWLRKKLQDVHNFV

-continued

ALGAPLAPRDAGSQRPRKKE (PTH 1-54)

SEQ ID NO: 31

SVSEIQLMHNLGKHLNSMERVEWLRKKLQDVHNFV

ALGAPLAPRDAGSQRPRKK (PTH 1-53)

SEQ ID NO: 32

SVSEIQLMHNLGKHLNSMERVEWLRKKLQDVHNFV

ALGAPLAPRDAGSQRPRK (PTH 1-52)

SEQ ID NO: 33

SVSEIQLMHNLGKHLNSMERVEWLRKKLQDVHNFV

ALGAPLAPRDAGSQRPR (PTH 1-51)

SEQ ID NO: 34

SVSEIQLMHNLGKHLNSMERVEWLRKKLQDVHNFV

ALGAPLAPRDAGSQRP (PTH 1-50)

SEQ ID NO: 35

SVSEIQLMHNLGKHLNSMERVEWLRKKLQDVHNFV

ALGAPLAPRDAGSQR (PTH 1-49)

SEQ ID NO: 36

SVSEIQLMHNLGKHLNSMERVEWLRKKLQDVHNFV

ALGAPLAPRDAGSQ (PTH 1-48)

SEQ ID NO: 37

SVSEIQLMHNLGKHLNSMERVEWLRKKLQDVHNFV

ALGAPLAPRDAGS (PTH 1-47)

SEQ ID NO: 38

SVSEIQLMHNLGKHLNSMERVEWLRKKLQDVHNFV

ALGAPLAPRDAG (PTH 1-46)

SEQ ID NO: 39

SVSEIQLMHNLGKHLNSMERVEWLRKKLQDVHNFV

ALGAPLAPRDA (PTH 1-45)

SEQ ID NO: 40

SVSEIQLMHNLGKHLNSMERVEWLRKKLQDVHNFV

ALGAPLAPRD (PTH 1-44)

SEQ ID NO: 41

SVSEIQLMHNLGKHLNSMERVEWLRKKLQDVHNFV

ALGAPLAPR (PTH 1-43)

SEQ ID NO: 42

SVSEIQLMHNLGKHLNSMERVEWLRKKLQDVHNFV

ALGAPLAP (PTH 1-42)

SEQ ID NO: 43

SVSEIQLMHNLGKHLNSMERVEWLRKKLQDVHNFV

ALGAPLA

-continued (PTH 1-41)

SEQ ID NO: 44

SVSEIQLMHNLGKHLNSMERVEWLRKKLQDVHNFV

ALGAPL (PTH 1-40)

SEQ ID NO: 45

SVSEIQLMHNLGKHLNSMERVEWLRKKLQDVHNFV

ALGAP (PTH 1-39)

SEQ ID NO: 46

SVSEIQLMHNLGKHLNSMERVEWLRKKLQDVHNFV

ALGA (PTH 1-38)

SEQ ID NO: 47

SVSEIQLMHNLGKHLNSMERVEWLRKKLQDVHNFV

ALG (PTH 1-37)

SEQ ID NO: 48

SVSEIQLMHNLGKHLNSMERVEWLRKKLQDVHNFV

AL (PTH 1-36)

SEQ ID NO: 49

SVSEIQLMHNLGKHLNSMERVEWLRKKLQDVHNFV

A (PTH 1-35)

SEQ ID NO: 50

SVSEIQLMHNLGKHLNSMERVEWLRKKLQDVHNFV (PTH 1-34)

SEQ ID NO: 51

SVSEIQLMHNLGKHLNSMERVEWLRKKLQDVHNF (PTH 1-33)

SEQ ID NO: 52

SVSEIQLMHNLGKHLNSMERVEWLRKKLQDVHN (PTH 1-32)

SEQ ID NO: 53

SVSEIQLMHNLGKHLNSMERVEWLRKKLQDVH (PTH 1-31)

SEQ ID NO: 54

SVSEIQLMHNLGKHLNSMERVEWLRKKLQDV (PTH 1-30)

SEQ ID NO: 55

SVSEIQLMHNLGKHLNSMERVEWLRKKLQD (PTH 1-29)

SEQ ID NO: 56

SVSEIQLMHNLGKHLNSMERVEWLRKKLQ (PTH 1-28)

SEQ ID NO: 57

SVSEIQLMHNLGKHLNSMERVEWLRKKL (PTH 1-27)

SEQ ID NO: 58

SVSEIQLMHNLGKHLNSMERVEWLRKK (PTH 1-26)

SEQ ID NO: 59

SVSEIQLMHNLGKHLNSMERVEWLRK (PTH 1-25)

SEQ ID NO: 60

SVSEIQLMHNLGKHLNSMERVEWLR

-continued (amidated PTH 1-84)
                                    SEQ ID NO: 61
SVSEIQLMHNLGKHLNSMERVEWLRKKLQDVHNFV

ALGAPLAPRDAGSQRPRKKEDNVLVESHEKSLGEA

DKADVNVLTKAKSQ;
wherein the C-terminus is amidated (amidated PTH 1-83)
                                    SEQ ID NO: 62
SVSEIQLMHNLGKHLNSMERVEWLRKKLQDVHNFV

ALGAPLAPRDAGSQRPRKKEDNVLVESHEKSLGEA

DKADVNVLTKAKS;
wherein the C-terminus is amidated (amidated PTH 1-82)
                                    SEQ ID NO: 63
SVSEIQLMHNLGKHLNSMERVEWLRKKLQDVHNFV

ALGAPLAPRDAGSQRPRKKEDNVLVESHEKSLGEA

DKADVNVLTKAK;
wherein the C-terminus is amidated (amidated PTH 1-81)
                                    SEQ ID NO: 64
SVSEIQLMHNLGKHLNSMERVEWLRKKLQDVHNFV

ALGAPLAPRDAGSQRPRKKEDNVLVESHEKSLGEA

DKADVNVLTKA;
wherein the C-terminus is amidated (amidated PTH 1-80)
                                    SEQ ID NO: 65
SVSEIQLMHNLGKHLNSMERVEWLRKKLQDVHNFV

ALGAPLAPRDAGSQRPRKKEDNVLVESHEKSLGEA

DKADVNVLTK;
wherein the C-terminus is amidated (amidated PTH 1-79)
                                    SEQ ID NO: 66
SVSEIQLMHNLGKHLNSMERVEWLRKKLQDVHNFV

ALGAPLAPRDAGSQRPRKKEDNVLVESHEKSLGEA

DKADVNVLT;
wherein the C-terminus is amidated (amidated PTH 1-78)
                                    SEQ ID NO: 67
SVSEIQLMHNLGKHLNSMERVEWLRKKLQDVHNFV

ALGAPLAPRDAGSQRPRKKEDNVLVESHEKSLGEA

DKADVNVL;
wherein the C-terminus is amidated (amidated PTH 1-77)
                                    SEQ ID NO: 68
SVSEIQLMHNLGKHLNSMERVEWLRKKLQDVHNFV

ALGAPLAPRDAGSQRPRKKEDNVLVESHEKSLGEA

DKADVNV;
wherein the C-terminus is amidated (amidated PTH 1-76)
                                    SEQ ID NO: 69
SVSEIQLMHNLGKHLNSMERVEWLRKKLQDVHNFV

ALGAPLAPRDAGSQRPRKKEDNVLVESHEKSLGEA

DKADVN;
wherein the C-terminus is amidated (amidated PTH 1-75)
                                    SEQ ID NO: 70
SVSEIQLMHNLGKHLNSMERVEWLRKKLQDVHNFV

ALGAPLAPRDAGSQRPRKKEDNVLVESHEKSLGEA

DKADV;
wherein the C-terminus is amidated (amidated PTH 1-74)
                                    SEQ ID NO: 71
SVSEIQLMHNLGKHLNSMERVEWLRKKLQDVHNFV

ALGAPLAPRDAGSQRPRKKEDNVLVESHEKSLGEA

DKAD;
wherein the C-terminus is amidated (amidated PTH 1-73)
                                    SEQ ID NO: 72
SVSEIQLMHNLGKHLNSMERVEWLRKKLQDVHNFV

ALGAPLAPRDAGSQRPRKKEDNVLVESHEKSLGEA

DKA;
wherein the C-terminus is amidated (amidated PTH 1-72)
                                    SEQ ID NO: 73
SVSEIQLMHNLGKHLNSMERVEWLRKKLQDVHNFV

ALGAPLAPRDAGSQRPRKKEDNVLVESHEKSLGEA

DK;
wherein the C-terminus is amidated (amidated PTH 1-71)
                                    SEQ ID NO: 74
SVSEIQLMHNLGKHLNSMERVEWLRKKLQDVHNFV

ALGAPLAPRDAGSQRPRKKEDNVLVESHEKSLGEA

D;
wherein the C-terminus is amidated (amidated PTH 1-70)
                                    SEQ ID NO: 75
SVSEIQLMHNLGKHLNSMERVEWLRKKLQDVHNFV

ALGAPLAPRDAGSQRPRKKEDNVLVESHEKSLGE

A;
wherein the C-terminus is amidated (amidated PTH 1-69)
                                    SEQ ID NO: 76
SVSEIQLMHNLGKHLNSMERVEWLRKKLQDVHNFV ALGAPLAPRDAGSQRPRKKEDNVLVESHEKSLGE;
wherein the C-terminus is amidated (amidated PTH 1-68)
                                    SEQ ID NO: 77
SVSEIQLMHNLGKHLNSMERVEWLRKKLQDVHNFV ALGAPLAPRDAGSQRPRKKEDNVLVESHEKSLG;
wherein the C-terminus is amidated (amidated PTH 1-67)
                                    SEQ ID NO: 78
SVSEIQLMHNLGKHLNSMERVEWLRKKLQDVHNFV ALGAPLAPRDAGSQRPRKKEDNVLVESHEKSL;
wherein the C-terminus is amidated (amidated PTH 1-66)
                                    SEQ ID NO: 79
SVSEIQLMHNLGKHLNSMERVEWLRKKLQDVHNFV

```
ALGAPLAPRDAGSQRPRKKEDNVLVESHEKS;
wherein the C-terminus is amidated (amidated PTH 1-65)
                                    SEQ ID NO: 80
SVSEIQLMHNLGKHLNSMERVEWLRKKLQDVHNFV ALGAPLAPRDAGSQRPRKKEDNVLVESHEK;
wherein the C-terminus is amidated (amidated PTH 1-64)
                                    SEQ ID NO: 81
SVSEIQLMHNLGKHLNSMERVEWLRKKLQDVHNFV ALGAPLAPRDAGSQRPRKKEDNVLVESHE;
wherein the C-terminus is amidated (amidated PTH 1-63)
                                    SEQ ID NO: 82
SVSEIQLMHNLGKHLNSMERVEWLRKKLQDVHNFV ALGAPLAPRDAGSQRPRKKEDNVLVESH;
wherein the C-terminus is amidated (amidated PTH 1-62)
                                    SEQ ID NO: 83
SVSEIQLMHNLGKHLNSMERVEWLRKKLQDVHNFV ALGAPLAPRDAGSQRPRKKEDNVLVES;
wherein the C-terminus is amidated (amidated PTH 1-61)
                                    SEQ ID NO: 84
SVSEIQLMHNLGKHLNSMERVEWLRKKLQDVHNFV ALGAPLAPRDAGSQRPRKKEDNVLVE;
wherein the C-terminus is amidated (amidated PTH 1-60)
                                    SEQ ID NO: 85
SVSEIQLMHNLGKHLNSMERVEWLRKKLQDVHNFV ALGAPLAPRDAGSQRPRKKEDNVLV;
wherein the C-terminus is amidated (amidated PTH 1-59)
                                    SEQ ID NO: 86
SVSEIQLMHNLGKHLNSMERVEWLRKKLQDVHNFV ALGAPLAPRDAGSQRPRKKEDNVL;
wherein the C-terminus is amidated (amidated PTH 1-58)
                                    SEQ ID NO: 87
SVSEIQLMHNLGKHLNSMERVEWLRKKLQDVHNFV ALGAPLAPRDAGSQRPRKKEDNV;
wherein the C-terminus is amidated (amidated PTH 1-57)
                                    SEQ ID NO: 88
SVSEIQLMHNLGKHLNSMERVEWLRKKLQDVHNFV ALGAPLAPRDAGSQRPRKKEDN;
wherein the C-terminus is amidated (amidated PTH 1-56)
                                    SEQ ID NO: 89
SVSEIQLMHNLGKHLNSMERVEWLRKKLQDVHNFV ALGAPLAPRDAGSQRPRKKED;
wherein the C-terminus is amidated (amidated PTH 1-55)
                                    SEQ ID NO: 90
SVSEIQLMHNLGKHLNSMERVEWLRKKLQDVHNFV ALGAPLAPRDAGSQRPRKKE;
wherein the C-terminus is amidated (amidated PTH 1-54)
                                    SEQ ID NO: 91
SVSEIQLMHNLGKHLNSMERVEWLRKKLQDVHNFV ALGAPLAPRDAGSQRPRKK;
wherein the C-terminus is amidated (amidated PTH 1-53)
                                    SEQ ID NO: 92
SVSEIQLMHNLGKHLNSMERVEWLRKKLQDVHNFV ALGAPLAPRDAGSQRPRK;
wherein the C-terminus is amidated (amidated PTH 1-52)
                                    SEQ ID NO: 93
SVSEIQLMHNLGKHLNSMERVEWLRKKLQDVHNFV ALGAPLAPRDAGSQRPR;
wherein the C-terminus is amidated (amidated PTH 1-51)
                                    SEQ ID NO: 94
SVSEIQLMHNLGKHLNSMERVEWLRKKLQDVHNFV ALGAPLAPRDAGSQRP;
wherein the C-terminus is amidated (amidated PTH 1-50)
                                    SEQ ID NO: 95
SVSEIQLMHNLGKHLNSMERVEWLRKKLQDVHNFV ALGAPLAPRDAGSQR;
wherein the C-terminus is amidated (amidated PTH 1-49)
                                    SEQ ID NO: 96
SVSEIQLMHNLGKHLNSMERVEWLRKKLQDVHNFV ALGAPLAPRDAGSQ;
wherein the C-terminus is amidated (amidated PTH 1-48)
                                    SEQ ID NO: 97
SVSEIQLMHNLGKHLNSMERVEWLRKKLQDVHNFV ALGAPLAPRDAGS;
wherein the C-terminus is amidated (amidated PTH 1-47)
                                    SEQ ID NO: 98
SVSEIQLMHNLGKHLNSMERVEWLRKKLQDVHNFV ALGAPLAPRDAG;
wherein the C-terminus is amidated (amidated PTH 1-46)
                                    SEQ ID NO: 99
SVSEIQLMHNLGKHLNSMERVEWLRKKLQDVHNFV ALGAPLAPRDA;
wherein the C- terminus is amidated (amidated PTH 1-45)
                                    SEQ ID NO: 100
SVSEIQLMHNLGKHLNSMERVEWLRKKLQDVHNFV ALGAPLAPRD;
wherein the C- terminus is amidated (amidated PTH 1-44)
                                    SEQ ID NO: 101
SVSEIQLMHNLGKHLNSMERVEWLRKKLQDVHNFV ALGAPLAPR;
wherein the C- terminus is amidated (amidated PTH 1-43)
                                    SEQ ID NO: 102
SVSEIQLMHNLGKHLNSMERVEWLRKKLQDVHNFV
```

ALGAPLAP;
wherein the C-terminus is amidated (amidated PTH 1-42)
SEQ ID NO: 103
SVSEIQLMHNLGKHLNSMERVEWLRKKLQDVHNFV
ALGAPLA;
wherein the C-terminus is amidated (amidated PTH 1-41)
SEQ ID NO: 104
SVSEIQLMHNLGKHLNSMERVEWLRKKLQDVHNFV
ALGAPL;
wherein the C-terminus is amidated (amidated PTH 1-40)
SEQ ID NO: 105
SVSEIQLMHNLGKHLNSMERVEWLRKKLQDVHNFV
ALGAP;
wherein the C-terminus is amidated (amidated PTH 1-39)
SEQ ID NO: 106
SVSEIQLMHNLGKHLNSMERVEWLRKKLQDVHNFV
ALGA;
wherein the C-terminus is amidated (amidated PTH 1-38)
SEQ ID NO: 107
SVSEIQLMHNLGKHLNSMERVEWLRKKLQDVHNFV
ALG;
wherein the C-terminus is amidated (amidated PTH 1-37)
SEQ ID NO: 108
SVSEIQLMHNLGKHLNSMERVEWLRKKLQDVHNFV
AL;
wherein the C-terminus is amidated (amidated PTH 1-36)
SEQ ID NO: 109
SVSEIQLMHNLGKHLNSMERVEWLRKKLQDVHNFV
A;
wherein the C-terminus is amidated (amidated PTH 1-35)
SEQ ID NO: 110
SVSEIQLMHNLGKHLNSMERVEWLRKKLQDVHNF
V;
wherein the C-terminus is amidated (amidated PTH 1-34)
SEQ ID NO: 111
SVSEIQLMHNLGKHLNSMERVEWLRKKLQDVHNF;
wherein the C-terminus is amidated (amidated PTH 1-33)
SEQ ID NO: 112
SVSEIQLMHNLGKHLNSMERVEWLRKKLQDVHN;
wherein the C-terminus is amidated (amidated PTH 1-32)
SEQ ID NO: 113
SVSEIQLMHNLGKHLNSMERVEWLRKKLQDVH;
wherein the C-terminus is amidated (amidated PTH 1-31)
SEQ ID NO: 114
SVSEIQLMHNLGKHLNSMERVEWLRKKLQDV;
wherein the C-terminus is amidated (amidated PTH 1-30)
SEQ ID NO: 115
SVSEIQLMHNLGKHLNSMERVEWLRKKLQD;
wherein the C-terminus is amidated (amidated PTH 1-29)
SEQ ID NO: 116
SVSEIQLMHNLGKHLNSMERVEWLRKKLQ;
wherein the C-terminus is amidated (amidated PTH 1-28)
SEQ ID NO: 117
SVSEIQLMHNLGKHLNSMERVEWLRKKL;
wherein the C-terminus is amidated (amidated PTH 1 -27)
SEQ ID NO: 118
SVSEIQLMHNLGKHLNSMERVEWLRKK;
wherein the C-terminus is amidated (amidated PTH 1-26)
SEQ ID NO: 119
SVSEIQLMHNLGKHLNSMERVEWLRK;
wherein the C-terminus is amidated (amidated PTH 1-25)
SEQ ID NO: 120
SVSEIQLMHNLGKHLNSMERVEWLR;
wherein the C-terminus is amidated (PTHrP)
SEQ ID NO: 121
AVSEHQLLHDKGKSIQDLRRRFFLHHLIAEIHTAE

IRATSEVSPNSKPSPNTKNHPVRFGSDDEGRYLTQ

ETNKVETYKEQPLKTPGKKKKGKPGKRKEQEKKKR

RTRSAWLDSGVTGSGLEGDHLSDTSTTSLELDSRR

H

More preferably, the term "PTH" refers to the sequence of SEQ ID: NOs 47, 48, 49, 50, 51, 52, 53, 54, 55, 107, 108, 109, 110, 111, 112, 113, 114 and 115. Even more preferably, the term "PTH" refers to the sequence of SEQ ID: NOs 50, 51, 52, 110, 111 and 112. In a particularly preferred embodiment the term "PTH" refers to the sequence of SEQ ID NO:51.

As used herein, the term "PTH polypeptide variant" refers to a polypeptide from the same species that differs from a reference PTH or PTHrP polypeptide. Preferably, such reference is a PTH polypeptide sequence and has the sequence of SEQ ID NO:51. Generally, differences are limited so that the amino acid sequence of the reference and the variant are closely similar 25 overall and, in many regions, identical. Preferably, PTH polypeptide variants are at least 70%, 80%, 90%, or 95% identical to a reference PTH or PTHrP polypeptide, preferably to the PTH polypeptide of SEQ ID NO:51. By a polypeptide having an amino acid sequence at least, for example, 95% "identical" to a query amino acid sequence, it is intended that the amino acid sequence of the subject polypeptide is identical to the query sequence except that the subject 30 polypeptide sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein. Preferably, the query sequence is the sequence of SEQ ID NO:51.

Such PTH polypeptide variants may be naturally occurring variants, such as naturally occurring allelic variants encoded by one of several alternate forms of a PTH or PTHrP occupying a given locus on a chromosome or an organism, or isoforms encoded by naturally occurring splice variants originating from a single primary transcript. Alternatively, a PTH polypeptide variant may be a variant that is not known to occur naturally and that can be made by mutagenesis techniques known in the art.

It is known in the art that one or more amino acids may be deleted from the N-terminus or C-terminus of a bioactive polypeptide without substantial loss of biological function. Such N- and/or C-terminal deletions are also encompassed by the term PTH polypeptide variant.

It is also recognized by one of ordinary skill in the art that some amino acid sequences of PTH or PTHrP polypeptides can be varied without significant effect of the structure or function of the polypeptide. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

The term PTH polypeptide also encompasses all PTH and PTHrP polypeptides encoded by PTH and PTHrP analogs, orthologs, and/or species homologs. It is also recognized by one of ordinary skill in the art that PTHrP and PTHrP analogs bind to activate the common PTH/PTHrP1 receptor, so the term PTH polypeptide also encompasses all PTHrP analogs. As used herein, the term "PTH analog" refers to PTH and PTHrP of different and unrelated organisms which perform the same functions in each organism but which did not originate from an ancestral structure that the organisms' ancestors had in common. Instead, analogous PTH and PTHrP arose separately and then later evolved to perform the same or similar functions. In other words, analogous PTH and PTHrP polypeptides are polypeptides with quite different amino acid sequences but that perform the same biological activity, namely raising serum calcium and renal phosphorus excretion, and lowering serum phosphorus and renal calcium excretion.

As used herein the term "PTH ortholog" refers to PTH and PTHrP within two different species which sequences are related to each other via a common homologous PTH or PTHrP in an ancestral species, but which have evolved to become different from each other.

As used herein, the term "PTH homolog" refers to PTH and PTHrP of different organisms which perform the same functions in each organism and which originate from an ancestral structure that the organisms' ancestors had in common. In other words, homologous PTH polypeptides are polypeptides with quite similar amino acid sequences that perform the same biological activity, namely raising serum calcium and renal phosphorus excretion, and lowering serum phosphorus and renal calcium excretion. Preferably, PTH polypeptide homologs may be defined as polypeptides exhibiting at least 40%, 50%, 60%, 70%, 80%, 90% or 95% identity to a reference PTH or PTHrP polypeptide, preferably the PTH polypeptide of SEQ ID NO:51.

Thus, a PTH polypeptide according to the invention may be, for example: (i) one in which at least one of the amino acids residues is substituted with a conserved or non-conserved amino acid residue, preferably a conserved amino acid residue, and such substituted amino acid residue may or may not be one encoded by the genetic code; and/or (ii) one in which at least one of the amino acid residues includes a substituent group; and/or (iii) one in which the PTH polypeptide is fused with another compound, such as a compound to increase the half-life of the polypeptide (for example, polyethylene glycol); and/or (iv) one in which additional amino acids are fused to the PTH polypeptide, such as an IgG Fc fusion region polypeptide or leader or secretory sequence or a sequence which is employed for purification of the above form of the polypeptide or a pre-protein sequence.

As used herein, the term "PTH polypeptide fragment" refers to any polypeptide comprising a contiguous span of a part of the amino acid sequence of a PTH or PTHrP polypeptide, preferably the polypeptide of SEQ ID NO:51.

More specifically, a PTH polypeptide fragment comprises at least 6, such as at least 8, at least 10 or at least 17 consecutive amino acids of a PTH or PTHrP polypeptide, more preferably of the polypeptide of SEQ ID NO:51. A PTH polypeptide fragment may additionally be described as sub-genuses of PTH or PTHrP polypeptides comprising at least 6 amino acids, wherein "at least 6" is defined as any integer between 6 and the integer representing the C-terminal amino acid of a PTH or PTHrP polypeptide, preferably of the polypeptide of SEQ ID No:51. Further included are species of PTH or PTHrP polypeptide fragments at least 6 amino acids in length, as described above, that are further specified in terms of their N-terminal and C-terminal positions. Also encompassed by the term "PTH polypeptide fragment" as individual species are all PTH or PTHrP polypeptide fragments, at least 6 amino acids in length, as described above, that may be particularly specified by a N-terminal and C-terminal position. That is, every combination of a N-terminal and C-terminal position that a fragment at least 6 contiguous amino acid residues in length could occupy, on any given amino acid sequence of a PTH or PTHrP polypeptide, preferably the PTH polypeptide of SEQ ID: NO51, is included in the present invention.

The term "PTH" also includes poly(amino acid) conjugates which have a sequence as described above, but having a backbone that comprises both amide and non-amide linkages, such as ester linkages, like for example depsipeptides. Depsipeptides are chains of amino acid residues in which the backbone comprises both amide (peptide) and ester bonds. Accordingly, the term "side chain" as used herein refers either to the moiety attached to the alpha-carbon of an amino acid moiety, if the amino acid moiety is connected through amine bonds such as in polypeptides, or to any carbon atom-comprising moiety attached to the backbone of a poly(amino acid) conjugate, such as for example in the case of depsipeptides. Preferably, the term "PTH" refers to polypeptides having a backbone formed through amide (peptide) bonds.

As the term PTH includes the above-described variants, analogs, orthologs, homologs, derivatives and fragments of PTH and PTHrP, all references to specific positions within a reference sequence also include the equivalent positions in variants, analogs, orthologs, homologs, derivatives and fragments of a PTH or PTHrP moiety, even if not specifically mentioned.

As used herein, the term "random coil" refers to a peptide or protein adopting/having/forming, preferably having, a conformation which substantially lacks a defined secondary and tertiary structure as determined by circular dichroism spectroscopy performed in aqueous buffer at ambient temperature, and pH 7.4. Preferably, ambient temperature is about 20° C., i.e. between 18° C. and 22° C., most preferably ambient temperature is 20° C.

As used herein the term "pharmaceutical composition" refers to a composition containing one or more active ingredients, for example a drug or a prodrug, here specifically the PTH prodrugs of the present invention, and optionally one or more excipients, as well as any product which results, directly or indirectly, from combination, complexation or aggregation of any two or more of the ingredients of the composition, or from dissociation of one or more of the ingredients, or from other types of reactions or interactions of one or more of the ingredients. Accordingly, the pharmaceutical compositions of the present invention encompass any composition made by admixing one or more PTH prodrugs of the present invention and optionally a pharmaceutically acceptable excipient.

As used herein the term "liquid composition" refers to a mixture comprising water-soluble PTH prodrug and one or more solvents, such as water.

The term "suspension composition" relates to a mixture comprising water-insoluble PTH prodrug, where for example the carrier Z' is a hydrogel, and one or more solvents, such as water. Due to the water-insoluble polymer, the polymeric prodrug cannot dissolve and renders the prodrug in a particulate state.

As used herein, the term "dry composition" means that a pharmaceutical composition is provided in a dry form. Suitable methods for drying are spray-drying and lyophilization, i.e. freeze-drying. Such dry composition of prodrug has a residual water content of a maximum of 10%, preferably less than 5% and more preferably less than 2%, determined according to Karl Fischer. Preferably, the pharmaceutical composition of the present invention is dried by lyophilization.

The term "drug" as used herein refers to a substance used in the treatment, cure, prevention, or diagnosis of a disease or used to otherwise enhance physical or mental well-being. If a drug is conjugated to another moiety, the moiety of the resulting product that originated from the drug is referred to as "biologically active moiety". The PTH prodrug of the present invention comprise a PTH moiety which is released from the PTH prodrug in the form of the drug PTH.

As used herein the term "prodrug" refers to a conjugate comprising a biologically active moiety reversibly and covalently connected to a specialized protective group through a reversible prodrug linker moiety which is a linker moiety comprising a reversible linkage with the biologically active moiety and wherein the specialized protective group alters or eliminates undesirable properties in the parent molecule. This also includes the enhancement of desirable properties in the drug and the suppression of undesirable properties. The specialized non-toxic protective group is referred to as "carrier". A prodrug releases the reversibly and covalently bound biologically active moiety in the form of its corresponding drug. In other words, a prodrug is a conjugate comprising a biologically active moiety which is covalently and reversibly conjugated to a carrier moiety via a reversible prodrug linker moiety, which covalent and reversible conjugation of the carrier to the reversible prodrug linker moiety is either directly or through a spacer. Such conjugate releases the formerly conjugated biologically active moiety in the form of a free drug.

A "biodegradable linkage" or a "reversible linkage" is a linkage that is hydrolytically degradable, i.e. cleavable, in the absence of enzymes under physiological conditions (aqueous buffer at pH 7.4, 37° C.) with a half-life ranging from one hour to two months, preferably from one hour to one month. Accordingly, a stable linkage is a linkage having a half-life under physiological conditions (aqueous buffer at pH 7.4, 37° C.) of more than two months.

Accordingly, a "reversible prodrug linker moiety" is a moiety which is covalently conjugated to a biologically active moiety, such as PTH, through a reversible linkage and is also covalently conjugated to a carrier moiety, such as —Z or —Z', wherein the covalent conjugation to said carrier moiety is either directly or through a spacer moiety, such as -$L^2$-. Preferably the linkage between —Z or —Z' and -$L^2$- is a stable linkage.

As used herein, the term "traceless prodrug linker" means a reversible prodrug linker which upon cleavage releases the drug in its free form. As used herein, the term "free form" of a drug means the drug in its unmodified, pharmacologically active form.

As used herein, the term "excipient" refers to a diluent, adjuvant, or vehicle with which the therapeutic, such as a drug or prodrug, is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or biologically active moiety, together with a suitable amount of excipient so as to provide the form for proper administration to the patient. The formulation should suit the mode of administration.

As used herein, the term "reagent" means a chemical compound which comprises at least one functional group for reaction with the functional group of another chemical compound or drug. It is understood that a drug comprising a functional group (such as a primary or secondary amine or hydroxyl functional group) is also a reagent.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—"

or "—X—", whereas each "—" indicates attachment to another moiety. Accordingly, a biologically active moiety is released from a prodrug as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N(R)—" can be attached to two moieties or interrupting a moiety either as "—C(O)N(R)—" or as "—N(R)C(O)—". Similarly, a moiety

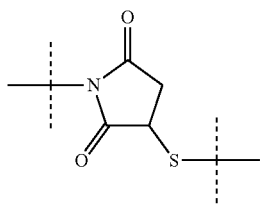

can be attached to two moieties or can interrupt a moiety either as

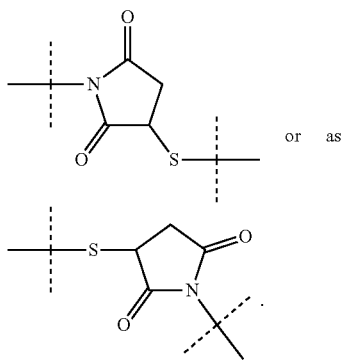

or as

As used herein, the term "functional group" means a group of atoms which can react with other groups of atoms. Functional groups include but are not limited to the following groups: carboxylic acid (—(C═O)OH), primary or secondary amine (—NH$_2$, —NH—), maleimide, thiol (—SH), sulfonic acid (—(O═S═O)OH), carbonate, carbamate (—O(C═O)N<), hydroxyl (—OH), aldehyde (—(C═O)H), ketone (—(C═O)—), hydrazine (>N—N<), isocyanate, isothiocyanate, phosphoric acid (—O(P═O)OHOH), phosphonic acid (—O(P═O)OHH), haloacetyl, alkyl halide, acryloyl, aryl fluoride, hydroxylamine, disulfide, sulfonamides, sulfuric acid, vinyl sulfone, vinyl ketone, diazoalkane, oxirane, and aziridine.

In case the prodrugs of the present invention comprise one or more acidic or basic groups, the invention also comprises their corresponding pharmaceutically or toxicologically acceptable salts, in particular their pharmaceutically utilizable salts. Thus, the prodrugs of the present invention comprising acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Prodrugs of the present invention comprising one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the prodrugs of the present invention simultaneously comprise acidic and basic groups, the invention also includes, in addition to the salt forms mentioned, inner salts or betaines (zwitterions). The respective salts can be obtained by customary methods which are known to the person skilled in the art like, for example by contacting these prodrugs with an organic or inorganic acid or base in a solvent or dispersant, or by anion exchange or cation exchange with other salts. The present invention also includes all salts of the prodrugs of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means a substance that does cause harm when administered to a patient and preferably means approved by a regulatory agency, such as the EMA (Europe) and/or the FDA (US) and/or any other national regulatory agency for use in animals, preferably for use in humans.

As used herein the term "about" in combination with a numerical value is used to indicate a range ranging from and including the numerical value plus and minus no more than 10% of said numerical value, more preferably no more than 8% of said numerical value, even more preferably no more than 5% of said numerical value and most preferably no more than 2% of said numerical value. For example, the phrase "about 200" is used to mean a range ranging from and including 200+/−10%, i.e. ranging from and including 180 to 220; preferably 200+/−8%, i.e. ranging from and including 184 to 216; even more preferably ranging from and including 200+/−5%, i.e. ranging from and including 190 to 210; and most preferably 200+/−2%, i.e. ranging from and including 196 to 204. It is understood that a percentage given as "about 20%" does not mean "20%+/−10%", i.e. ranging from and including 10 to 30%, but "about 20%" means ranging from and including 18 to 22%, i.e. plus and minus 10% of the numerical value which is 20.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical group(s) and/or moiety/moieties, such as, for example, one or more functional group(s). Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that for insoluble polymers, such as hydrogels, no meaningful molecular weight ranges can be provided. It is understood that also a protein is a polymer in which the amino acids are the repeating structural units, even though the side chains of each amino acid may be different.

As used herein, the term "polymeric" means a reagent or a moiety comprising one or more polymer(s) or polymer moiety/moieties. A polymeric reagent or moiety may optionally also comprise one or more other moiety/moieties, which are preferably selected from the group consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

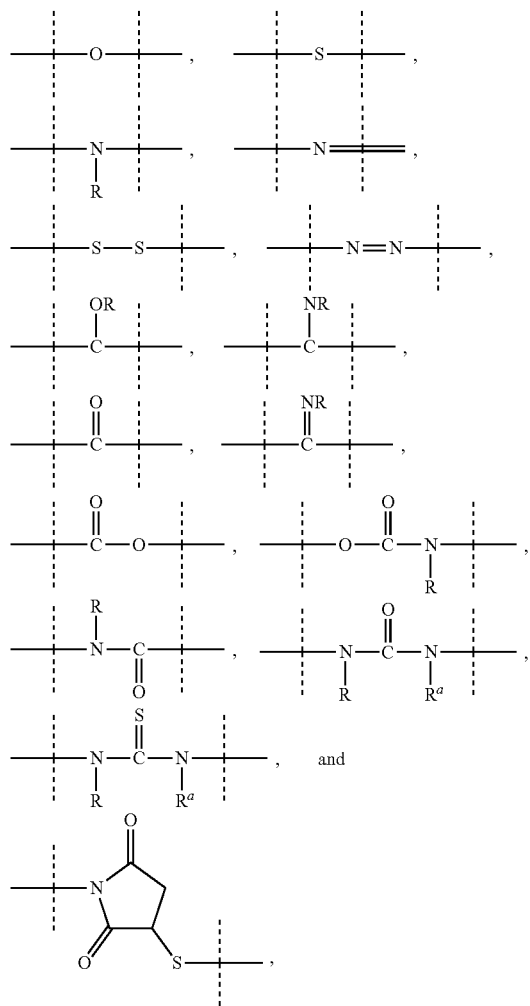

wherein
dashed lines indicate attachment to the remainder of the moiety or reagent, and —R and —$R^a$ are independently of each other selected from the group consisting of —H, methyl, ethyl, propyl, butyl, pentyl and hexyl.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x+/−10%, preferably x+/−8%, more preferably x+/−5% and most preferably x+/−2%.

As used herein, the term "number average molecular weight" means the ordinary arithmetic mean of the molecular weights of the individual polymers.

As used herein the term "water-soluble" with reference to a carrier means that when such carrier is part of the PTH prodrug of the present invention at least 1 g of the PTH prodrug comprising such water-soluble carrier can be dissolved in one liter of water at 20° C. to form a homogeneous solution. Accordingly, the term "water-insoluble" with reference to a carrier means that when such carrier is part of the PTH prodrug of the present invention less than 1 g of the PTH prodrug comprising such water-insoluble carrier can be dissolved in one liter of water at 20° C. to form a homogeneous solution.

As used herein, the term "hydrogel" means a hydrophilic or amphiphilic polymeric network composed of homopolymers or copolymers, which is insoluble due to the presence of hydrogen bonds, ionic interactions and/or covalent chemical crosslinks. The crosslinks provide the network structure and physical integrity.

As used herein the term "thermogelling" means a compound that is a liquid or a low viscosity solution having a viscosity of less than 500 cps at 25° C. at a shear rate of about 0.1/second at a low temperature, which low temperature ranges between about 0° C. to about 10° C., but which is a higher viscosity compound of less than 10000 cps at 25° C. at a shear rate of about 0.1/second at a higher temperature, which higher temperature ranges between about 30° C. to about 40° C., such as at about 37° C.

As used herein, the term "PEG-based" in relation to a moiety or reagent means that said moiety or reagent comprises PEG. Preferably, a PEG-based moiety or reagent comprises at least 10% (w/w) PEG, such as at least 20% (w/w) PEG, such as at least 30% (w/w) PEG, such as at least 40% (w/w) PEG, such as at least 50% (w/w), such as at least 60 (w/w) PEG, such as at least 70% (w/w) PEG, such as at least 80% (w/w) PEG, such as at least 90% (w/w) PEG, such as at least 95%. The remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

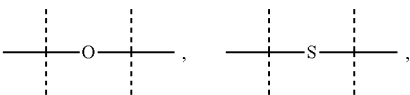

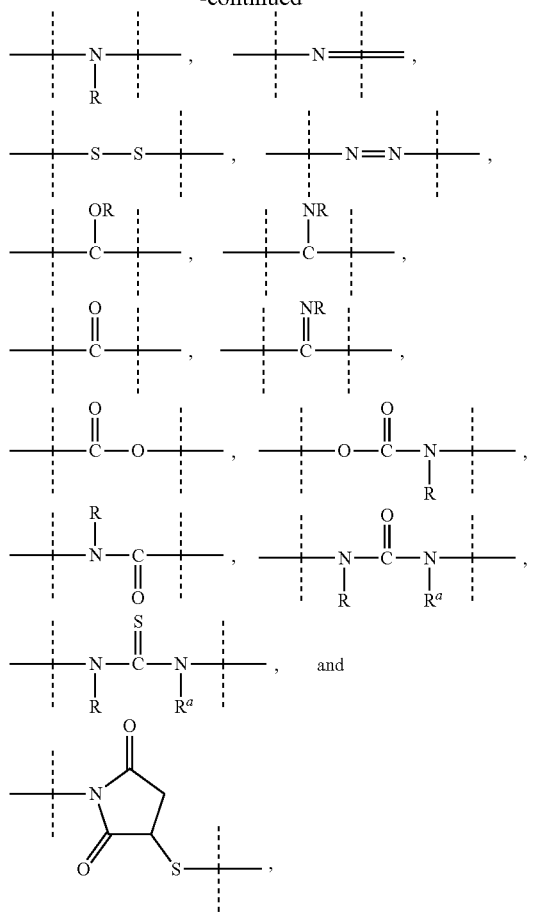

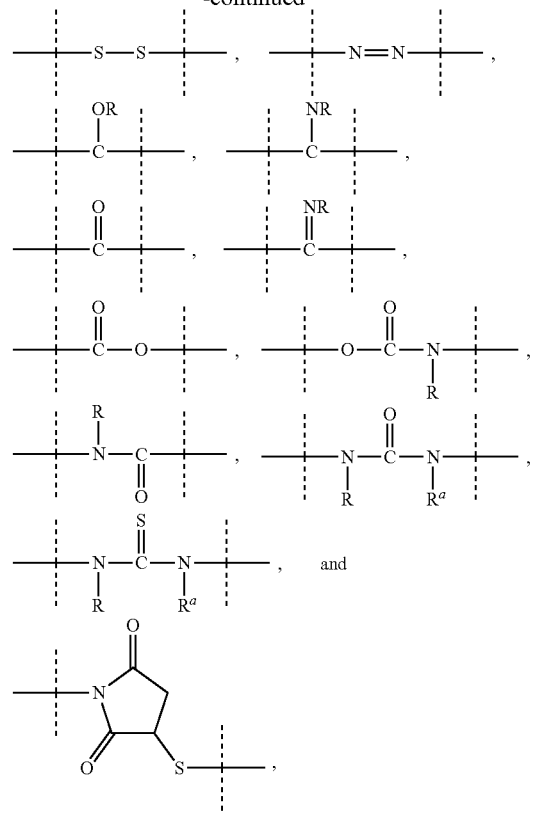

wherein
dashed lines indicate attachment to the remainder of the moiety or reagent, and
—R and —R$^a$ are independently of each other selected from the group consisting of —H, methyl, ethyl, propyl, butyl, pentyl and hexyl.

As used herein, the term "PEG-based comprising at least X % PEG" in relation to a moiety or reagent means that said moiety or reagent comprises at least X % (w/w) ethylene glycol units (—CH$_2$CH$_2$O—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

C$_{1-50}$ alkyl, C$_{2-50}$ alkenyl, C$_{2-50}$ alkynyl, C$_{3-10}$ cycloalkyl, 3- to 10-membered heterocyclyl, 8- to 11-membered heterobicyclyl, phenyl, naphthyl, indenyl, indanyl, and tetralinyl; and
linkages selected from the group comprising

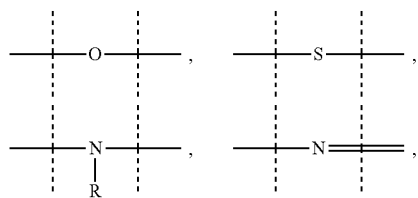

wherein
dashed lines indicate attachment to the remainder of the moiety or reagent, and —R and —R$^a$ are independently of each other selected from the group consisting of —H, methyl, ethyl, propyl, butyl, pentyl and hexyl.

The term "hyaluronic acid-based comprising at least X % hyaluronic acid" is used accordingly.

The term "substituted" as used herein means that one or more —H atom(s) of a molecule or moiety are replaced by a different atom or a group of atoms, which are referred to as "substituent".

Preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^3$)(R$^{x3a}$)—, —N(R$^{x3}$)C(O)N(R$^{x3a}$)—, and —OC(O)N(R$^{x3}$)—;

—R$^{x1}$, —R$^{x1a}$, —R$^{x1b}$ are independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —$R^{x2}$, which are the same or different and wherein $C_{1-50}$ alkyl, $C_{2-50}$ alkenyl, and $C_{2-50}$ alkynyl are optionally interrupted by one or more groups selected from the group consisting of -$T^0$-, —C(O)O—, —O—, —C(O)—, —C(O)N ($R^{x3}$)—, —S(O)$_2$N($R^{x3}$)—, —S(O)N($R^{x3}$)—, —S(O)$_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC(O)N($R^{x3}$)—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$ which are the same or different;

each —$R^{x2}$ is independently selected from the group consisting of halogen, —CN, oxo (=O), —COO$R^{x4}$, —O$R^{x4}$, —C(O)$R^{x4}$, —C(O)N($R^{x4}R^{x4a}$), —S(O)$_2$N ($R^{x4}R^{x4a}$), —S(O)N($R^{x4}R^{x4a}$), —S(O)$_2R^{x4}$, —S(O)$R^{x4}$, —N($R^{x4}$)S(O)$_2$N($R^{x4a}R^{x4b}$), —S$R^{x4}$, —N($R^{x4}R^{x4a}$), —NO$_2$, —OC(O)$R^{x4}$, —N($R^{x4}$)C(O)$R^{x4a}$, —N($R^{x4}$)S(O)$_2R^{x4a}$, —N($R^{x4}$)S(O)$R^{x4a}$, —N($R^{x4}$)C(O)O$R^{x4a}$, —N($R^{x4}$)C(O)N($R^{x4a}R^{x4b}$), —OC(O)N($R^{x4}R^{x4a}$), and $C_{1-6}$ alkyl; wherein $C_{1-6}$ alkyl is optionally substituted with one or more halogen, which are the same or different;

each —$R^{x3}$, —$R^{x3a}$, —$R^{x4}$, —$R^{x4a}$, —$R^{x4b}$ is independently selected from the group consisting of —H and $C_{1-6}$ alkyl; wherein $C_{1-6}$ alkyl is optionally substituted with one or more halogen, which are the same or different.

More preferably, the one or more further optional substituents are independently of each other selected from the group consisting of halogen, —CN, —COO$R^{x1}$, —O$R^{x1}$, —C(O)$R^{x1}$, —C(O)N($R^{x1}R^{x1a}$), —S(O)$_2$N($R^{x1}R^{x1a}$), —S(O)N($R^{x1}R^{x1a}$), —S(O)$_2R^{x1}$, —S(O)$R^{x1}$, —N($R^{x1}$)S (O)$_2$ N($R^{x1a}R^{x1b}$), —S$R^{x1}$, —N($R^{x1}R^{x1a}$), —NO$_2$, —OC(O) $R^{x1}$, —N($R^{x1}$)C(O)$R^{x1a}$, —N($R^{x1}$)S(O)$_2R^{x1a}$, —N($R^{x1}$)S (O)$R^{x1a}$, —N($R^{x1}$)C(O)O$R^{x1a}$, —N($R^{x1}$)C(O)N($R^{x1a}R^{x1b}$), —OC(O)N($R^{x1}R^{x1a}$), -$T^0$, $C_{1-10}$alkyl, $C_{2-10}$ alkenyl, and $C_{2-10}$ alkynyl; wherein -$T^0$, $C_{1-10}$ alkyl, $C_{2-10}$ alkenyl, and $C_{2-10}$ alkynyl are optionally substituted with one or more —$R^{x2}$, which are the same or different and wherein $C_{1-10}$ alkyl, $C_{2-10}$ alkenyl, and $C_{2-10}$ alkynyl are optionally interrupted by one or more groups selected from the group consisting of -$T^0$-, —C(O)O—, —O—, —C(O)—, —C(O) N($R^{x3}$)—, —S(O)$_2$N($R^{x3}$)—, —S(O)N($R^{x3}$)—, —S(O)$_2$—, —S(O)—, —N($R^{x3}$)S(O)$_2$N($R^{x3a}$)—, —S—, —N($R^{x3}$)—, —OC(O$R^3$)($R^{x3a}$)—, —N($R^{x3}$)C(O)N($R^{x3a}$)—, and —OC(O)N($R^{x3}$)—;

each —$R^{x1}$, —$R^{x1a}$, —$R^{x1b}$, —$R^{x3}$, —$R^{x3a}$ is independently selected from the group consisting of —H, halogen, $C_{1-6}$ alkyl, $C_{2-6}$ alkenyl, and $C_{2-6}$ alkynyl;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$ which are the same or different;

each —$R^{x2}$ is independently selected from the group consisting of halogen, —CN, oxo (=O), —COO$R^{x4}$, —O$R^{x4}$, —C(O)$R^{x4}$, —C(O)N($R^{x4}R^{x4a}$), —S(O)$_2$N ($R^{x4}R^{x4a}$), —S(O)N($R^{x4}R^{x4a}$), —S(O)$_2R^{x4}$, —S(O) $R^{x4}$, —N($R^{x4}$)S(O)$_2$N($R^{x4a}R^{x4b}$), —S$R^{x4}$, —N($R^{x4}R^{x4a}$), —NO$_2$, —OC(O)$R^{x4}$, —N($R^{x4}$)C(O) $R^{x4a}$, —N($R^{x4}$)S(O)$_2R^{x4a}$, —N($R^{x4}$)S(O)$R^{x4a}$, —N($R^{x4}$)C(O)O$R^{x4}$a —N($R^{x4}$)C(O)N($R^{x4a}R^{x4b}$), —OC(O)N($R^{x4}R^{x4a}$), and $C_{1-6}$ alkyl; wherein $C_{1-6}$ alkyl is optionally substituted with one or more halogen, which are the same or different;

each —$R^{x4}$, —$R^{x4a}$, —$R^{x4b}$ is independently selected from the group consisting of —H, halogen, $C_{1-6}$ alkyl, $C_{2-6}$ alkenyl, and $C_{2-6}$ alkynyl;

Even more preferably, the one or more further optional substituents are independently of each other selected from the group consisting of halogen, —CN, —COO$R^{x1}$, —O$R^{x1}$, —C(O)$R^{x1}$, —C(O)N($R^{x1}R^{x1a}$), —S(O)$_2$N ($R^{x1}R^{x1a}$), —S(O)$_2$N($R^{x1}R^{x1a}$), —S(O)$_2R^{x1}$, —S(O)$R^{x1}$, —N($R^{x1}$)S(O)$_2$N($R^{x1a}R^{x1b}$), —S$R^{x1}$, —N($R^{x1}R^{x1a}$), —NO$_2$, —OC(O)$R^{x1}$, —N($R^{x1}$)C(O)$R^{x1a}$, —N($R^{x1}$)S(O)$_2$ $R^{x1a}$, —N($R^{x1}$)S(O)$R^{x1a}$, —N($R^{x1}$)C(O)O$R^{x1a}$, —N($R^{x1}$)C (O)N($R^{x1a}R^{x1b}$), —OC(O)N($R^{x1}R^{x1a}$), -$T^0$, $C_{1-6}$ alkyl, $C_{2-6}$ alkenyl, and $C_{2-6}$ alkynyl; wherein -$T^0$, $C_{1-6}$ alkyl, $C_{2-6}$ alkenyl, and $C_{2-6}$ alkynyl are optionally substituted with one or more —$R^{x2}$, which are the same or different and wherein $C_{1-6}$ alkyl, $C_{2-6}$ alkenyl, and $C_{2-6}$ alkynyl are optionally interrupted by one or more groups selected from the group consisting of -$T^0$-, —C(O)O—, —O—, —C(O)—, —C(O) N($R^{x3}$)—, —S(O)$_2$N($R^{x3}$)—, —S(O)N($R^{x3}$)—, —S(O)$_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC (O)N($R^{x3}$)—;

each —$R^{x1}$, —$R^{x1a}$, —$R^{x1b}$, —$R^{x2}$, —$R^{x3}$, —$R^{x3a}$ is independently selected from the group consisting of —H, halogen, $C_{1-6}$ alkyl, $C_{2-6}$ alkenyl, and $C_{2-6}$ alkynyl;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$, which are the same or different.

Preferably, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "interrupted" means that a moiety is inserted between two carbon atoms or—if the insertion is at one of the moiety's ends—between a carbon or heteroatom and a hydrogen atom, preferably between a carbon and a hydrogen atom.

The term "spacer" refers to any moiety that is suitable to connect two moieties. Preferably, a spacer is selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N ($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O) N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC (O)N($R^{y3}$)—;

—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo (═O), —COO$R^{y5}$, —O$R^{y5}$, —C(O)$R^{y5}$, —C(O)N($R^{y5}R^{y5a}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently selected from the group consisting of —H, and $C_{1-6}$ alkyl, wherein $C_{1-6}$ alkyl is optionally substituted with one or more halogen, which are the same or different.

Even more preferably the spacer is selected from -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more —$R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more —$R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

—$R^{y2}$ is selected from the group consisting of halogen, —CN, oxo (═O), —COO$R^{y5}$, —O$R^{y5}$, —C(O)$R^{y5}$, —C(O)N($R^{y5}R^{y5a}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

Even more preferably the spacer is selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen, and $C_{1-6}$ alkyl; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl.

When two moieties of a molecule are linked by the $C_{1-6}$ alkyl group, then examples for such $C_{1-6}$ alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —$CH$=$CH_2$, —$CH$=$CH$—$CH_3$, —$CH_2$—$CH$=$CH_2$, —$CH$=$CHCH_2$—$CH_3$ and —$CH$=$CH$—$CH$=$CH_2$. When two moieties of a molecule are linked by the $C_{2-6}$ alkenyl group, then an example for such $C_{2-6}$ alkenyl is —$CH$=$CH$—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means straight-chain or branched hydrocarbon moiety comprising at least one carbon-carbon triple bond having 2 to 6 carbon atoms. If present at the end of a molecule, examples are —C≡CH, —$CH_2$—C≡CH, $CH_2$—$CH_2$—C≡CH and $CH_2$—C≡C—$CH_3$. When two moieties of a molecule are linked by the alkynyl group, then an example is —C≡C—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkenyl or $C_{2-50}$ alkynyl may optionally be interrupted by one or more moieties which are preferably selected from the group consisting of

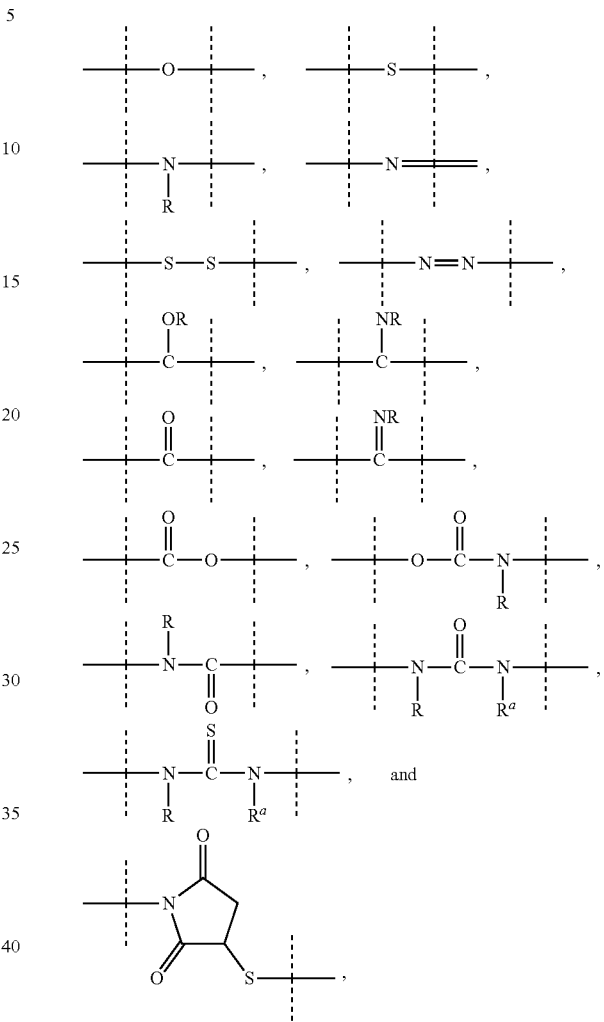

wherein
dashed lines indicate attachment to the remainder of the moiety or reagent; and
—R and —$R^a$ are independently of each other selected from the group consisting of —H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom.

Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

It is understood that the phrase "the pair R$^x$/R$^y$ is joined together with the atom to which they are attached to form a C$_{3-10}$ cycloalkyl or a 3- to 10-membered heterocyclyl" in relation with a moiety of the structure

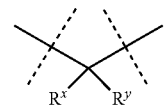

means that Rx and Ry form the following structure:

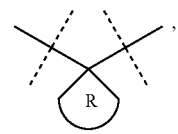

wherein R is C$_{3-10}$ cycloalkyl or 3- to 10-membered heterocyclyl.

It is also understood that the phrase "the pair R$^x$/R$^y$ is joint together with the atoms to which they are attached to form a ring A" in relation with a moiety of the structure

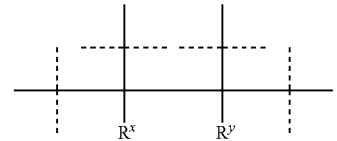

means that R$^x$ and R$^y$ form the following structure:

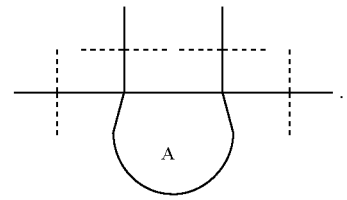

As used herein, the term "terminal alkyne" means a moiety

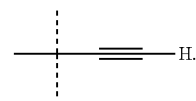

As used herein, "halogen" means fluoro, chloro, bromo or iodo. It is generally preferred that halogen is fluoro or chloro.

In general, the term "comprise" or "comprising" also encompasses "consist of" or "consisting of".

It is understood that in formula (Ia) and (Ib) -D is connected to -L$^1$- via a covalent and reversible linkage.

In another aspect the present invention relates to a PTH prodrug or a pharmaceutically acceptable salt thereof comprising a conjugate D-L, wherein
-D is a PTH moiety; and
-L comprises a reversible prodrug linker moiety -L$^1$-, which moiety -L$^1$- is connected to the PTH moiety -D through a functional group of PTH;
wherein -L$^1$- is substituted with -L$^2$-Z' and is optionally further substituted; wherein
-L$^2$- is a single chemical bond or a spacer moiety; and
—Z' is a water-insoluble carrier moiety.

It is understood that a multitude of moieties -L²-L¹-D is connected to a water-insoluble carrier —Z' and that the linkage between -D and -L¹- is covalent and reversible.

Preferably, -D has the sequence of SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO: 107, SEQ ID NO:108, SEQ ID NO:109, SEQ ID NO:110, SEQ ID NO:111, SEQ ID NO:112, SEQ ID NO:113, SEQ ID NO:114 or SEQ ID NO:115. More preferably -D has the sequence of SEQ ID NO:50, SEQ ID NO:51, SEQ ID NO:52, SEQ ID NO:110, SEQ ID NO:111 or SEQ ID NO:112.

In one embodiment -D has the sequence of SEQ ID NO:50.

In another embodiment -D has the sequence of SEQ ID NO:52.

In another embodiment -D has the sequence of SEQ ID NO:110.

In another embodiment -D has the sequence of SEQ ID NO:111.

In another embodiment -D has the sequence of SEQ ID NO:112.

Most preferably -D has the sequence of SEQ ID NO:51.

The moiety -L¹- is either conjugated to a functional group of the side chain of an amino acid residue of -D, to the N-terminal amine functional group or to the C-terminal carboxyl functional group of -D or to a nitrogen atom in the backbone polypeptide chain of -D. Attachment to either the N-terminus or C-terminus can either be directly through the corresponding amine or carboxyl functional group, respectively, or indirectly wherein a spacer moiety is first conjugated to the amine or carboxyl functional group to which spacer moiety -L¹- is conjugated.

Preferably, the amino acid residue of PTH to which -L¹- is conjugated comprises a functional group selected from the group consisting carboxylic acid, primary and secondary amine, maleimide, thiol, sulfonic acid, carbonate, carbamate, hydroxyl, aldehyde, ketone, hydrazine, isocyanate, isothiocyanate, phosphoric acid, phosphonic acid, haloacetyl, alkyl halide, acryloyl, aryl fluoride, hydroxylamine, sulfate, disulfide, vinyl sulfone, vinyl ketone, diazoalkane, oxirane, guanidine and aziridine. Even more preferably the amino acid residue of PTH to which -L¹- is conjugated comprises a functional group selected from the group consisting hydroxyl, primary and secondary amine and guanidine. Even more preferably the amino acid residue of PTH to which -L¹- is conjugated comprises a primary or secondary amine functional group. Most preferably the amino acid residue of PTH to which -L¹- is conjugated comprises a primary amine functional group.

If the moiety -L¹- is conjugated to a functional group of the side chain of an amino acid residue of PTH said amino acid residue is selected from the group consisting of proteinogenic amino acid residues and non-proteinogenic amino acid residues.

In one embodiment -L¹- is conjugated to a functional group of the side chain of a non-proteinogenic amino acid residue of PTH. It is understood that such non-proteinogenic amino acid is not found in the sequence of native PTH or fragments thereof and that it may only be present in variants, analogs, orthologs, homologs and derivatives of PTH.

In another embodiment -L¹- is conjugated to a functional group of the side chain of a proteinogenic amino acid residue of PTH. Preferably, said amino acid is selected from the group consisting of histidine, lysine, tryptophan, serine, threonine, tyrosine, aspartic acid, glutamic acid and arginine. Even more preferably said amino acid is selected from the group consisting of lysine, aspartic acid, arginine and serine. Even more preferably said amino acid is selected from the group consisting of lysine, arginine and serine.

In one embodiment -L¹- is conjugated to a functional group of the side chain of a histidine of PTH.

In another embodiment -L¹- is conjugated to a functional group of the side chain of a lysine of PTH.

In another embodiment -L¹- is conjugated to a functional group of the side chain of a tryptophan of PTH.

In another embodiment -L¹- is conjugated to a functional group of the side chain of a serine of PTH.

In another embodiment -L¹- is conjugated to a functional group of the side chain of a threonine of PTH.

In another embodiment -L¹- is conjugated to a functional group of the side chain of a tyrosine of PTH. In another embodiment -L¹- is conjugated to a functional group of the side chain of a aspartic acid of PTH.

In another embodiment -L¹- is conjugated to a functional group of the side chain of a glutamic acid of PTH.

In another embodiment -L¹- is conjugated to a functional group of the side chain of an arginine of PTH.

It is understood that not every PTH moiety may comprise all of these amino acid residues.

In a preferred embodiment -L¹- is conjugated to the N-terminal amine functional group of PTH, either directly through the corresponding amine functional group or indirectly wherein a spacer moiety is first conjugated to the amine functional group to which spacer moiety -L¹- is conjugated. Even more preferably, -L¹- is directly conjugated to the N-terminal amine functional group of PTH, preferably PTH 1-34, i.e. PTH having the sequence of SEQ ID NO:51.

It was surprisingly found that N-terminal attachment of -L¹- is advantageous, i.e. attachment of -L¹- to the N-terminus of PTH, because it was found that such attachment site protects the N-terminus which is crucial for PTH activity. Furthermore, it was surprisingly found that the main metabolite formed from a PTH prodrug with N-terminal attachment of -L¹- is PTH 1-33, i.e. the 33 N-terminal amino acids of PTH, which metabolite is known to be active.

In another embodiment -L¹- is conjugated to the C-terminal functional group of PTH, either directly through the corresponding carboxyl functional group or indirectly wherein a spacer moiety is first conjugated to the carboxyl functional group to which spacer moiety -L¹- is conjugated.

Most preferably L¹- is directly conjugated to the N-terminal amine functional group of PTH.

The moiety -L¹- can be connected to -D through any type of linkage, provided that it is reversible. Preferably, -L¹- is connected to -D through a linkage selected from the group consisting of amide, ester, carbamate, acetal, aminal, imine, oxime, hydrazone, disulfide and acylguanidine. Even more preferably -L¹- is connected to -D through a linkage selected from the group consisting of amide, ester, carbamate and acylguanidin. It is understood that some of these linkages per se are not reversible, but that in the present invention neighboring groups comprised in -L¹- render these linkage reversible.

In one embodiment -L¹- is connected to -D through an ester linkage.

In another embodiment -L¹- is connected to -D through a carbamate linkage.

In another embodiment -L¹- is connected to -D through an acylguanidine.

In a preferred embodiment -L¹- is connected to -D through an amide linkage.

The moiety -L$^1$- is a reversible prodrug linker from which the drug, i.e. PTH, is released in its free form, i.e. it is a traceless prodrug linker. Suitable prodrug linkers are known in the art, such as for example the reversible prodrug linker moieties disclosed in WO 2005/099768 A2, WO 2006/136586 A2, WO 2011/089216 A1 and WO 2013/024053 A1, which are incorporated by reference herewith.

In another embodiment -L$^1$- is a reversible prodrug linker as described in WO 2011/012722 A1, WO 2011/089214 A1, WO 2011/089215 A1, WO 2013/024052 A1 and WO 2013/160340 A1 which are incorporated by reference herewith.

A particularly preferred moiety -L$^1$- is disclosed in WO 2009/095479 A2. Accordingly, in a preferred embodiment the moiety -L$^1$- is of formula (II):

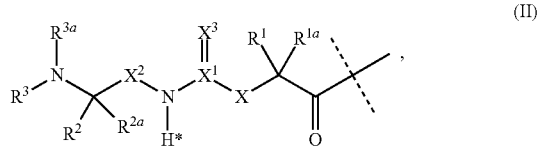

(II)

wherein the dashed line indicates the attachment to a nitrogen, hydroxyl or thiol of -D which is a PTH moiety;

—X— is —C(R$^4$R$^{4a}$)—; —N(R$^4$)—; —O—; —C(R$^4$R$^{4a}$)—C(R$^5$R$^{5a}$)—; —C(R$^5$R$^{5a}$)—C(R$^4$R$^{4a}$)—; —C(R$^4$R$^{4a}$)—N(R$^6$)—; —N(R$^6$)—C(R$^4$R$^{4a}$)—; —C(R$^4$R$^{4a}$)—O—; —O—C(R$^4$R$^{4a}$)—; or —C(R$^7$R$^{7a}$)—;

X$^1$ is C; or S(O);

—X$^2$— is —C(R$^8$R$^{8a}$)—; or —C(R$^8$R$^{8a}$)—C(R$^9$R$^{9a}$)—;

=X$^3$ is =O; =S; or =N—CN;

—R$^1$, —R$^{1a}$, —R$^2$, —R$^{2a}$, —R$^4$, —R$^{4a}$, —R$^5$, —R$^{5a}$, —R$^6$, —R$^8$, —R$^{8a}$, —R$^9$, —R$^{9a}$ are independently selected from the group consisting of —H; and C$_{1-6}$ alkyl;

—R$^3$, —R$^{3a}$ are independently selected from the group consisting of —H; and C$_{1-6}$ alkyl, provided that in case one of —R$^3$, —R$^{3a}$ or both are other than —H they are connected to N to which they are attached through an SP$^3$-hybridized carbon atom;

—R$^7$ is —N(R$^{10}$R$^{10a}$); or —NR$^{10}$—(C=O)—R$^{11}$;

—R$^{7a}$, —R$^{10}$, —R$^{10a}$, —R$^{11}$ are independently of each other —H; or C$_{1-6}$ alkyl; optionally, one or more of the pairs —R$^{1a}$/—R$^{4a}$, —R$^{1a}$/—R$^{5a}$, —R$^{1a}$/—R$^{7a}$, —R$^{4a}$/—R$^{5a}$, —R$^{5a}$/—R$^{9a}$ form a chemical bond;

optionally, one or more of the pairs —R$^1$/—R$^{1a}$, —R$^2$/—R$^{2a}$, —R$^4$/—R$^{4a}$, —R$^5$/—R$^{5a}$, —R$^8$/—R$^{8a}$, —R$^9$/—R$^{9a}$ are joined together with the atom to which they are attached to form a C$_{3-10}$ cycloalkyl; or 3- to 10-membered heterocyclyl;

optionally, one or more of the pairs —R$^1$/—R$^4$, —R$^1$/—R$^5$, —R$^1$/—R$^6$, —R$^1$/—R$^{1a}$, —R$^4$/—R$^5$, —R$^4$/—R$^6$, —R$^8$/—R$^9$, —R$^2$/—R$^3$ are joined together with the atoms to which they are attached to form a ring A;

optionally, R$^3$/R$^{3a}$ are joined together with the nitrogen atom to which they are attached to form a 3- to 10-membered heterocycle;

A is selected from the group consisting of phenyl; naphthyl; indenyl; indanyl; tetralinyl; C$_{3-10}$ cycloalkyl; 3- to 10-membered heterocyclyl; and 8- to 11-membered heterobicyclyl; and wherein -L$^1$- is substituted with -L$^2$-Z or -L$^2$-Z' and wherein -L$^1$- is optionally further substituted, provided that the hydrogen marked with the asterisk in formula (II) is not replaced by -L$^2$-Z or -L$^2$-Z' or a substituent;

wherein

-L$^2$- is a single chemical bond or a spacer;

—Z is a water-soluble carrier; and

Z' is a water-insoluble carrier.

Preferably -L$^1$- of formula (II) is substituted with one moiety -L$^2$-Z or -L$^2$-Z'.

In one embodiment -L$^1$- of formula (II) is not further substituted.

It is understood that if —R$^3$/—R$^{3a}$ of formula (II) are joined together with the nitrogen atom to which they are attached to form a 3- to 10-membered heterocycle, only such 3- to 10-membered heterocycles may be formed in which the atoms directly attached to the nitrogen are SP$^3$-hybridized carbon atoms. In other words, such 3- to 10-membered heterocycle formed by —R$^3$/—R$^{3a}$ together with the nitrogen atom to which they are attached has the following structure:

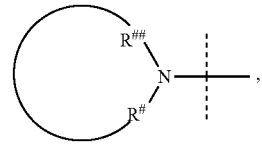

wherein the dashed line indicates attachment to the rest of -L$^1$-;

the ring comprises 3 to 10 atoms comprising at least one nitrogen; and

R$^\#$ and R$^{\#\#}$ represent an SP$^3$-hydridized carbon atom.

It is also understood that the 3- to 10-membered heterocycle may be further substituted.

Exemplary embodiments of suitable 3- to 10-membered heterocycles formed by —R$^3$/—R$^{3a}$ of formula (II) together with the nitrogen atom to which they are attached are the following:

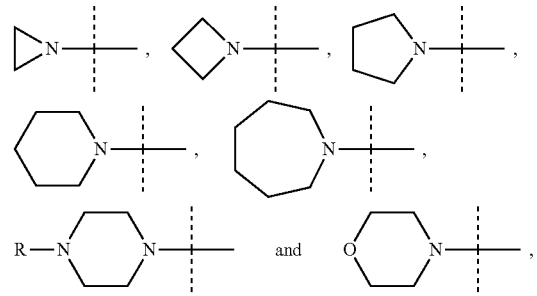

wherein dashed lines indicate attachment to the rest of the molecule; and

—R is selected from the group consisting of —H and C$_{1-6}$ alkyl.

-L$^1$- of formula (II) may optionally be further substituted. In general, any substituent may be used as far as the cleavage principle is not affected, i.e. the hydrogen marked with the asterisk in formula (II) is not replaced and the nitrogen of the moiety

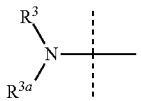

of formula (II) remains part of a primary, secondary or tertiary amine, i.e. —$R^3$ and —$R^{3a}$ are independently of each other —H or are connected to —N< through an $SP^3$-hybridized carbon atom.

In one embodiment —$R^1$ or —$R^{1a}$ of formula (II) is substituted with -$L^2$-Z or -$L^2$-Z'. In another embodiment —$R^2$ or —$R^{2a}$ of formula (II) is substituted with -$L^2$-Z or -$L^2$-Z'. In another embodiment —$R^3$ or —$R^{3a}$ of formula (II) is substituted with -$L^2$-Z or -$L^2$-Z'. In another embodiment —$R^4$ of formula (II) is substituted with -$L^2$-Z or -$L^2$-Z'. In another embodiment —$R^5$ or —$R^{5a}$ of formula (II) is substituted with -$L^2$-Z or -$L^2$-Z'. In another embodiment —$R^6$ of formula (II) is substituted with -$L^2$-Z or -$L^2$-Z'. In another embodiment —$R^7$ or —$R^{7a}$ of formula (II) is substituted with -$L^2$-Z or -$L^2$-Z'. In another embodiment —$R^8$ or —$R^{8a}$ of formula (II) is substituted with -$L^2$-Z or -$L^2$-Z'. In another embodiment —$R^9$ or —$R^{9a}$ of formula (II) is substituted with -$L^2$-Z or -$L^2$-Z'. In another embodiment —$R^{10}$ is substituted with -$L^2$-Z or -$L^2$-Z'. In another embodiment —$R^{11}$ is substituted with -$L^2$-Z or -$L^2$-Z'.

Preferably, —X— of formula (II) is selected from the group consisting of —C($R^4R^{4a}$)—, —N($R^4$)— and —C($R^7R^{7a}$)—.

In one embodiment —X— of formula (II) is —C($R^4R^{4a}$)—.

In one preferred embodiment —X— of formula (II) is —C($R^7R^{7a}$)—.

Preferably, —$R^7$ of formula (II) is —$NR^{10}$—(C=O)—$R^{11}$.

Preferably, —$R^{7a}$ of formula (II) is selected from —H, methyl and ethyl. Most preferably —$R^{7a}$ of formula (II) is —H.

Preferably, —$R^{10}$ is selected from —H, methyl and ethyl. Most preferably —$R^{10}$ is methyl. Preferably, —$R^{11}$ is selected from —H, methyl and ethyl. Most preferably —$R^{11}$ is —H.

Preferably, —$R^{11}$ is substituted with -$L^2$-Z or -$L^2$-Z'.

In another preferred embodiment —X— of formula (II) is —N($R^4$)—.

Preferably, —$R^4$ is selected from the group consisting of —H, methyl and ethyl. Preferably, —$R^4$ is —H.

Preferably, $X^1$ of formula (II) is C.

Preferably, =$X^3$ of formula (II) is =O.

Preferably, —$X^2$— of formula (II) is —C($R^8R^{8a}$)—.

Preferably —$R^8$ and —$R^{8a}$ of formula (II) are independently selected from the group consisting of —H, methyl and ethyl. More preferably at least one of —$R^8$ and —$R^{8a}$ of formula (II) is —H. Even more preferably both —$R^8$ and —$R^{8a}$ of formula (II) are —H.

Preferably, —$R^1$ and —$R^{1a}$ of formula (II) are independently selected from the group consisting of —H, methyl and ethyl.

In one preferred embodiment at least one of —$R^1$ and —$R^{1a}$ of formula (II) is —H, more preferably both —$R^1$ and —$R^{1a}$ of formula (II) are —H.

In another preferred embodiment at least one of —$R^1$ and —$R^{1a}$ of formula (II) is methyl, more preferably both —$R^1$ and —$R^{1a}$ of formula (II) are methyl.

Preferably, —$R^2$ and —$R^{2a}$ of formula (II) are independently selected from the group consisting of —H, methyl and ethyl. More preferably, at least one of —$R^2$ and —$R^{2a}$ of formula (II) is —H. Even more preferably both —$R^2$ and —$R^{2a}$ of formula (II) are H.

Preferably, —$R^3$ and —$R^{3a}$ of formula (II) are independently selected from the group consisting of —H, methyl, ethyl, propyl and butyl.

In one preferred embodiment at least one of —$R^3$ and —$R^{3a}$ of formula (II) is methyl, more preferably —$R^3$ of formula (II) is methyl and —$R^{3a}$ of formula (II) is —H.

In another preferred embodiment —$R^3$ and —$R^{3a}$ of formula (II) are both —H.

Preferably, -D is connected to -$L^1$- through a nitrogen by forming an amide bond.

In one preferred embodiment the moiety -$L^1$- is of formula (IIa-i):

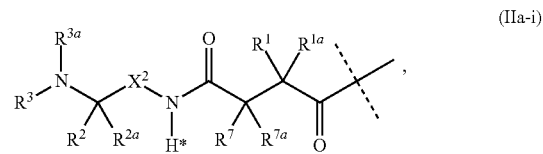

wherein
the dashed line indicates the attachment to a nitrogen of -D which is a PTH moiety by forming an amide bond;
—$R^1$, —$R^{1a}$, —$R^2$, —$R^{2a}$, —$R^3$, —$R^{3a}$, —$R^7$, —$R^{7a}$ and —$X^2$— are used as defined in formula (II); and
wherein -$L^1$- is substituted with -$L^2$-Z or -$L^2$-Z' and wherein -$L^1$- is optionally further substituted, provided that the hydrogen marked with the asterisk in formula (IIa-i) is not replaced by -$L^2$-Z or -$L^2$-Z' or a substituent.

Preferably -$L^1$- of formula (IIa-i) is substituted with one moiety -$L^2$-Z or -$L^2$-Z'.

Preferably the moiety -$L^1$- of formula (IIa-i) is not further substituted. Preferably, —$R^1$ and —$R^{1a}$ of formula (IIa-i) are independently selected from the group consisting of —H, methyl and ethyl. More preferably, at least one of —$R^1$ and —$R^{1a}$ of formula (IIa-i) is —H.

Even more preferably both —$R^1$ and —$R^{1a}$ of formula (IIa-i) are —H.

Preferably, —$R^7$ of formula (IIa-i) is —$NR^{10}$—(C=O)—$R^{11}$.

Preferably, —$R^{7a}$ of formula (II-i) is selected from —H, methyl and ethyl. Most preferably —$R^{7a}$ of formula (II-i) is —H.

Preferably, —$R^{10}$ of formula (IIa-i) is selected from —H, methyl and ethyl. Most preferably —$R^{10}$ of formula (IIa-i) is methyl.

Preferably, —$R^{11}$ of formula (IIa-i) is selected from —H, methyl and ethyl. Most preferably —$R^{11}$ of formula (IIa-i) is —H.

Preferably, —$R^{11}$ of formula (IIa-i) is substituted with -$L^2$-Z or -$L^2$-Z'.

Preferably, —$X^2$— of formula (IIa-i) is —C($R^8R^{8a}$)—.

Preferably —$R^8$ and —$R^{8a}$ of formula (IIa-i) are independently selected from the group consisting of —H, methyl and ethyl. More preferably at least one of —$R^8$ and —$R^{8a}$ of formula (IIa-i) is —H.

Even more preferably both —$R^8$ and —$R^{8a}$ of formula (IIa-i) are —H.

Preferably, —$R^2$ and —$R^{2a}$ of formula (IIa-i) are independently selected from the group consisting of —H, methyl and ethyl. More preferably, at least one of —$R^2$ and —$R^{2a}$ of formula (IIa-i) is —H. Even more preferably both —$R^2$ and —$R^{2a}$ of formula (IIa-i) are H.

Preferably, —$R^3$ and —$R^{3a}$ of formula (IIa-i) are independently selected from the group consisting of —H, methyl, ethyl, propyl and butyl. Even more preferably at least one of —$R^3$ and —$R^{3a}$ of formula (IIa-i) is methyl.

Preferably, —$R^3$ of formula (IIa-i) is —H and —$R^{3a}$ of formula (IIa-i) is methyl.

More preferably the moiety -$L^1$- is of formula (IIa-ii):

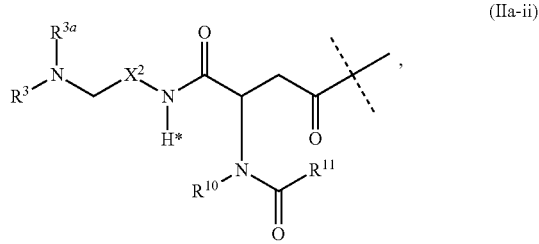

(IIa-ii)

wherein the dashed line indicates the attachment to a nitrogen of -D which is a PTH moiety by forming an amide bond;
—$R^2$, —$R^{2a}$, —$R^{10}$, —$R^{11}$ and —$X^2$— are used as defined in formula (II); and
wherein -$L^1$- is substituted with -$L^2$-Z or -$L^2$-Z' and wherein -$L^1$- is optionally further substituted, provided that the hydrogen marked with the asterisk in formula (IIa-ii) is not replaced by -$L^2$-Z or -$L^2$-Z' or a substituent.

Preferably -$L^1$- of formula (IIa-ii) is substituted with one moiety -$L^2$-Z or -$L^2$-Z'.

Preferably the moiety -$L^1$- of formula (IIa-ii) is not further substituted.

Preferably, —$X^2$— of formula (IIa-ii) is —$C(R^8R^{8a})$—.

Preferably —$R^8$ and —$R^{8a}$ of formula (IIa-ii) are independently selected from the group consisting of —H, methyl and ethyl. More preferably at least one of —$R^8$ and —$R^{8a}$ of formula (IIa-ii) is —H.

Even more preferably both —$R^8$ and —$R^{8a}$ of formula (IIa-ii) are —H.

Preferably, —$R^3$ and —$R^{3a}$ of formula (IIa-ii) are independently selected from the group consisting of —H, methyl, ethyl, propyl and butyl. Even more preferably at least one of —$R^3$ and —$R^{3a}$ of formula (IIa-ii) is methyl.

Preferably, —$R^3$ of formula (IIa-ii) is —H and —$R^{3a}$ of formula (IIa-ii) is methyl.

Preferably, —$R^{10}$ of formula (IIa-ii) is selected from —H, methyl and ethyl. Most preferably —$R^{10}$ of formula (IIa-ii) is methyl.

Preferably, —$R^{11}$ of formula (IIa-ii) is selected from —H, methyl and ethyl. Most preferably —$R^{11}$ of formula (IIa-ii) is —H.

Preferably, —$R^{11}$ of formula (IIa-ii) is substituted with -$L^2$-Z or -$L^2$-Z'.

In an even more preferred embodiment the moiety -$L^1$- is of formula (IIa-ii'):

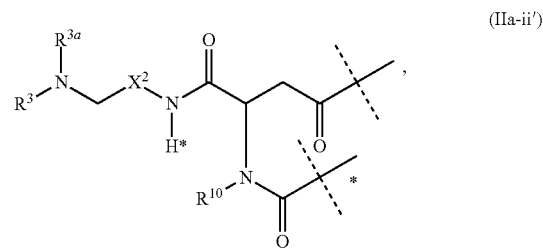

(IIa-ii')

wherein
wherein the dashed line indicates the attachment to a nitrogen of D which is a PTH moiety by forming an amide bond; the dashed line marked with the asterisk indicates attachment to -$L^2$-;
—$R^3$, —$R^{3a}$, —$R^{10}$ and —$X^2$— are used as defined in formula (II); and
wherein -$L^1$- is optionally further substituted, provided that the hydrogen marked with the asterisk in formula (IIa-ii') is not replaced by a substituent.

Preferably the moiety -$L^1$- of formula (IIa-ii') is not further substituted.

Preferably, —$X^2$— of formula (IIa-ii') is —$C(R^8R^{8a})$—.

Preferably —$R^8$ and —$R^{8a}$ of formula (IIa-ii') are independently selected from the group consisting of —H, methyl and ethyl. More preferably at least one of —$R^8$ and —$R^{8a}$ of formula (IIa-ii') is —H. Even more preferably both —$R^8$ and —$R^{8a}$ of formula (IIa-ii') are —H.

Preferably, —$R^3$ and —$R^{3a}$ of formula (IIa-ii') are independently selected from the group consisting of —H, methyl, ethyl, propyl and butyl. Even more preferably at least one of —$R^3$ and —$R^{3a}$ of formula (IIa-ii') is methyl.

Preferably, —$R^3$ of formula (IIa-ii') is —H and —$R^{3a}$ of formula (IIa-ii') is methyl.

Preferably, —$R^{10}$ of formula (IIa-ii') is selected from —H, methyl and ethyl. Most preferably —$R^{10}$ of formula (IIa-ii') is methyl.

Even more preferably the moiety -$L^1$- is of formula (IIa-iii):

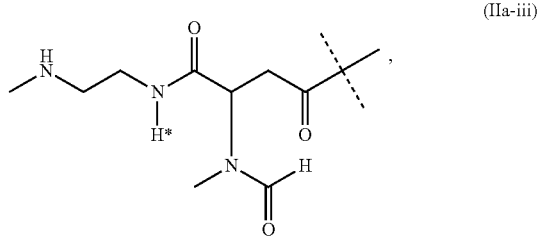

(IIa-iii)

wherein the dashed line indicates the attachment to a nitrogen of -D which is a PTH moiety by forming an amide bond; and
wherein -$L^1$- is substituted with -$L^2$-Z or -$L^2$-Z' and wherein -$L^1$- is optionally further substituted, provided that the hydrogen marked with the asterisk in formula (IIa-iii) is not replaced by -$L^2$-Z or -$L^2$-Z' or a substituent.

Preferably -$L^1$- of formula (IIa-iii) is substituted with one moiety -$L^2$-Z or -$L^2$-Z'.

Preferably the moiety -$L^1$- of formula (IIa-iii) is not further substituted.

Most preferably the moiety -L$^1$- is of formula (IIa-iii'):

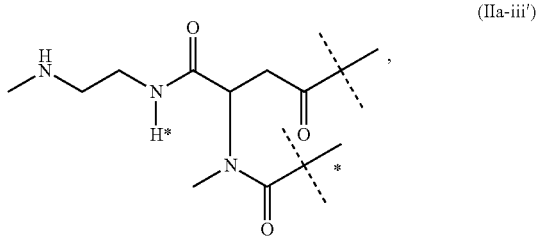

(IIa-iii')

wherein
wherein the dashed line indicates the attachment to a nitrogen of D which is a PTH moiety by forming an amide bond;
the dashed line marked with the asterisk indicates attachment to -L$^2$-;
—R$^2$, —R$^{2a}$, —R$^3$, —R$^{3a}$ and —X$^2$— are used as defined in formula (II); and
wherein -L$^1$- is optionally further substituted, provided that the hydrogen marked with the asterisk in formula (IIa-iii') is not replaced by a substituent.

Preferably the moiety -L$^1$- of formula (IIa-iii') is not further substituted.

In another preferred embodiment the moiety -L$^1$- is of formula (IIb-i)

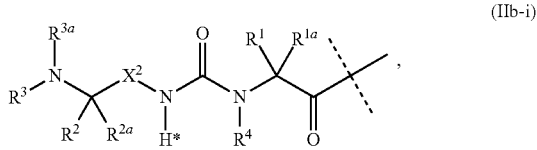

(IIb-i)

wherein
the dashed line indicates the attachment to a nitrogen of -D which is a PTH moiety by forming an amide bond;
—R$^1$, —R$^{1a}$, —R$^2$, —R$^{2a}$, —R$^3$, —R$^{3a}$, —R$^4$ and —X$^2$— are used as defined in formula (II); and
wherein -L$^1$- is substituted with -L$^2$-Z or -L$^2$-Z' and wherein -L$^1$- is optionally further substituted, provided that the hydrogen marked with the asterisk in formula (IIb-i) is not replaced by -L$^2$-Z or -L$^2$-Z' or a substituent.

Preferably -L$^1$- of formula (IIb-i) is substituted with one moiety -L$^2$-Z or -L$^2$-Z'.

Preferably the moiety -L$^1$- of formula (IIb-i) is not further substituted.

Preferably, —R$^1$ and —R$^{1a}$ of formula (IIb-i) are independently selected from the group consisting of —H, methyl and ethyl. More preferably, at least one of —R$^1$ and —R$^{1a}$ of formula (IIb-i) is methyl. Even more preferably both —R$^1$ and —R$^{1a}$ of formula (IIb-i) are methyl.

Preferably, —R$^4$ of formula (IIb-i) is selected from the group consisting of —H, methyl and ethyl.

More preferably, —R$^4$ of formula (IIb-i) is —H.

Preferably, —X$^2$— of formula (IIb-i) is —C(R$^8$R$^{8a}$)—.

Preferably —R$^8$ and —R$^{8a}$ of formula (IIb-i) are independently selected from the group consisting of —H, methyl and ethyl. More preferably at least one of —R$^8$ and —R$^{8a}$ of formula (IIb-i) is —H.

Even more preferably both —R$^8$ and —R$^{8a}$ of formula (IIb-i) are —H.

Preferably, —R$^2$ and —R$^{2a}$ of formula (IIb-i) are independently selected from the group consisting of —H, methyl and ethyl. More preferably, at least one of —R$^2$ and —R$^{2a}$ of formula (IIb-i) is —H.

Even more preferably both —R$^2$ and —R$^{2a}$ of formula (IIb-i) are H.

Preferably, —R$^3$ and —R$^{3a}$ of formula (IIb-i) are independently selected from the group consisting of —H, methyl, ethyl, propyl and butyl. Even more preferably at least one of —R$^3$ and —R$^{3a}$ of formula (IIb-i) is —H. Even more preferably both —R$^3$ and —R$^{3a}$ of formula (IIb-i) are —H.

More preferably the moiety -L$^1$- is of formula (IIb-ii):

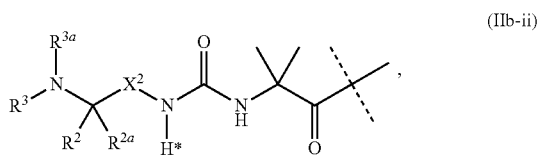

(IIb-ii)

wherein the dashed line indicates the attachment to a nitrogen of -D which is a PTH moiety by forming an amide bond;
—R$^2$, —R$^{2a}$, —R$^3$, —R$^{3a}$ and —X$^2$— are used as defined in formula (II); and
wherein -L$^1$- is substituted with -L$^2$-Z or -L$^2$-Z' and wherein -L$^1$- is optionally further substituted, provided that the hydrogen marked with the asterisk in formula (IIb-ii) is not replaced by -L$^2$-Z or -L$^2$-Z' or a substituent.

Preferably -L$^1$- of formula (IIb-ii) is substituted with one moiety -L$^2$-Z or -L$^2$-Z'.

Preferably the moiety -L$^1$- of formula (IIb-ii) is not further substituted.

Preferably, —X$^2$— of formula (IIb-ii) is —C(R$^8$R$^{8a}$)—.

Preferably —R$^8$ and —R$^{8a}$ of formula (IIb-ii) are independently selected from the group consisting of —H, methyl and ethyl. More preferably at least one of —R$^8$ and —R$^{8a}$ of formula (IIb-ii) is —H. Even more preferably both —R$^8$ and —R$^{8a}$ of formula (IIb-ii) are —H.

Preferably, —R$^2$ and —R$^{2a}$ of formula (IIb-ii) are independently selected from the group consisting of —H, methyl and ethyl. More preferably, at least one of —R$^2$ and —R$^{2a}$ of formula (IIb-ii) is —H. Even more preferably both —R$^2$ and —R$^{2a}$ of formula (IIb-ii) are H.

Preferably, —R$^3$ and —R$^{3a}$ of formula (IIb-ii) are independently selected from the group consisting of —H, methyl, ethyl, propyl and butyl. Even more preferably at least one of —R$^3$ and —R$^{3a}$ of formula (IIb-ii) is —H. Even more preferably both —R$^3$ and —R$^{3a}$ of formula (IIb-ii) are —H.

Even more preferably the moiety -L$^1$- is of formula (IIb-ii'):

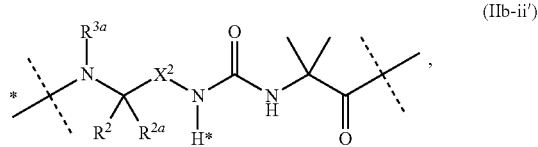

(IIb-ii')

wherein
the dashed line indicates the attachment to a nitrogen of -D which is a PTH moiety by forming an amide bond;
$R^2$, $-R^{2a}$, $-R^3$, $-R^{3a}$ and $-X^2-$ are used as defined in formula (II); and
wherein -$L^1$- is substituted with -$L^2$-Z or -$L^2$-Z' and wherein -$L^1$- is optionally further substituted, provided that the hydrogen marked with the asterisk in formula (IIb-ii') is not replaced by -$L^2$-Z or -$L^2$-Z' or a substituent.

Preferably the moiety -$L^1$- of formula (IIb-ii') is not further substituted.

Preferably, $-X^2-$ of formula (IIb-ii') is $-C(R^8R^{8a})-$.

Preferably $-R^8$ and $-R^{8a}$ of formula (IIb-ii') are independently selected from the group consisting of $-H$, methyl and ethyl. More preferably at least one of $-R^8$ and $-R^{8a}$ of formula (IIb-ii') is $-H$. Even more preferably both $-R^8$ and $-R^{8a}$ of formula (IIb-ii') are $-H$.

Preferably, $-R^2$ and $-R^{2a}$ of formula (IIb-ii') are independently selected from the group consisting of $-H$, methyl and ethyl. More preferably, at least one of $-R^2$ and $-R^{2a}$ of formula (IIb-ii') is $-H$. Even more preferably both $-R^2$ and $-R^{2a}$ of formula (IIb-ii') are H.

Preferably, $-R^3$ and $-R^{3a}$ of formula (IIb-ii') are independently selected from the group consisting of $-H$, methyl, ethyl, propyl and butyl. Even more preferably at least one of $-R^3$ and $-R^{3a}$ of formula (IIb-ii') is $-H$. Even more preferably both $-R^3$ and $-R^{3a}$ of formula (IIb-ii') are $-H$.

Even more preferably the moiety -$L^1$- is of formula (IIb-iii):

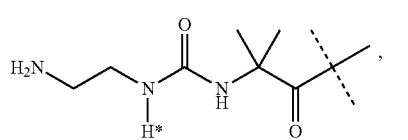

(IIb-iii)

wherein
the dashed line indicates the attachment to a nitrogen of -D which is a PTH moiety by forming an amide bond; and
wherein -$L^1$- is substituted with -$L^2$-Z or -$L^2$-Z' and wherein -$L^1$- is optionally further substituted, provided that the hydrogen marked with the asterisk in formula (IIb-iii) is not replaced by -$L^2$-Z or -$L^2$-Z' or a substituent.

Preferably -$L^1$- of formula (IIb-iii) is substituted with one moiety -$L^2$-Z or -$L^2$-Z'.

Preferably the moiety -$L^1$- of formula (IIb-iii) is not further substituted.

Most preferably the moiety -$L^1$- is of formula (IIb-iii'):

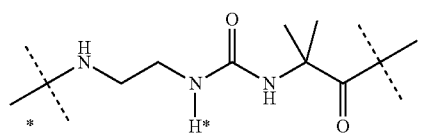

(IIb-iii')

wherein
the dashed line indicates the attachment to a nitrogen of -D which is a PTH moiety by forming an amide bond;

$-R^2$, $-R^{2a}$, $-R^3$, $-R^{3a}$ and $-X^2-$ are used as defined in formula (II); and
wherein -$L^1$- is substituted with -$L^2$-Z or -$L^2$-Z' and wherein -$L^1$- is optionally further substituted, provided that the hydrogen marked with the asterisk in formula (IIb-iii') is not replaced by -$L^2$-Z or -$L^2$-Z' or a substituent.

Preferably the moiety -$L^1$- of formula (IIb-iii') is not further substituted.

Another preferred moiety -$L^1$- is disclosed in unpublished European patent application 14180004, which corresponds to the international application with the application number PCT/EP2015/067929. Accordingly, in another preferred embodiment the moiety -$L^1$- is of formula (III):

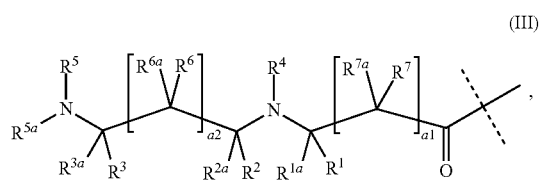

(III)

wherein
the dashed line indicates attachment to a primary or secondary amine or hydroxyl of -D which is a PTH moiety by forming an amide or ester linkage, respectively;
$-R^1$, $-R^{1a}$, $-R^2$, $-R^{2a}$, $-R^3$ and $-R^{3a}$ are independently of each other selected from the group consisting of $-H$, $-C(R^8R^{8a}R^{8b})$, $-C(=O)R^8$, $-C\equiv N$, $-C(=NR^8)R^{8a}$, $-CR^8(=CR^{8a}R^{8b})$, $-C\equiv CR^8$ and -T;
$-R^4$, $-R^5$ and $-R^{5a}$ are independently of each other selected from the group consisting of $-H$, $-C(R^9R^{9a}R^{9b})$ and -T;
a1 and a2 are independently of each other 0 or 1;
each $-R^6$, $-R^{6a}$, $-R^7$, $-R^{7a}$, $-R^8$, $-R^{8a}$, $-R^{8b}$, $-R^9$ $-R^{9a}$, $-R^{9b}$ are independently of each other selected from the group consisting of $-H$, halogen, $-CN$, $-COOR^{10}$, $-OR^{10}$, $-C(O)R^{10}$, $-C(O)N(R^{10}R^{10a})$, $-S(O)_2N(R^{10}R^{10a})$, $-S(O)N(R^{10}R^{10a})$, $-S(O)_2R^{10}$, $-S(O)R^{10}$, $-N(R^{10})S(O)_2N(R^{10a}R^{10b})$, $-SR^{10}$, $-N(R^{10}R^{10a})$, $-NO_2$, $-OC(O)R^{10}$, $-N(R^{10})C(O)R^{10a}$, $-N(R^{10})S(O)_2R^{10a}$, $-N(R^{10})S(O)R^{10a}$, $-N(R^{10})C(O)OR^{10a}$, $-N(R^{10})C(O)N(R^{10a}R^{10b})$, $-OC(O)N(R^{10}R^{10a})$, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more $-R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, $-C(O)O-$, $-O-$, $-C(O)-$, $-C(O)N(R^{12})-$, $-S(O)_2N(R^{12})-$, $-S(O)N(R^{12})-$, $-S(O)_2-$, $-S(O)-$, $-N(R^{12})S(O)_2N(R^{12a})-$, $-S-$, $-N(R^{12})-$, $-OC(OR^{12})(R^{12a})-$, $-N(R^{12})C(O)N(R^{12a})-$, and $-OC(O)N(R^{12})-$;
each $-R^{10}$, $-R^{10a}$, $-R^{10b}$ is independently selected from the group consisting of $-H$, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more $-R^{11}$, which are the same or different and wherein $C_{1-20}$ alkyl, $C_{2-20}$ alkenyl, and $C_2$-20 alkynyl are optionally interrupted by one or more groups selected from the group consisting of -T-, —C(O)O—, —O—, —C(O)—, —C(O)N($R^{12}$)—, —S(O)$_2$N($R^{12}$)—, —S(O)N($R^{12}$)—, —S(O)$_2$—, —S(O)—, —N($R^{12}$)S(O)$_2$N($R^{12a}$)—, —S—, —N($R^{12}$)—, —OC(O$R^{12}$)($R^{12a}$)—, —N($R^{12}$)C(O)N($R^{12a}$)—, and —OC(O)N($R^{12}$)—;

each T is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T is independently optionally substituted with one or more —$R^{11}$, which are the same or different;

each —$R^{11}$ is independently of each other selected from halogen, —CN, oxo (=O), —COO$R^{13}$, —O$R^{13}$, —C(O)$R^{13}$, —C(O)N($R^{13}R^{13a}$), —S(O)$_2$N($R^{13}R^{13a}$), —S(O)N($R^{13}R^{13a}$), —S(O)$_2R^{13}$, —S(O)$R^{13}$, —N($R^{13}$)S(O)$_2$N($R^{13a}R^{13b}$), —S$R^{13}$, —N($R^{13}R^{13a}$), —NO$_2$, —OC(O)$R^{13}$, —N($R^{13}$)C(O)$R^{13a}$, —N($R^{13}$)S(O)$_2R^{13a}$, —N($R^{13}$)S(O)$R^{13a}$, —N($R^{13}$)C(O)O$R^{13a}$, —N($R^{13}$)C(O)N($R^{13a}R^{13b}$), —OC(O)N($R^{13}R^{13a}$), and $C_{1-6}$ alkyl; wherein $C_{1-6}$ alkyl is optionally substituted with one or more halogen, which are the same or different;

each —$R^{12}$, —$R^{12a}$, —$R^{13}$, —$R^{13a}$, —$R^{13b}$ is independently selected from the group consisting of —H, and $C_{1-6}$ alkyl; wherein $C_{1-6}$ alkyl is optionally substituted with one or more halogen, which are the same or different;

optionally, one or more of the pairs —$R^1$/—$R^{1a}$, —$R^2$/—$R^{2a}$, —$R^3$/—$R^{3a}$, —$R^6$/—$R^{6a}$, —$R^7$/—$R^{7a}$ are joined together with the atom to which they are attached to form a $C_{3-10}$ cycloalkyl or a 3- to 10-membered heterocyclyl;

optionally, one or more of the pairs —$R^1$/—$R^2$, —$R^1$/—$R^3$, —$R^1$/—$R^4$, —$R^1$/—$R^5$, —$R^1$/—$R^6$, —$R^1$/—$R^7$, —$R^2$/—$R^3$, —$R^2$/—$R^4$, —$R^2$/—$R^5$, —$R^2$/—$R^6$, —$R^2$/—$R^7$, —$R^3$/—$R^4$, —$R^3$/—$R^5$, —$R^3$/—$R^6$, —$R^3$/—$R^7$, —$R^4$/—$R^5$, —$R^4$/—$R^6$, —$R^4$/—$R^7$, —$R^5$/—$R^6$, —$R^5$/—$R^7$, —$R^6$/—$R^7$ are joint together with the atoms to which they are attached to form a ring A;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl;

wherein -$L^1$- is substituted with -$L^2$-Z or -$L^2$-Z' and wherein -$L^1$- is optionally further substituted;
wherein
-$L^2$- is a single chemical bond or a spacer;
—Z is a water-soluble carrier; and
—Z' is a water-insoluble carrier.

The optional further substituents of -$L^1$- of formula (III) are preferably as described above.

Preferably -$L^1$- of formula (III) is substituted with one moiety -$L^2$-Z or -$L^2$-Z'.

In one embodiment -$L^1$- of formula (III) is not further substituted.

Additional preferred embodiments for -$L^1$- are disclosed in EP1536334B1, WO2009/009712A1, WO2008/034122A1, WO2009/143412A2, WO2011/082368A2, and U.S. Pat. No. 8,618,124B2, which are herewith incorporated by reference in their entirety.

Additional preferred embodiments for -$L^1$- are disclosed in U.S. Pat. No. 8,946,405B2 and U.S. Pat. No. 8,754,190B2, which are herewith incorporated by reference in their entirety. Accordingly, a preferred moiety -$L^1$- is of formula (IV):

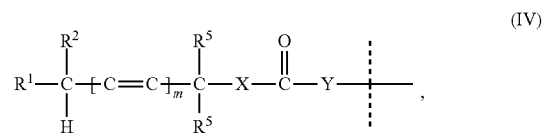

wherein
the dashed line indicates attachment to -D which is a PTH moiety and wherein attachment is through a functional group of -D selected from the group consisting of —OH, —SH and —NH$_2$;
m is 0 or 1;
at least one or both of —$R^1$ and —$R^2$ is/are independently of each other selected from the group consisting of —CN, —NO$_2$, optionally substituted aryl, optionally substituted heteroaryl, optionally substituted alkenyl, optionally substituted alkynyl, —C(O)$R^3$, —S(O)$R^3$, —S(O)$_2R^3$, and —S$R^4$,
one and only one of —$R^1$ and —$R^2$ is selected from the group consisting of —H, optionally substituted alkyl, optionally substituted arylalkyl, and optionally substituted heteroarylalkyl;
—$R^3$ is selected from the group consisting of —H, optionally substituted alkyl, optionally substituted aryl, optionally substituted arylalkyl, optionally substituted heteroaryl, optionally substituted heteroarylalkyl, —O$R^9$ and —N($R^9$)$_2$;
—$R^4$ is selected from the group consisting of optionally substituted alkyl, optionally substituted aryl, optionally substituted arylalkyl, optionally substituted heteroaryl, and optionally substituted heteroarylalkyl;
each —$R^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;
—$R^9$ is selected from the group consisting of —H and optionally substituted alkyl;
—Y— is absent and —X— is —O— or —S—; or
—Y— is —N(Q)CH$_2$— and —X— is —O—;
Q is selected from the group consisting of optionally substituted alkyl, optionally substituted aryl, optionally substituted arylalkyl, optionally substituted heteroaryl and optionally substituted heteroarylalkyl;
optionally, —$R^1$ and —$R^2$ may be joined to form a 3 to 8-membered ring; and
optionally, both —$R^9$ together with the nitrogen to which they are attached form a heterocyclic ring;
wherein -$L^1$- is substituted with -$L^2$-Z or -$L^2$-Z' and wherein -$L^1$- is optionally further substituted;
wherein
-$L^2$- is a single chemical bond or a spacer;
—Z is a water-soluble carrier; and
—Z' is a water-insoluble carrier.

Only in the context of formula (IV) the terms used have the following meaning: The term "alkyl" as used herein includes linear, branched or cyclic saturated hydrocarbon groups of 1 to 8 carbons, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, preferably 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, or an additional ring, each optionally further substituted.

Optional substituents on any group, including the above, include halo, nitro, cyano, —OR, —SR, —NR$_2$, —OCOR, —NRCOR, —COOR, —CONR$_2$, —SOR, —SO$_2$R, —SONR$_2$, —SO$_2$N R$_2$, wherein each R is independently alkyl, alkenyl, alkynyl, aryl or heteroaryl, or two R groups taken together with the atoms to which they are attached form a ring.

Preferably -L$^1$- of formula (IV) is substituted with one moiety -L$^2$-Z or -L$^2$-Z'.

An additional preferred embodiment for -L$^1$- is disclosed in WO2013/036857A1, which is herewith incorporated by reference in its entirety. Accordingly, a preferred moiety -L$^1$- is of formula (V):

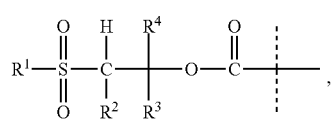

(V)

wherein
the dashed line indicates attachment to -D which is a PTH moiety and wherein attachment is through an amine functional group of -D;
—R$^1$ is selected from the group consisting of optionally substituted C$_1$-C$_6$ linear, branched, or cyclic alkyl; optionally substituted aryl; optionally substituted heteroaryl; alkoxy; and —NR$^{52}$;
—R$^2$ is selected from the group consisting of —H; optionally substituted C$_1$-C$_6$ alkyl; optionally substituted aryl; and optionally substituted heteroaryl;
—R$^3$ is selected from the group consisting of —H; optionally substituted C$_1$-C$_6$ alkyl; optionally substituted aryl; and optionally substituted heteroaryl;
—R$^4$ is selected from the group consisting of —H; optionally substituted C$_1$-C$_6$ alkyl; optionally substituted aryl; and optionally substituted heteroaryl;
each —R$^5$ is independently of each other selected from the group consisting of —H; optionally substituted C$_1$-C$_6$ alkyl; optionally substituted aryl; and optionally substituted heteroaryl; or when taken together two —R$^5$ can be cycloalkyl or cycloheteroalkyl;
wherein -L$^1$- is substituted with -L$^2$-Z or -L$^2$-Z' and wherein -L$^1$- is optionally further substituted;
wherein
-L$^2$- is a single chemical bond or a spacer;
—Z is a water-soluble carrier; and
—Z' is a water-insoluble carrier.

Only in the context of formula (V) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, preferably 6-10 carbons, including groups such as phenyl, naphthyl, and anthracene "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiszolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketne; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

Preferably -L$^1$- of formula (V) is substituted with one moiety -L$^2$-Z or -L$^2$-Z'.

A further preferred embodiment for -L$^1$- is disclosed in U.S. Pat. No. 7,585,837B2, which is herewith incorporated by reference in its entirety. Accordingly, a preferred moiety -L$^1$- is of formula (VI):

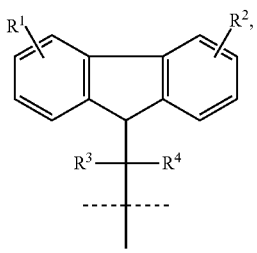

(VI)

wherein
the dashed line indicates attachment to -D which is a PTH moiety and wherein attachment is through an amine functional group of -D;

$R^1$ and $R^2$ are independently selected from the group consisting of hydrogen, alkyl, alkoxy, alkoxyalkyl, aryl, alkaryl, aralkyl, halogen, nitro, —$SO_3H$, —$SO_2NHR^5$, amino, ammonium, carboxyl, $PO_3H_2$, and $OPO_3H_2$;

$R^3$, $R^4$, and $R^5$ are independently selected from the group consisting of hydrogen, alkyl, and aryl;

wherein -$L^1$- is substituted with -$L^2$-Z or -$L^2$-Z' and wherein -$L^1$- is optionally further substituted;
wherein
-$L^2$- is a single chemical bond or a spacer;
—Z is a water-soluble carrier; and
—Z' is a water-insoluble carrier.

Suitable substituents for formulas (VI) are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Only in the context of formula (VI) the terms used have the following meaning: The terms "alkyl", "alkoxy", "alkoxyalkyl", "aryl", "alkaryl" and "aralkyl" mean alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

Preferably -$L^1$- of formula (VI) is substituted with one moiety -$L^2$-Z or -$L^2$-Z'.

A further preferred embodiment for -$L^1$- is disclosed in WO2002/089789A1, which is herewith incorporated by reference in its entirety. Accordingly, a preferred moiety -$L^1$- is of formula (VII):

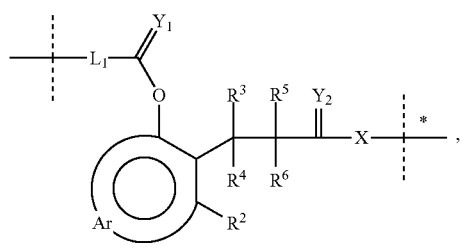

(VII)

wherein
the dashed line indicates attachment to -D which is a PTH moiety and wherein attachment is through an amine functional group of -D;
$L_1$ is a bifunctional linking group,
$Y_1$ and $Y_2$ are independently O, S or $NR^7$;

$R^2$, $R^3$, $R^4$, $R^5$, $R^6$ and $R^7$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula (VII) forms a multisubstituted aromatic hydrocarbon or a multi-substituted heterocyclic group;

X is a chemical bond or a moiety that is actively transported into a target cell, a hydrophobic moiety, or a combination thereof, y is 0 or 1;

wherein -$L^1$- is substituted with -$L^2$-Z or -$L^2$-Z' and wherein -$L^1$- is optionally further substituted;
wherein
-$L^2$- is a single chemical bond or a spacer;
—Z is a water-soluble carrier; and
—Z' is a water-insoluble carrier.

Only in the context of formula (VII) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moieties such as methoxy; and phenoxy includes moieties such as 3-nitrophenoxy. Halo- shall be understood to include fluoro, chloro, iodo and bromo.

Preferably -$L^1$- of formula (VII) is substituted with one moiety -$L^2$-Z or -$L^2$-Z'.

In another preferred embodiment -$L^1$- comprises a substructure of formula (VIII)

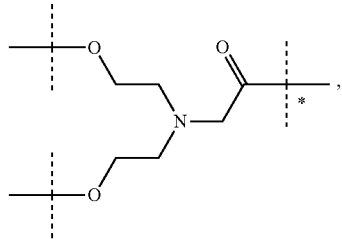

(VIII)

wherein
the dashed line marked with the asterisk indicates attachment to a nitrogen of -D which is a PTH moiety by forming an amide bond;
the unmarked dashed lines indicate attachment to the remainder of -$L^1$-; and
wherein -$L^1$- is substituted with -$L^2$-Z or -$L^2$-Z' and wherein -$L^1$- is optionally further substituted;
wherein
-$L^2$- is a single chemical bond or a spacer;
—Z is a water-soluble carrier; and
—Z' is a water-insoluble carrier.

Preferably -L$^1$- of formula (VIII) is substituted with one moiety -L$^2$-Z or -L$^2$-Z'.

In one embodiment -L$^1$- of formula (VIII) is not further substituted.

In another preferred embodiment -L$^1$- comprises a substructure of formula (IX)

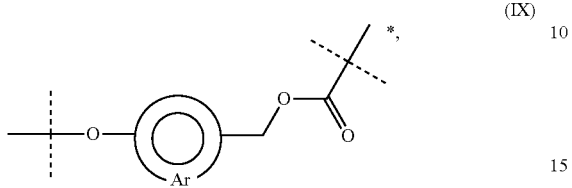

wherein
the dashed line marked with the asterisk indicates attachment to a nitrogen of -D which is a PTH moiety by forming a carbamate bond;
the unmarked dashed lines indicate attachment to the remainder of -L$^1$-; and
wherein -L$^1$- is substituted with -L$^2$-Z or -L$^2$-Z' and wherein -L$^1$- is optionally further substituted;
wherein
-L$^2$- is a single chemical bond or a spacer;
—Z is a water-soluble carrier; and
—Z' is a water-insoluble carrier.

Preferably -L$^1$- of formula (IX) is substituted with one moiety -L$^2$-Z or -L$^2$-Z'.

In one embodiment -L$^1$- of formula (IX) is not further substituted.

In the prodrugs of the present invention -L$^2$- is a chemical bond or a spacer moiety.

In one embodiment -L$^2$- is a chemical bond.

In another embodiment -L$^2$- is a spacer moiety.

When -L$^2$- is other than a single chemical bond, -L$^2$- is preferably selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —R$^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently of each other selected from the group consisting of —H, -T, C$_{1-50}$ alkyl, C$_{2-50}$ alkenyl, and C$_{2-50}$ alkynyl; wherein -T, C$_{1-50}$ alkyl, C$_{2-50}$ alkenyl, and C$_{2-50}$ alkynyl are optionally substituted with one or more —R$^{y2}$, which are the same or different, and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;
wherein each T is independently optionally substituted with one or more —R$^{y2}$, which are the same or different;
each —R$^{y2}$ is independently selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and
each —R$^{y3}$, —R$^{y3a}$, —R$^{y4}$, —R$^{y4a}$, —R$^{y5}$, —R$^{y5a}$ and —R$^{y5b}$ is independently selected from the group consisting of —H, and C$_{1-6}$ alkyl, wherein C$_{1-6}$ alkyl is optionally substituted with one or more halogen, which are the same or different.

When -L$^2$- is other than a single chemical bond, -L$^2$- is even more preferably selected from -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-20}$ alkyl, C$_{2-20}$ alkenyl, and C$_2$-20 alkynyl are optionally substituted with one or more —R$^{y2}$, which are the same or different and wherein C$_{1-20}$ alkyl, C$_{2-20}$ alkenyl, and C$_2$-20 alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently of each other selected from the group consisting of —H, -T, C$_{1-10}$ alkyl, C$_{2-10}$ alkenyl, and C$_{2-10}$ alkynyl; wherein -T, C$_{1-10}$ alkyl, C$_{2-10}$ alkenyl, and C$_{2-10}$ alkynyl are optionally substituted with one or more —R$^{y2}$, which are the same or different, and wherein C$_{1-10}$ alkyl, C$_{2-10}$ alkenyl, and C$_{2-10}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;
wherein each T is independently optionally substituted with one or more —R$^{y2}$, which are the same or different;
—R$^{y2}$ is selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$ N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and C$_{1-6}$ alkyl; wherein C$_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and C$_{1-6}$ alkyl; wherein C$_{1-6}$ alkyl is optionally substituted with one or more halogen, which are the same or different.

When -L$^2$- is other than a single chemical bond, -L$^2$- is even more preferably selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more —$R^{y2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^3$)($R^{y3a}$)—, —N($R^{y3}$)C(O)N($R^{y3a}$)—, and —OC(O)N($R^{y3}$)—;

—$R^{y1}$ and —$R^{y1a}$ are independently selected from the group consisting of —H, -T, C$_{1-10}$ alkyl, C$_{2-10}$ alkenyl, and C$_{2-10}$ alkynyl;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen, and C$_{1-6}$ alkyl; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and C$_{1-6}$ alkyl; wherein C$_{1-6}$ alkyl is optionally substituted with one or more halogen, which are the same or different.

Even more preferably, -L$^2$- is a C$_{1-20}$ alkyl chain, which is optionally interrupted by one or more groups independently selected from —O—, -T- and —C(O)N($R^{y1}$)—; and which C$_{1-20}$ alkyl chain is optionally substituted with one or more groups independently selected from —OH, -T and —C(O)N($R^{y6}R^{y6a}$); wherein —$R^{y1}$, —$R^{y6}$, —$R^{y6a}$ are independently selected from the group consisting of H and C$_{1-4}$ alkyl and wherein T is selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

Preferably, -L$^2$- has a molecular weight in the range of from 14 g/mol to 750 g/mol.

Preferably, -L$^2$- comprises a moiety selected from

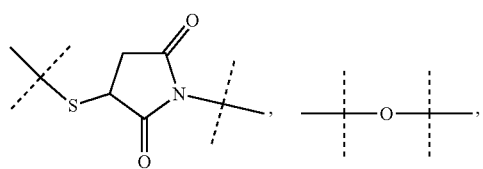

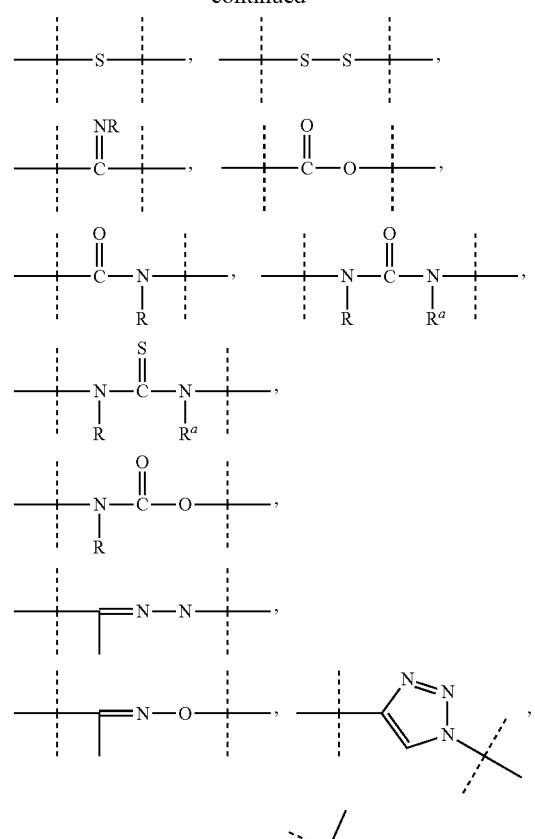

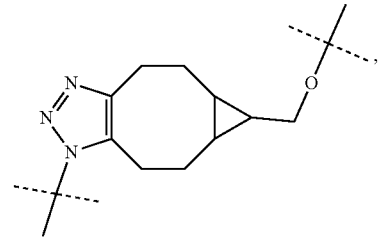

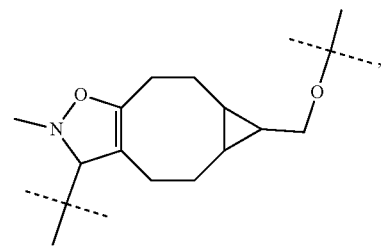

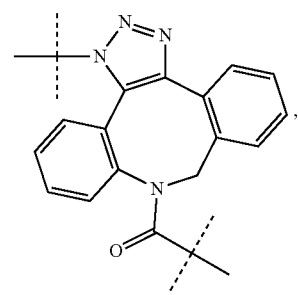

-continued

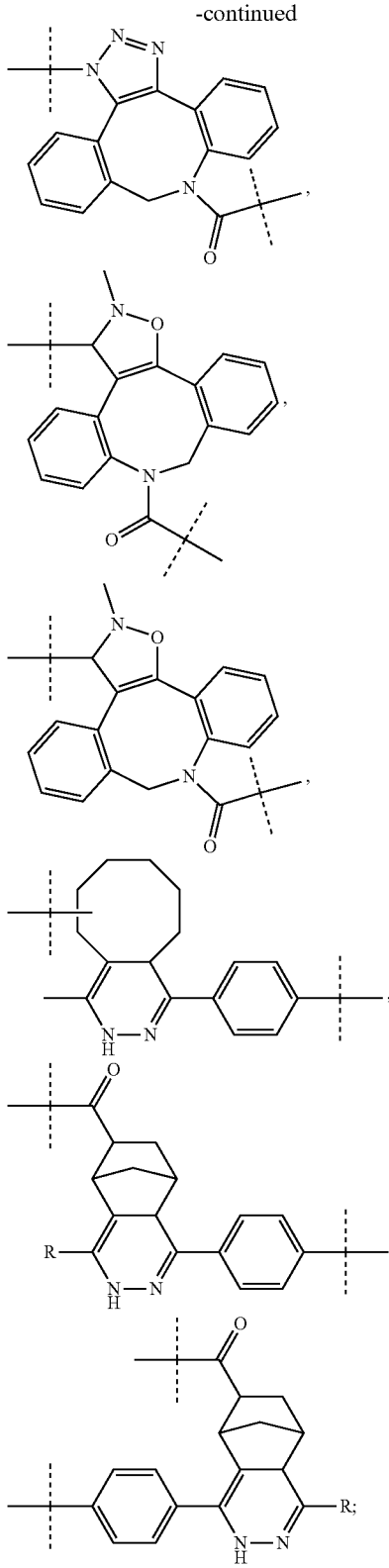

wherein
dashed lines indicate attachment to the rest of -L²-, -L¹-, —Z and/or —Z', respectively; and
—R and —Rᵃ are independently of each other selected from the group consisting of —H, methyl, ethyl, propyl, butyl, pentyl and hexyl.

In one preferred embodiment -L²- has a chain lengths of 1 to 20 atoms.

As used herein the term "chain length" with regard to the moiety -L²- refers to the number of atoms of -L²- present in the shortest connection between -L¹- and —Z.

Preferably, -L²- is of formula (i)

(i)

wherein
the dashed line marked with the asterisk indicates attachment to -L¹-;
the unmarked dashed line indicates attachment to —Z or —Z';
n is selected from the group consisting of 0, 1, 2, 3, 4, 5, 6, 7, 8, 9, 10, 11, 12, 13, 14, 15, 16, 17 and 18; and
wherein the moiety of formula (i) is optionally further substituted.

Preferably, n of formula (i) is selected from the group consisting of 3, 4, 5, 6, 7, 8, and 9. Even more preferably n of formula (i) is 4, 5, 6, or 7. In one embodiment n of formula (i) is 4. In another embodiment n of formula (i) is 5. In another embodiment n of formula (i) is 6.

In one preferred embodiment the moiety -L¹-L²- is selected from the group consisting of

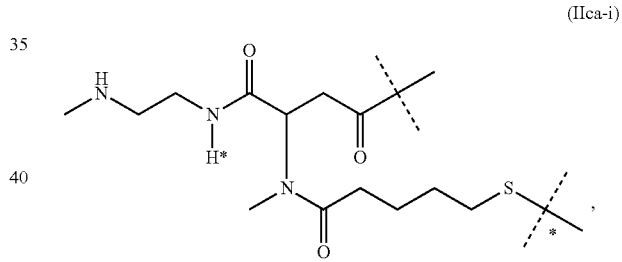

(IIca-i)

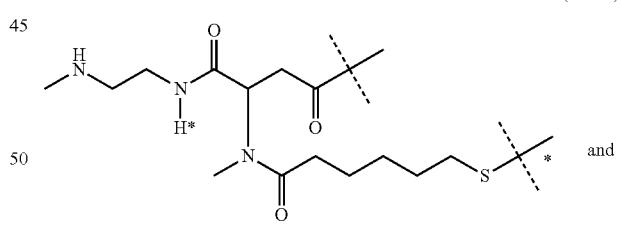

(IIca-ii)

and

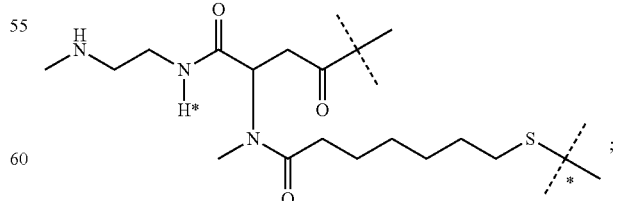

(IIca-iii)

wherein
the unmarked dashed line indicates the attachment to a nitrogen of -D which is a PTH moiety by forming an amide bond; and the dashed line marked with the asterisk indicates attachment to —Z or —Z'.

In one preferred embodiment the moiety -L¹-L²- is selected from the group consisting of

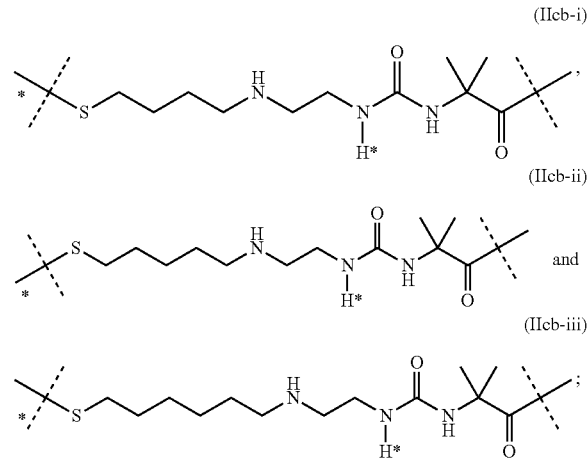

wherein
the unmarked dashed line indicates the attachment to a nitrogen of -D which is a PTH moiety by forming an amide bond; and
the dashed line marked with the asterisk indicates attachment to —Z or —Z'.

In a preferred embodiment the moiety -L¹-L²- is of formula (IIca-ii).

In another preferred embodiment the moiety -L¹-L²- is of formula (IIcb-iii).

Preferably, the PTH prodrug of the present invention is of formula (Ia) with x=1.

The carrier —Z comprises a $C_{8-24}$ alkyl or a polymer. Preferably, —Z comprises a polymer, preferably a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropyl-methacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

Preferably, —Z has a molecular weight ranging from 5 to 200 kDa. Even more preferably, —Z has a molecular weight ranging from 8 to 100 kDa, even more preferably ranging from 10 to 80 kDa, even more preferably from 12 to 60, even more preferably from 15 to 40 and most preferably —Z has a molecular weight of about 20 kDa. In another equally preferred embodiment —Z has a molecular weight of about 40 kDa.

In one embodiment such water-soluble carrier —Z comprises a protein. Preferred proteins are selected from the group consisting of carboxyl-terminal polypeptide of the chorionic gonadotropin as described in US 2012/0035101 A1 which are herewith incorporated by reference; albumin; XTEN sequences as described in WO 2011123813 A2 which are herewith incorporated by reference; proline/alanine random coil sequences as described in WO 2011/144756 A1 which are herewith incorporated by reference; proline/alanine/serine random coil sequences as described in WO 2008/155134 A1 and WO 2013/024049 A1 which are herewith incorporated by reference; and Fc fusion proteins.

In one embodiment —Z is a polysarcosine.

In another preferred embodiment —Z comprises a poly(N-methylglycine).

In a particularly preferred embodiment —Z comprises a random coil protein moiety.

In one preferred embodiment —Z comprises one random coil protein moiety.

In another preferred embodiment —Z comprises two random coil proteins moieties.

In another preferred embodiment —Z comprises three random coil proteins moieties.

In another preferred embodiment —Z comprises four random coil proteins moieties.

In another preferred embodiment —Z comprises five random coil proteins moieties.

In another preferred embodiment —Z comprises six random coil proteins moieties.

In another preferred embodiment —Z comprises seven random coil proteins moieties.

In another preferred embodiment —Z comprises eight random coil proteins moieties.

Preferably such random coil protein moiety comprises at least 25 amino acid residues and at most 2000 amino acids. Even more preferably such random coil protein moiety comprises at least 30 amino acid residues and at most 1500 amino acid residues. Even more preferably such random coil protein moiety comprises at least 50 amino acid residues and at most 500 amino acid residues.

In a preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine and proline. Even more preferably, at least 10%, but less than 75%, preferably less than 65%, of the total number of amino acid residues of such random coil protein moiety are proline residues. Preferably, such random coil protein moiety is as described in WO 2011/144756 A1 which is hereby incorporated by reference in its entirety. Even more preferably —Z comprises at least one moiety selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:51 and SEQ ID NO:61 as disclosed in WO2011/144756 which are hereby incorporated by reference. A moiety comprising such random coil protein comprising alanine and proline will be referred to as "PA" or "PA moiety".

Accordingly, —Z comprises a PA moiety.

In an equally preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, serine and proline. Even more preferably, at least 4%, but less than 40% of the total number of amino acid residues of such random coil protein moiety are proline residues. Preferably, such random coil protein moiety is as described in WO 2008/155134 A1 which is hereby incorporated by reference in its entirety. Even more preferably —Z comprises at least one moiety selected from the group consisting of SEQ ID NO:2, SEQ ID NO:4, SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:40, SEQ ID NO:42, SEQ ID NO:44, SEQ ID NO:46, SEQ ID NO:50, SEQ ID NO:52, SEQ ID NO:54 and SEQ ID NO:56 as disclosed in WO 2008/155134 A1, which are hereby incorporated by reference. A moiety comprising such random coil protein moiety comprising alanine, serine and proline will be referred to as "PAS" or "PAS moiety".

Accordingly, —Z comprises a PAS moiety.

In an equally preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine and proline. A moiety comprising such random coil protein moiety comprising alanine, glycine and proline will be referred to as "PAG" or "PAG moiety".

Accordingly, —Z comprises a PAG moiety.

In an equally preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from proline and glycine. A moiety comprising such random coil protein moiety comprising proline and glycine will be referred to as "PG" or "PG moiety".

Preferably, such PG moiety comprises a moiety of formula (a-0)

wherein
p is selected from the group consisting of 0, 1, 2, 3, 4 and 5;
q is selected from the group consisting of 0, 1, 2, 3, 4 and 5;
r is an integer ranging from and including 10 to 1000;
provided that at least one of p and q is at least 1;
Preferably, p of formula (a-0) is selected from the group consisting of 1, 2 and 3.
Preferably, q of formula (a-0) is selected from 0, 1 and 2.

Even more preferably the PG moiety comprises the sequence of SEQ ID: NO 122: GGPGGPGPGGPGGPGPGGPG Even more preferably, the PG moiety comprises the sequence of SEQ ID: NO 97 of formula (a-0-a)

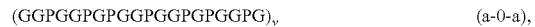

wherein
v is an integer ranging from and including 1 to 50.
Accordingly, —Z comprises a PG moiety.

In an equally preferred embodiment, —Z comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine, serine, threonine, glutamate and proline. Preferably, such random coil protein moiety is as described in WO 2010/091122 A1 which is hereby incorporated by reference. Even more preferably —Z comprises at least one moiety selected from the group consisting of SEQ ID NO:182, SEQ ID NO:183, SEQ ID NO:184; SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO: 197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO: 769, SEQ ID NO:770, SEQ ID NO:771, SEQ ID NO:772, SEQ ID NO:773, SEQ ID NO: 774, SEQ ID NO:775, SEQ ID NO:776, SEQ ID NO:777, SEQ ID NO:778, SEQ ID NO: 779, SEQ ID NO:1715, SEQ ID NO:1716, SEQ ID NO:1718, SEQ ID NO:1719, SEQ ID NO: 1720, SEQ ID NO: 1721 and SEQ ID NO:1722 as disclosed in WO2010/091122A1, which are hereby incorporated by reference. A moiety comprising such random coil protein moiety comprising alanine, glycine, serine, threonine, glutamate and proline will be referred to as "XTEN" or "XTEN moiety" in line with its designation in WO 2010/091122 A1.

Accordingly, —Z comprises an XTEN moiety.

In another preferred embodiment, —Z comprises a fatty acid derivate. Preferred fatty acid derivatives are those disclosed in WO 2005/027978 A2 and WO 2014/060512 A1 which are herewith incorporated by reference.

In another preferred embodiment —Z is a hyaluronic acid-based polymer.

In one embodiment —Z is a carrier as disclosed in WO 2012/02047 A1 which is herewith incorporated by reference.

In another embodiment —Z is a carrier as disclosed in WO 2013/024048 A1 which is herewith incorporated by reference.

In another preferred embodiment —Z is a PEG-based polymer, such as a linear, branched or multi-arm PEG-based polymer.

In one embodiment —Z is a linear PEG-based polymer.

In another embodiment —Z is a multi-arm PEG-based polymer. Preferably, —Z is a multi-arm PEG-based polymer having at least 4 PEG-based arms.

Preferably, such multi-arm PEG-based polymer —Z is connected to a multitude of moieties -L²-L¹-D, wherein each moiety -L²-L¹-D is preferably connected to the end of an arm, preferably to the end of an arm. Preferably such multi-arm PEG-based polymer —Z is connected to 2, 3, 4, 5, 6, 7, 8, 9, 10, 11, 12, 13, 14, 15 or 16 moieties -L²-L¹-D. Even more preferably such multi-arm PEG-based polymer —Z is connected to 2, 3, 4, 6 or 8 moieties -L²-L¹-D. Even more preferably such multi-arm PEG-based polymer —Z is connected to 2, 4 or 6 moieties -L²-L¹-D, even more preferably such multi-arm PEG-based polymer —Z is connected to 4 or 6 moieties -L²-L¹-D, and most preferably such multi-arm PEG-based polymer —Z is connected to 4 moieties -L²-L¹-D.

Preferably, such multi-arm PEG-based polymer —Z is a multi-arm PEG derivative as, for instance, detailed in the products list of JenKem Technology, USA (accessed by download from http://www.jenkemusa.com/Pages/PEG-Products.aspx on Dec. 18, 2014), such as a 4-arm-PEG derivative, in particular a 4-arm-PEG comprising a pentaerythritol core, an 8-arm-PEG derivative comprising a hexaglycerin core, and an 8-arm-PEG derivative comprising a tripentaerythritol core. More preferably, the water-soluble PEG-based carrier —Z comprises a moiety selected from:

a 4-arm PEG Amine comprising a pentaerythritol core:

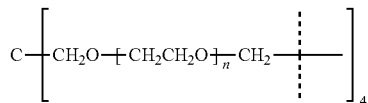

with n ranging from 20 to 500;
an 8-arm PEG Amine comprising a hexaglycerin core:

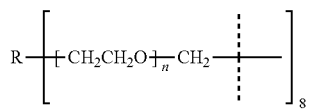

with n ranging from 20 to 500; and
R=hexaglycerin or tripentaerythritol core structure; and
a 6-arm PEG Amine comprising a sorbitol or dipentaerythritol core:

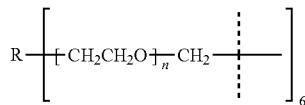

with n ranging from 20 to 500; and
R=comprising a sorbitol or dipentaerythritol core;
and wherein dashed lines indicate attachment to the rest of the PTH prodrug.

In a preferred embodiment —Z is a branched PEG-based polymer. In one embodiment —Z is a branched PEG-based polymer having one, two, three, four, five or six branching points. Preferably, —Z is a branched PEG-based polymer having one, two or three branching points. In one embodiment —Z is a branched PEG-based polymer having one branching point. In another embodiment —Z is a branched PEG-based polymer having two branching points. In another embodiment —Z is a branched PEG-based polymer having three branching points.

A branching point is preferably selected from the group consisting of —N<, —CH< and >C<.

Preferably, such branched PEG-based moiety —Z has a molecular weight of at least 10 kDa.

In one embodiment such branched moiety —Z has a molecular weight ranging from and including 10 kDa to 500 kDa, more preferably ranging from and including 10 kDa to 250 Da, even more preferably ranging from and including 10 kDa to 150 kDa, even more preferably ranging from and including 12 kDa to 100 kDa and most preferably ranging from and including kDa to 80 kDa.

Preferably, such branched moiety —Z has a molecular weight ranging from and including 10 kDa to 80 kDa. In one embodiment the molecular weight is about 10 kDa. In another embodiment the molecular weight of such branched moiety —Z is about 20 kDa. In another embodiment the molecular weight of such branched moiety —Z is about 30 kDa. In another embodiment the molecular weight of such a branched moiety —Z is about 40 kDa. In another embodiment the molecular weight of such a branched moiety —Z is about 50 kDa. In another embodiment the molecular weight of such a branched moiety —Z is about 60 kDa. In another embodiment the molecular weight of such a branched moiety —Z is about 70 kDa. In another embodiment the molecular weight of such a branched moiety —Z is about 80 kDa. Most preferably, such branched moiety —Z has a molecular weight of about 40 kDa.

Preferably, —Z or —Z' comprises a moiety

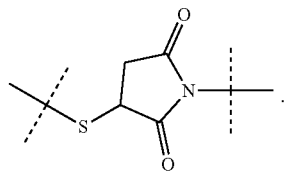

In an equally preferred embodiment —Z comprises an amide bond.

Preferably —Z comprises a moiety of formula (a)

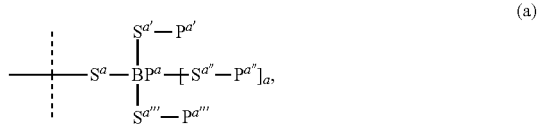

wherein
the dashed line indicates attachment to -L²- or to the remainder of —Z;
$BP^a$ is a branching point selected from the group consisting of —N<, —CR< and >C<;
—R is selected from the group consisting of —H and $C_{1-6}$ alkyl;
a is 0 if $BP^a$ is —N< or —CR< and n is 1 if $BP^a$ is >C<;
—$S^a$—, —$S^{a'}$, —$S^{a''}$— and —$S^{a'''}$— are independently of each other a chemical bond or are selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —$R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^2$)—, —S(O)$_2$N($R^2$)—, —S(O) N($R^2$)—, —S(O)$_2$—, —S(O)—, —N($R^2$)S(O)$_2$N ($R^{2a}$)—, —S—, —N($R^2$)—, —OC(O$R^2$)($R^{2a}$)—, —N($R^2$)C(O)N($R^{2a}$)—, and —OC(O)N($R^2$)—;

each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —$R^1$, which are the same or different;

each —$R^1$ is independently selected from the group consisting of halogen, —CN, oxo (=O), —COO$R^3$, —O$R^3$, —C(O)$R^3$, —C(O)N($R^3R^{3a}$), —S(O)$_2$N ($R^3R^{3a}$), —S(O)N($R^3R^{3a}$), —S(O)$_2R^3$, —S(O)$R^3$, —N($R^3$)S(O)$_2$N($R^{3a}R^{3b}$), —S$R^3$, —N($R^3R^{3a}$), —NO$_2$, —OC(O)$R^3$, —N($R^3$)C(O)$R^{3a}$, —N($R^3$)S(O)$_2R^{3a}$, —N($R^3$)S(O)$R^{3a}$, —N($R^3$)C(O)O$R^{3a}$, —N($R^3$)C(O)N ($R^{3a}R^{3b}$), —OC(O)N($R^3R^{3a}$), and $C_{1-6}$ alkyl; wherein $C_{1-6}$ alkyl is optionally substituted with one or more halogen, which are the same or different;

each —$R^2$, —$R^{2a}$, —$R^3$, —$R^{3a}$ and —$R^{3b}$ is independently selected from the group consisting of —H, and $C_{1-6}$ alkyl, wherein $C_{1-6}$ alkyl is optionally substituted with one or more halogen, which are the same or different; and —$P^{a'}$, —$P^{a''}$ and —$P^{a'''}$ are independently a polymeric moiety.

In one embodiment $BP^a$ of formula (a) is —N<.

In another embodiment $BP^a$ of formula (a) is >C<.

In a preferred embodiment $BP^a$ of formula (a) is —CR<. Preferably, —R is —H. Accordingly, a of formula (a) is 0.

In one embodiment —$S^a$— of formula (a) is a chemical bond.

In another embodiment —$S^a$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of -T-, —C(O) O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N ($R^{4a}$)—, —S—, —N($R^4$)—, —OC(O$R^4$)($R^{4a}$)—, —N($R^4$) C(O)N($R^{4a}$)—, and —OC(O)N($R^4$)—; wherein -T- is a 3- to 10-membered heterocyclyl; and —$R^4$ and —$R^{4a}$ are independently selected from the group consisting of —H, methyl, ethyl, propyl and butyl.

Preferably —$S^a$— of formula (a) is selected from the group consisting of $C_{1-10}$ alkyl which is interrupted by one or more chemical groups selected from the group consisting of -T-, —C(O)N($R^4$)— and —O—.

In one embodiment —$S^{a'}$— of formula (a) is a chemical bond.

In another embodiment —$S^{a'}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N ($R^{4a}$)—, —S—, —N($R^4$)—, —OC(O$R^4$)($R^{4a}$)—, —N($R^4$) C(O)N($R^{4a}$)—, and —OC(O)N($R^4$)—; wherein —$R^4$ and —$R^{4a}$ are independently selected from the group consisting of —H, methyl, ethyl, propyl and butyl. Preferably —$S^{a'}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In one embodiment —$S^{a''}$— of formula (a) is a chemical bond.

In another embodiment —$S^{a''}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N ($R^{4a}$)—, —S—, —N($R^4$)—, —OC(O$R^4$)($R^{4a}$)—, —N($R^4$) C(O)N($R^{4a}$)—, and —OC(O)N($R^4$)—; wherein —$R^4$ and —$R^{4a}$ are independently selected from the group consisting of —H, methyl, ethyl, propyl and butyl. Preferably —$S^{a''}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In one embodiment —$S^{a'''}$— of formula (a) is a chemical bond.

In another embodiment —$S^{a'''}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —S(O)$_2$N($R^4$)—, —S(O)N($R^4$)—, —S(O)$_2$—, —S(O)—, —N($R^4$)S(O)$_2$N ($R^{4a}$)—, —S—, —N($R^4$)—, —OC(O$R^4$)($R^{4a}$)—, —N($R^4$) C(O)N($R^{4a}$)—, and —OC(O)N($R^4$)—; wherein —$R^4$ and —$R^{4a}$ are independently selected from the group consisting of —H, methyl, ethyl, propyl and butyl. Preferably —$S^{a'''}$— of formula (a) is selected from the group consisting of methyl, ethyl, propyl, butyl, which are optionally interrupted by one or more chemical groups selected from the group consisting of —O—, —C(O)— and —C(O)N($R^4$)—.

Preferably, —$P^{a'}$, —$P^{a''}$ and —$P^{a'''}$ of formula (a) independently comprise a polymer selected from the group consisting of 2-methacryloyl-oxyethyl phosphoyl cholins, poly(acrylic acids), poly(acrylates), poly(acrylamides), poly (alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly (ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

More preferably, —P$^{a'}$, —P$^{a''}$ and —P$^{a'''}$ of formula (a) independently comprise a PEG-based moiety. Even more preferably, —P$^{a'}$, —P$^{a''}$ and —P$^{a'''}$ of formula (a) independently comprise a PEG-based moiety comprising at least 20% PEG, even more preferably at least 30%, even more preferably at least 40% PEG, even more preferably at least 50% PEG, even more preferably at least 60% PEG, even more preferably at least 70% PEG, even more preferably at least 80% PEG and most preferably at least 90% PEG.

Preferably, —P$^{a'}$, —P$^{a''}$ and —P$^{a'''}$ of formula (a) independently have a molecular weight ranging from and including 5 kDa to 50 kDa, more preferably have a molecular weight ranging from and including 5 kDa to 40 kDa, even more preferably ranging from and including 7.5 kDa to kDa, even more preferably ranging from and 7.5 to 30 kDa, even more preferably ranging from and including 10 to 30 kDa.

In one embodiment —P$^{a'}$, —P$^{a''}$ and —P$^{a'''}$ of formula (a) have a molecular weight of about 5 kDa.

In another embodiment —P$^{a'}$, —P$^{a''}$ and —P$^{a'''}$ of formula (a) have a molecular weight of about 7.5 kDa.

In another embodiment —P$^{a'}$, —P$^{a''}$ and —P$^{a'''}$ of formula (a) have a molecular weight of about 10 kDa.

In another embodiment —P$^{a'}$, —P$^{a''}$ and —P$^{a'''}$ of formula (a) have a molecular weight of about 12.5 kDa.

In another embodiment —P$^{a'}$, —P$^{a''}$ and —P$^{a'''}$ of formula (a) have a molecular weight of about 15 kDa.

In another embodiment —P$^{a'}$, —P$^{a''}$ and —P$^{a'''}$ of formula (a) have a molecular weight of about 20 kDa.

In one embodiment —Z comprises one moiety of formula (a).

In another embodiment —Z comprises two moieties of formula (a).

In another embodiment —Z comprises three moieties of formula (a).

Preferably, —Z is a moiety of formula (a).

More preferably, —Z comprises a moiety of formula (b)

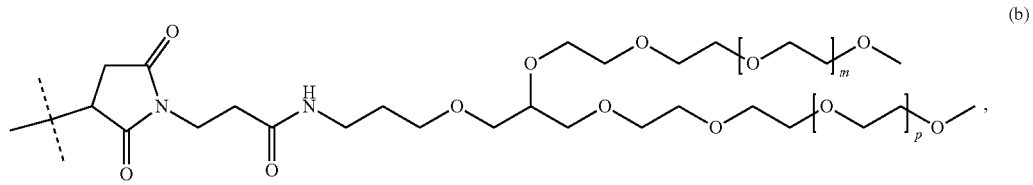

wherein
the dashed line indicates attachment to -L$^2$- or to the remainder of —Z; and m and p are independently of each other an integer ranging from and including 150 to 1000; preferably an integer ranging from and including 150 to 500; more preferably an integer ranging from and including 200 to 500; and most preferably an integer ranging from and including 400 to 500.

Preferably, m and p of formula (b) are the same integer.
Most preferably m and p of formula (b) are about 450.
Preferably, —Z is a moiety of formula (b).

The carrier —Z' is a water-insoluble polymer, even more preferably a hydrogel. Preferably, such hydrogel comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropyl-methacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

If the carrier —Z' is a hydrogel, it is preferably a hydrogel comprising PEG or hyaluronic acid. Most preferably such hydrogel comprises PEG.

Even more preferably, the carrier —Z' is a hydrogel as described in WO 2006/003014 A2, WO 2011/012715 A1 or WO 2014/056926 A1, which are herewith incorporated by reference in their entirety.

In another embodiment —Z' is a polymer network formed through the physical aggregation of polymer chains, which physical aggregation is preferably caused by hydrogen bonds, crystallization, helix formation or complexation. In one embodiment such polymer network is a thermogelling polymer.

Preferably, the total mass of the PTH prodrug of the present invention is at least 10 kDa, such as at least 12 kDa, such as at least 15 kDa, such as at least 20 kDa or such as at least 30 kDa. It is preferred that the total mass of the PTH prodrug of the present invention is at most 250 kDa, such as at most 200 kDa, 180 kDa, 150 kDa or 100 kDa.

In a preferred embodiment the PTH prodrug of the present invention is of formula (IIe-i):

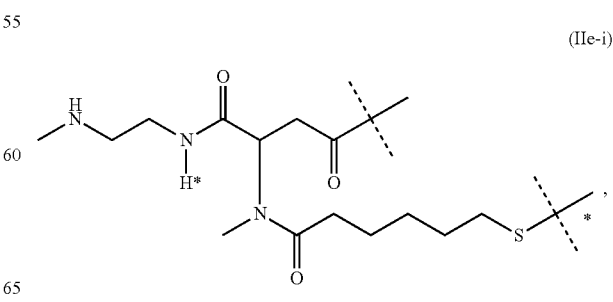

wherein
the unmarked dashed line indicates the attachment to a nitrogen of -D which is a PTH moiety by forming an amide bond; and
the dashed line marked with the asterisk indicates attachment to a moiety

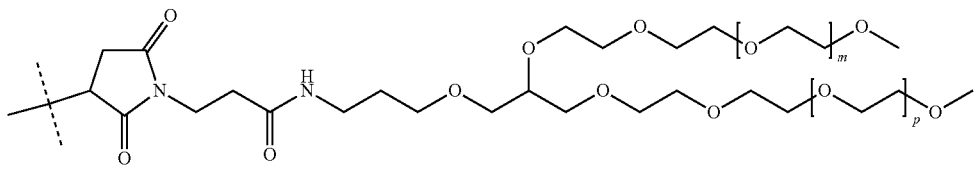

wherein
m and p are independently an integer ranging from and including 400 to 500.

Preferably, -D is attached to the PTH prodrug of formula (IIe-i) through the N-terminal amine functional group of the PTH moiety.

In another preferred embodiment the PTH prodrug of the present invention is of formula (IIf-i):

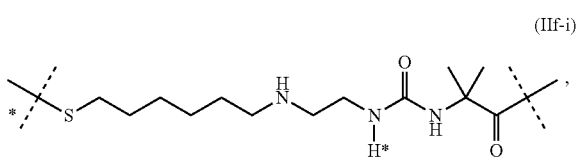
(IIf-i)

wherein
the unmarked dashed line indicates the attachment to a nitrogen of -D which is a PTH moiety by forming an amide bond; and
the dashed line marked with the asterisk indicates attachment to a moiety

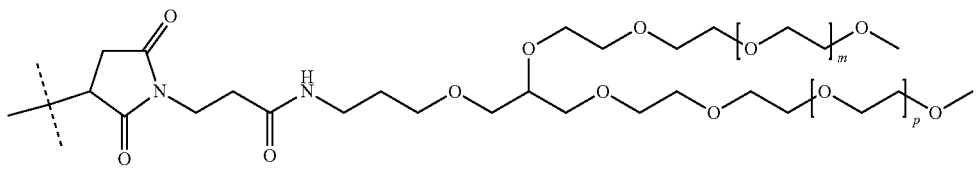

wherein
m and p are independently an integer ranging from and including 400 to 500.

Preferably, -D is attached to the PTH prodrug of formula (If-i) through the N-terminal amine functional group of the PTH moiety.

In a preferred embodiment the residual activity of the PTH prodrug of the present invention is less than 10%, more preferably less than 1%, even more preferably less than 0.1%, even more preferably less than 0.01%, even more preferably less than 0.001% and most preferably less than 0.0001%.

As used herein the term "residual activity" refers to the activity exhibited by the PTH prodrug of the present invention with the PTH moiety bound to a carrier in relation to the activity exhibited by the corresponding free PTH. In this context the term "activity" refers to binding to an activation of the PTH/PTHrP1 receptor resulting in activation of adenylate cyclase to generate cAMP, phospholipase C to generate intracellular calcium, or osteoblastic expression of RANKL (which binds to RANK (Receptor Activator of Nuclear Factor kB) on osteoclasts. It is understood that measuring the residual activity of the PTH prodrug of the present invention takes time during which a certain amount of PTH will be released from the PTH prodrug of the present invention and that such released PTH will distort the results measured for the PTH prodrug. It is thus accepted practice to test the residual activity of a prodrug with a conjugate in which the drug moiety, in this case PTH, is non-reversibly, i.e. stably, bound to a carrier, which as closely as possible resembles the structure of the PTH prodrug for which residual activity is to be measured.

A suitable assay for measuring PTH activity and the residual activity of the PTH prodrug of the present invention, preferably in the form of a stable analog, is for example measuring cAMP production from HEK293 cells overexpressing the PTH/PTHrP1 receptor (Hohenstein et al., Journal of Pharmaceutical and Biomedical Analysis, September 2014, 98: 345-350), or a cell-based assay to detect cyclicAMP release, detected by homogenous time-resolved fluorescence (HTRF) or ELISA, that has been validated according to ICHQ2(R1) (http://www.criver.com/files/pdfs/bps/bp_r_in_vitro_bioassays.aspx).

It was surprisingly found that using N-terminal attachment of -L$^1$- and using a branched PEG carrier for —Z, i.e. a 2×20 kDa PEG, results in a particularly low residual activity. Reduced residual activity is desirable as it reduces side-effects.

It was also surprisingly found that PTH produgs of the present invention are capable of achieving a stable plasma profile of PTH which ensures physiological serum and urinary calcium levels or even reduced urinary calcium levels.

Preferably, after subcutaneous administration the pharmacokinetic profile of a PTH prodrug of the present invention exhibits a peak to trough ratio of less than 4 within one injection interval.

As used herein the term "injection interval" refers to the time between two consecutive administrations of the pharmaceutical composition of the present invention.

As used herein the term "peak to trough ratio" refers to the ratio between the highest plasma concentration and the lowest plasma concentration of PTH released from the PTH prodrug of the present invention within the time period between two consecutive administrations to a non-human primate, preferably to a cynomolgus monkey.

The time period between two consecutive subcutaneous administrations, i.e. the administration interval, is preferably at least 24 hours, such as 24 hours, 36 hours, 48 hours, 60 hours, 72 hours, every 84 hours, 96 hours, 108 hours, 120 hours, 132 hours, 144 hours, 156 hours, one week, two weeks, three weeks or four weeks.

In one embodiment the time period between two consecutive subcutaneous administrations is 24 hours.

In another embodiment the time period between two consecutive subcutaneous administrations is 48 hours.

In another embodiment the time period between two consecutive subcutaneous administrations is 72 hours.

In another embodiment the time period between two consecutive subcutaneous administrations is 96 hours.

In another embodiment the time period between two consecutive subcutaneous administrations is 120 hours.

In another embodiment the time period between two consecutive subcutaneous administrations is 144 hours.

In another embodiment the time period between two consecutive subcutaneous administrations is one week.

The peak to trough ratio measured in each administration interval is less than 4, preferably less than 3.8, more preferably less than 3.6, even more preferably less than 3.4, even more preferably less than 3.2, even more preferably less than 3, even more preferably less than 2.8, even more preferably less than 2.6, even more preferably less than 2.4, even more preferably less than 2.2 and most preferably less than 2.

Another aspect of the present invention is a pharmaceutical composition comprising at least one PTH prodrug of the present invention and at least one excipient.

Preferably, the pharmaceutical composition comprising at least one PTH prodrug of the present invention has a pH ranging from and including pH 3 to pH 8. More preferably, the pharmaceutical composition has a pH ranging from and including pH 4 to pH 6. Most preferably, the pharmaceutical composition has a pH ranging from and including pH 4 to pH 5.

In one embodiment the pharmaceutical composition comprising at least one PTH prodrug of the present invention and at least one excipient is a liquid or suspension formulation. It is understood that the pharmaceutical composition is a suspension formulation if the PTH prodrug of the present invention comprises a water-insoluble carrier —Z'.

In another embodiment the pharmaceutical composition comprising at least one PTH prodrug of the present invention and at least one excipient is a dry formulation.

Such liquid, suspension or dry pharmaceutical composition comprises at least one excipient. Excipients used in parenteral formulations may be categorized as, for example, buffering agents, isotonicity modifiers, preservatives, stabilizers, anti-adsorption agents, oxidation protection agents, viscosifiers/viscosity enhancing agents, or other auxiliary agents. However, in some cases, one excipient may have dual or triple functions. Preferably, the at least one excipient comprised in the pharmaceutical composition of the present invention is selected from the group consisting of (i) Buffering agents: physiologically tolerated buffers to maintain pH in a desired range, such as sodium phosphate, bicarbonate, succinate, histidine, citrate and acetate, sulphate, nitrate, chloride, pyruvate; antacids such as $Mg(OH)_2$ or $ZnCO_3$ may be also used;

(ii) Isotonicity modifiers: to minimize pain that can result from cell damage due to osmotic pressure differences at the injection depot; glycerin and sodium chloride are examples; effective concentrations can be determined by osmometry using an assumed osmolality of 285-315 mOsmol/kg for serum;

(iii) Preservatives and/or antimicrobials: multidose parenteral formulations require the addition of preservatives at a sufficient concentration to minimize risk of patients becoming infected upon injection and corresponding regulatory requirements have been established; typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride;

(iv) Stabilizers: Stabilisation is achieved by strengthening of the protein-stabilising forces, by destabilisation of the denatured state, or by direct binding of excipients to the protein; stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives; in addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to the inner surface of the formulation's container; e.g., poloxamer (Pluronic F-68), PEG dodecyl ether (Brij 35), polysorbate 20 and 80, dextran, polyethylene glycol, PEG-polyhistidine, BSA and HSA and gelatins; chosen concentration and type of excipient depends on the effect to be avoided but typically a monolayer of surfactant is formed at the interface just above the CMC value;

(vi) Oxidation protection agents: antioxidants such as ascorbic acid, ectoine, methionine, glutathione, monothioglycerol, morin, polyethylenimine (PEI), propyl gallate, and vitamin E; chelating agents such as citric acid, EDTA, hexaphosphate, and thioglycolic acid may also be used;

(vii) Viscosifiers or viscosity enhancers: in case of a suspension retard settling of the particles in the vial and syringe and are used in order to facilitate mixing and resuspension of the particles and to make the suspension easier to inject (i.e., low force on the syringe plunger); suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly (oxyethylene) blocks and hydrophobic poly(oxypropylene) blocks to make up a triblock of poly (oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone; such block copolymers as well as the abovementioned poloxamers may exhibit reverse thermal gelation behavior (fluid state at room temperature to facilitate administration and gel state above sol-gel transition temperature at body temperature after injection);

(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue; a spreading agent such as but not limited to hyaluronidase temporarily decreases the viscosity of the extracellular matrix and promotes diffusion of injected drugs; and (ix) Other auxiliary agents: such as wetting agents, viscosity modifiers, antibiotics, hyaluronidase; acids and bases such as hydrochloric acid and sodium hydroxide are auxiliary agents necessary for pH adjustment during manufacture.

The pharmaceutical composition comprising at least one PTH prodrug may be administered to a patient by various modes of administration, such as via topical, enteral or parenteral administration and by methods of external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection and infusion, direct delivery to the brain via implanted device allowing delivery of the invention or the like to brain tissue or brain fluids (e.g., Ommaya Reservoir), direct intracerebroventricular injection or infusion, injection or infusion into brain or brain associated regions, injection into the subchoroidal space, retro-orbital injection and ocular instillation. Preferably the pharmaceutical composition comprising at least one PTH prodrug is administered via subcutaneous injection.

Subcutaneous injection is preferably done with a syringe and needle or with a pen injector, even more preferably with a pen injector.

Another aspect of the present invention is the use of the PTH prodrug or a pharmaceutically acceptable salt thereof or a pharmaceutical composition comprising at least one PTH prodrug of the present invention as a medicament.

Another aspect of the present invention is the PTH prodrug or a pharmaceutically acceptable salt thereof or the pharmaceutical composition comprising at least one PTH prodrug of the present invention for use in the treatment of a disease which can be treated with PTH.

Preferably, said disease is selected from the group consisting of hypoparathyroidism, hyperphosphatemia, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfect, fibrous dysplasia, rheumatoid arthritis, Paget's disease, humoral hypercalcemia associated with malignancy, osteopenia, periodontal disease, bone fracture, alopecia, chemotherapy-induced alopecia, and thrombocytopenia. Most preferably said disease is hypoparathyroidism.

In one embodiment the patient undergoing the method of treatment of the present invention is a mammalian patient, preferably a human patient.

Another aspect of the present invention is the use of the PTH prodrug or a pharmaceutically acceptable salt thereof or the pharmaceutical composition comprising at least one PTH prodrug of the present invention for the manufacture of a medicament for treating a disease which can be treated with PTH.

Preferably, said disease is selected from the group consisting of hypoparathyroidism, hyperphosphatemia, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfect, fibrous dysplasia, rheumatoid arthritis, Paget's disease, humoral hypercalcemia associated with malignancy, osteopenia, periodontal disease, bone fracture, alopecia, chemotherapy-induced alopecia, and thrombocytopenia. Most preferably said disease is hypoparathyroidism.

In one embodiment the disease to be treated with the PTH prodrug or a pharmaceutically acceptable salt thereof or the pharmaceutical composition comprising at least one PTH prodrug of the present invention occurs in a mammalian patient, preferably in a human patient.

A further aspect of the present invention is a method of treating, controlling, delaying or preventing in a mammalian patient, preferably a human patient, in need of the treatment of one or more diseases which can be treated with PTH, comprising the step of administering to said patient in need thereof a therapeutically effective amount of PTH prodrug or a pharmaceutically acceptable salt thereof or a pharmaceutical composition comprising PTH prodrug of the present invention.

Preferably, the one or more diseases which can be treated with PTH is selected from the group consisting of hypoparathyroidism, hyperphosphatemia, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfect, fibrous dysplasia, rheumatoid arthritis, Paget's disease, humoral hypercalcemia associated with malignancy, osteopenia, periodontal disease, bone fracture, alopecia, chemotherapy-induced alopecia, and thrombocytopenia. Most preferably said disease is hypoparathyroidism.

An additional aspect of the present invention is a method of administering the PTH prodrug, a pharmaceutically acceptable salt thereof or the pharmaceutical composition of the present invention, wherein the method comprises the step of administering the PTH prodrug, a pharmaceutically acceptable salt thereof or the pharmaceutical composition of the present invention via topical, enteral or parenteral administration and by methods of external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection and infusion, intranasal, oral, transpulmonary and transdermal administration, direct delivery to the brain via implanted device allowing delivery of the invention or the like to brain tissue or brain fluids (e.g., Ommaya Reservoir), direct intracerebroventricular injection or infusion, injection or infusion into brain or brain associated regions, injection into the subchoroidal space, retro-orbital injection and ocular instillation, preferably via subcutaneous injection.

In a preferred embodiment, the present invention relates to a PTH prodrug or pharmaceutically acceptable salt thereof or a pharmaceutical composition of the present invention, for use in the treatment of hypoparathyroidism via subcutaneous injection.

EXAMPLES

Materials and Methods

Side chain protected PTH(1-34) (SEQ ID NO:51) on TCP resin having Boc protected N-terminus and ivDde protected side chain of Lys26 (synthesized by Fmoc-strategy) was obtained from CASLO ApS, Kongens Lyngby, Denmark and Peptide Specialty Laboratories GmbH, Heidelberg, Germany.

Side chain protected PTH(1-34) on TCP resin having Fmoc protected N-terminus (synthesized by Fmoc-strategy) was obtained from CASLO ApS, Kongens Lyngby, Denmark and Peptide Specialty Laboratories GmbH, Heidelberg, Germany.

PEG 2×20 kDa maleimide, Sunbright GL2-400MA and PEG 2×10 kDa maleimide, Sunbright GL2-200MA were purchased from NOF Europe N.V., Grobbendonk, Belgium. S-Trityl-6-mercaptohexanoic acid was purchased from Polypeptide, Strasbourg, France. HATU was obtained from Merck Biosciences GmbH, Schwalbach/Ts, Germany. Fmoc-N-Me-Asp(OBn)-OH was obtained from Peptide International Inc., Louisville, KY, USA. Fmoc-Aib-OH was purchased from Iris Biotech GmbH, Marktredwitz, Germany. All other chemicals and reagents were purchased from Sigma Aldrich GmbH, Taufkirchen, Germany, unless a different supplier is mentioned.

Compound 11a (examples 11-15) was synthesized following the procedure described in patent WO20095479A2, example 1.

Syringes equipped with polyethylenene frits (MultiSynTech GmbH, Witten, Germany) were used as reaction vessels or for washing steps of peptide resins.

General procedure for the removal of ivDde protecting group from side chain protected PTH on resin: The resin was pre-swollen in DMF for 30 min and the solvent was discarded. The ivDde group was removed by incubating the resin with DMF/hydrazine hydrate 4/1 (v/v, 2.5 mL/g resin) for 8×15 min. For each step fresh DMF/hydrazine hydrate solution was used. Finally, the resin was washed with DMF (10×), DCM (10×) and dried in vacuo.

General procedure for the removal of Fmoc protecting group from protected PTH on resin: The resin was pre-swollen in DMF for 30 min and the solvent was discarded. The Fmoc group was removed by incubating the resin with DMF/piperidine/DBU 96/2/2 (v/v/v, 2.5 mL/g resin) for 3×10 min. For each step fresh DMF/piperidine/DBU hsolution was used. Finally, the resin was washed with DMF (10×), DCM (10×) and dried in vacuo.

RP-HPLC Purification:

For preparative RP-HPLC a Waters 600 controller and a 2487 Dual Absorbance Detector was used, equipped with the following columns: Waters XBridge™ BEH300 Prep C18 5 µm, 150×10 mm, flow rate 6 mL/min, or Waters XBridge™ BEH300 Prep C18 10 µm, 150×30 mm, flow rate 40 mL/min. Linear gradients of solvent system A (water containing 0.1% TFA v/v) and solvent system B (acetonitrile containing 0.1% TFA v/v) were used. HPLC fractions containing product were pooled and lyophilized if not stated otherwise.

Flash Chromatography:

Flash chromatography purifications were performed on an Isolera One system from Biotage AB, Sweden, using Biotage KP-Sil silica cartridges and n-heptane and ethyl acetate as eluents. Products were detected at 254 nm.

Ion Exchange Chromatography:

Ion exchange chromatography (IEX) was performed using an Amersham Bioscience AEKTAbasic system equipped with a MacroCap SP cation exchanger column (Amersham Bioscience/GE Healthcare). 17 mM acetic acid pH 4.5 (solvent A) and 17 mM acetic acid, 1 M NaCl, pH 4.5 (solvent B) were used as mobile phases.

Size Exclusion Chromatography:

Size exclusion chromatography (SEC) was performed using an Amersham Bioscience AEKTAbasic system equipped with HiPrep 26/10 desalting columns (Amersham Bioscience/GE Healthcare). 0.1% (v/v) acetic acid was used as mobile phase.

For in vitro release kinetics studies of compound 31, a pH 7.40 buffer (100 mM phosphate, 10 mM L-methionine, 3 mM EDTA, 0.05% Tween-20) was used instead of 0.1% AcOH as mobile phase.

Analytical Methods

Analytical ultra-performance LC (UPLC)-MS was performed on a Waters Acquity system equipped with a Waters BEH300 C18 column (2.1×50 mm, 1.7 µm particle size, flow: 0.25 mL/min; solvent A: water containing 0.04% TFA (v/v), solvent B: acetonitrile containing 0.05% TFA (v/v)) coupled to a LTQ Orbitrap Discovery mass spectrometer from Thermo Scientific or coupled to a Waters Micromass ZQ.

Quantitative measurements of serum calcium (sCa), urinary calcium and serum phosporous (sP) were performed on a Roche-Hitachi P800 modular biochemistry instrument.

Quantification of Plasma Total PTH(1-34) Concentrations:

Plasma total PTH(1-34) concentrations were determined by quantification of a signature peptide close to the N-terminus (sequence: IQLMHNLGK (SEQ ID NO:123)) and a C-terminal signature peptide (sequence: LQDVHNF (SEQ ID NO:124)) after plasma protein precipitation, followed by sequential digestion with Endoproteinase Lys-C (origin: Lysobacter enzymogenes) and Endoproteinase Glu-C (origin: *Staphylococcus aureus* V8) of the supernatant. Subsequently, analysis by reversed phase liquid chromatography and detection by mass spectrometry (RP-HPLC-MS) was performed.

Calibration standards of PTH(1-34) conjugate in blank plasma were prepared as follows: The PTH(1-34) conjugate formulation was pre-diluted with formulation buffer to aqueous standard solutions ranging from 5 to 300 pg/mL PTH (1-34) eq (concentration range 1) and 0.5 pg/mL to 100 pg/mL PTH(1-34) eq (concentration range 2), respectively. Each aqueous standard solution was then diluted 1:100 with thawed heparinized plasma to obtain concentration ranges from 50 to 3000 ng/mL PTH(1-34) eq (dilution with rat plasma of concentration range 1) and to 1000 ng/mL PTH (1-34) eq (dilution with monkey plasma of concentration range 2).

These solutions were used for the generation of a calibration curve. Calibration curves were weighted 1/×2 for both signature peptides. For quality control, three samples independent from the calibration standard solutions were prepared accordingly. Concentrations at the lower end (3-5 fold concentration of the respective LLOQ), the middle range (0.05-0.1 fold concentration of the respective ULOQ) and the upper end (0.5-0.8 fold concentration of the respective ULOQ).

Sample preparation volumes can be altered depending on the targeted signal response after sample preparation. Processing procedure of the protein precipitation is described here for the analysis of plasma samples originated in monkey species. Protein precipitation was carried out by addition of 200 μL of precooled (5-10° C.) methanol to 100 μL of the plasma sample. 180 μL of the supernatant were transferred into a new well-plate and evaporated to dryness (under a gentle nitrogen stream at 45° C.). 50 μL of reconstitution solvent (50 mM Tris 0.5 mM $CaCl_2$) buffer, adjusted to pH 8.0) were used to dissolve the residue. Proteolytic digestion was performed as follows:

20 μg of Lys-C (order number 125-05061, Wako Chemicals GmbH, Neuss, Germany) were dissolved in 80 μL of 10 mM acetic acid. 3 μL of the Lys-C solution were added to each cavity and samples incubated for 15 hours at 37° C. Afterwards 10 μg of Glu-C (order number V1651, Promega GmbH, Mannheim, Germany) were dissolved in 25 μL water, added to each cavity and incubation continued for 1.5 hours at 37° C. After incubation samples were acidified with 2 μL water/formic acid 4:6 (v/v) and 10 μL were injected into the UPLC-MS system.

LC-MS analysis was carried out by using an Agilent 1290 UPLC coupled to an Agilent 6460 TripleQuad mass spectrometer via an ESI probe. Chromatography was performed on a Waters Acquity BEH300 C18 analytical column (1.7 μm particle size; column dimensions used are 50×2.1 mm for analysis of samples originated from rat species or 100×2.1 mm for analysis of samples originated from monkey species) with pre-filter at a flow rate of 0.30 mL/min (T=60° C.). Water (UPLC grade) containing 0.1% formic acid (v/v) was used as mobile phase A and acetonitrile (UPLC grade) with 0.1% formic acid as mobile phase B.

The gradient system for the analysis of samples originated from rat plasma comprised a linear increase from 0.1% B to 40% B in 7 min. The gradient system for the analysis of samples originated from monkey plasma comprised a linear increase from 8.0% B to 11.0% B in 6 min, followed by a linear increase to 26% B in 4 minutes. Mass analysis was performed in multiple reaction monitoring (MRM) mode, monitoring the transitions m/z 437.2 to 131.0 and m/z 352.3 to 463.0.

Alternatively, quantification of plasma total PTH(1-34) concentrations was performed according to the following procedure:

Plasma total PTH(1-34) concentrations were determined by quantification of a signature peptide close to the N-terminus (sequence: IQLMHNLGK) and a C-terminal signature peptide (sequence: LQDVHNF) after plasma protein precipitation, followed by sequential digestion with Endoproteinase Lys-C (origin: Lysobacter enzymogenes) and Endoproteinase Glu-C (origin: *Staphylococcus aureus* V8) of the supernatant. Subsequently, analysis by reversed phase liquid chromatography and detection by mass spectrometry (RP-HPLC-MS) was performed.

Calibration standards of PTH(1-34) conjugate in blank heparinized plasma were prepared in concentration ranges from 50 to 3000 ng/mL PTH(1-34) eq (dilution with rat plasma) and 1 to 1000 ng/mL PTH(1-34) eq (dilution with monkey plasma).

These solutions were used for the generation of a calibration curve. For quality control, three samples independent from the calibration standard solutions were prepared accordingly. Concentrations at the lower end (3-5 fold concentration of the respective LLOQ), the middle range (0.05-0.1 fold concentration of the respective ULOQ) and the upper end (0.5-0.8 fold concentration of the respective ULOQ).

Sample preparation volumes can be altered depending on the targeted signal response after sample preparation. Processing procedure of the protein precipitation is described here for the analysis of plasma samples originated in rat species. Protein precipitation was carried out by addition of 100 μL of precooled (5-10° C.) methanol to 50 μL of the plasma sample. 60 μL of the supernatant were transferred into a new well-plate and evaporated to dryness (under a gentle nitrogen stream at 45° C.). 60 μL of reconstitution solvent (50 mM Tris 0.5 mM $CaCl_2$) buffer, adjusted to pH 8.0) were used to dissolve the residue. Proteolytic digestion was performed as follows:

20 μg of Lys-C (order number 125-05061, Wako Chemicals GmbH, Neuss, Germany) were dissolved in 80 μL of 10 mM acetic acid. 3 μL of the Lys-C solution were added to each cavity and samples incubated for 15 hours at 37° C. Afterwards 10 μg of Glu-C (order number V1651, Promega GmbH, Mannheim, Germany) were dissolved in 25 μL water, and 1.5 μL of the Glu-C solution added to each cavity and incubation continued for 1.5 hours at 37° C. After incubation samples were acidified with 2 μL water/formic acid 4:6 (v/v) and 10 μL were injected into the UPLC-MS system.

Chromatography was performed on a Waters Acquity BEH300 $C_{18}$ analytical column (1.7 μm particle size; column dimensions 50×2.1 mm). Water (UPLC grade) containing 0.1% formic acid (v/v) was used as mobile phase A and acetonitrile (UPLC grade) with 0.1% formic acid as mobile phase B.

Quantification of Plasma PEG Concentrations:

Plasma total PEG concentrations were determined by quantification of the polymeric part of PTH(1-34) conjugates after plasma protein precipitation and enzymatic digestion of the supernatant. Analysis by size exclusion chromatography and detection by mass spectrometry (SEC-MS) followed.

Calibration standards of PTH(1-34) conjugate in blank heparinized monkey plasma were prepared in concentration ranges from 50 to 1200 ng/mL PEG equivalents.

These solutions were used for the generation of a quadratic calibration curve. Calibration curves were weighted 1/x. For quality control, three samples independent from the calibration standard solutions were prepared accordingly. Concentrations at the lower end (2-4 fold concentration of the LLOQ), the middle range (0.1-0.2 fold concentration of the ULOQ) and the upper end (0.8 fold concentration of the ULOQ). Protein precipitation was carried out by addition of 200 μL of precooled (5-10° C.) methanol to 100 μL of the plasma sample. 180 μL of the supernatant were transferred into a new well-plate and evaporated to dryness (under a gentle nitrogen stream at 45° C.). 50 μL of reconstitution solvent (50 mM Tris 0.5 mM $CaCl_2$) buffer, adjusted to pH 8.0) were used to dissolve the residue. Proteolytic digestion was performed as follows: 20 μg of Lys-C (order number 125-05061, Wako Chemicals GmbH, Neuss, Germany) were dissolved in 80 μL of 10 mM acetic acid. 3 μL of the Lys-C solution were added to each cavity and samples incubated for 15 hours at 37° C. Afterwards 10 μg of Glu-C (order number V1651, Promega GmbH, Mannheim, Germany) were dissolved in 25 μL water, and 1.5 μL of the Glu-C solution added to each cavity and incubation continued for 1.5 hours at 37° C. After incubation samples were acidified with 2 μL water/formic acid 4:6 (v/v) and 5 μL were injected into the SEC-MS system.

SEC-MS analysis was carried out by using an Agilent 1290 UPLC coupled to an Agilent 6460 TripleQuad mass spectrometer via an ESI probe. Acquisition of a distinct precursor ion of the polymer was achieved by applying high voltage in-source fragmentation (200-300V) at the MS interface. Chromatography was performed on a TOSOH TSK Gel SuperAW3000 analytical column (4.0 μm particle size; column dimensions 150×6.0 mm) at a flow rate of 0.50 mL/min (T=65° C.). Water (UPLC grade) containing 0.1% formic acid (v/v) was used as mobile phase A and acetonitrile (UPLC grade) with 0.1% formic acid as mobile phase B. The chromatographic setup for sample analysis comprises an isocratic elution of 50% B over 8 minutes.

Mass analysis was performed in single reaction monitoring (SRM) mode, monitoring the transition m/z 133.1 to 45.1.

Due to the reversible nature of the attachment of -$L^1$- to -D, measurements for PTH receptor activity were made using stable analogs of the PTH prodrugs of the present invention, i.e. they were made using similar structures to those of the PTH prodrugs of the present invention, which instead of a reversible attachment of —Z to -D have a stable attachment.

This was necessary, because the PTH prodrugs of the present invention would release PTH in the course of the experiment and said released PTH would have influenced the result.

Example 1

Synthesis of Linker Reagent 1f

Linker reagent if was synthesized according to the following scheme:

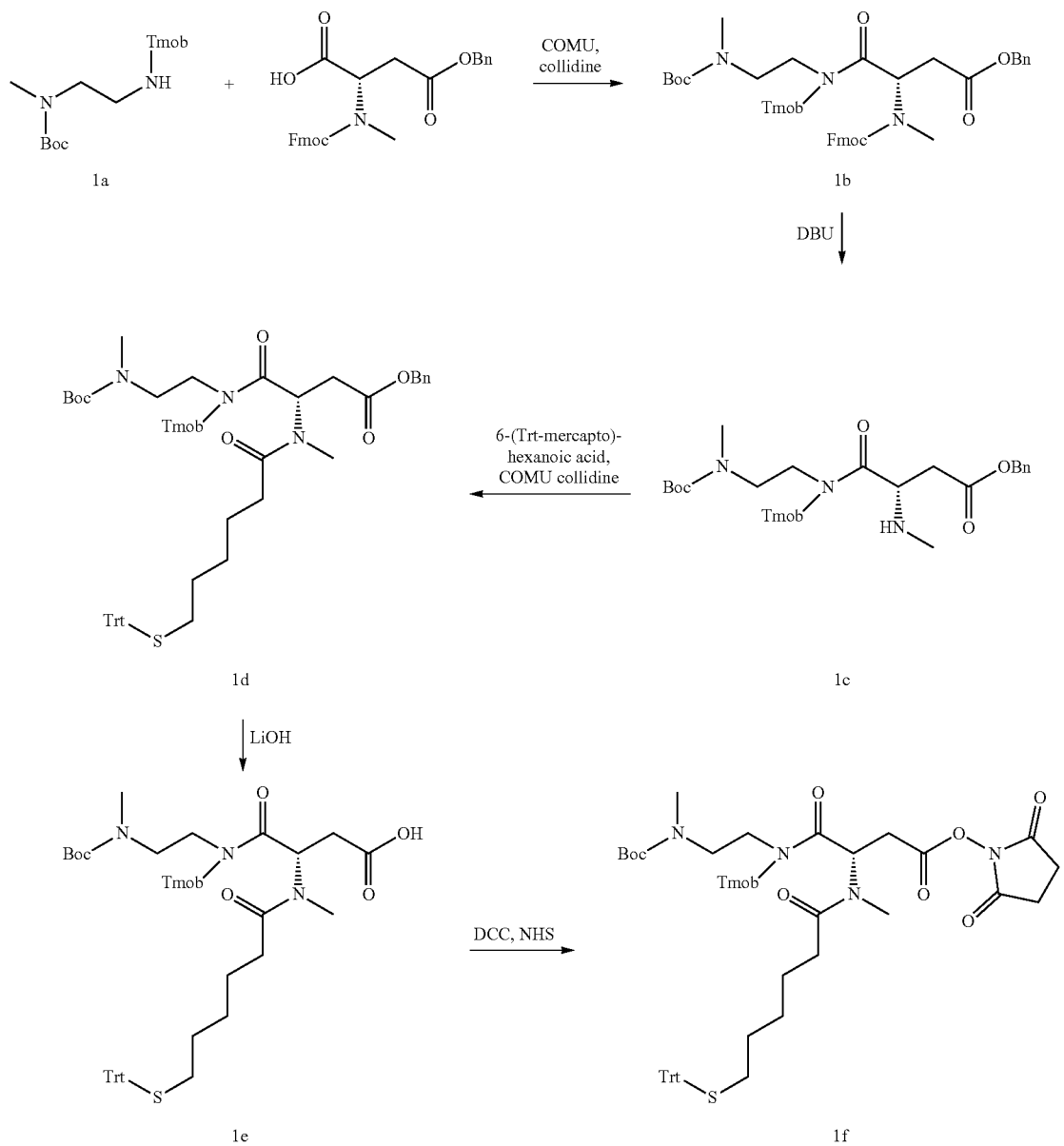

To a solution of N-methyl-N-Boc-ethylenediamine (2 g, 11.48 mmol) and NaCNBH$_3$ (819 mg, 12.63 mmol) in MeOH (20 mL) was added 2,4,6-trimethoxybenzaldehyde (2.08 g, 10.61 mmol) portion wise. The mixture was stirred at rt for 90 min, acidified with 3 M HCl (4 mL) and stirred further 15 min. The reaction mixture was added to saturated NaHCO$_3$ solution (200 mL) and extracted 5× with DCM. The combined organic phases were dried over Na$_2$SO$_4$ and the solvents were evaporated in vacuo. The resulting N-methyl-N-Boc-N'-Tmob-ethylenediamine 1a was dried in high vacuum and used in the next reaction step without further purification.

Yield: 3.76 g (11.48 mmol, 89% purity, 1a: double Tmob protected product=8:1)

MS: m/z 355.22=[M+H]+, (calculated monoisotopic mass=354.21).

To a solution of 1a (2 g, 5.65 mmol) in DCM (24 mL) COMU (4.84 g, 11.3 mmol), N-Fmoc-N-Me-Asp(OBn)-OH (2.08 g, 4.52 mmol) and 2,4,6-collidine (2.65 mL, 20.34 mmol) were added. The reaction mixture was stirred for 3 h at rt, diluted with DCM (250 mL) and washed 3× with 0.1 M H$_2$SO$_4$ (100 mL) and 3× with brine (100 mL). The aqueous phases were re-extracted with DCM (100 mL). The combined organic phases were dried over Na$_2$SO$_4$, filtrated and the residue concentrated to a volume of 24 mL. 1b was purified using flash chromatography.

Yield: 5.31 g (148%, 6.66 mmol)

MS: m/z 796.38=[M+H]$^+$, (calculated monoisotopic mass=795.37).

To a solution of 1b (5.31 g, max. 4.52 mmol ref. to N-Fmoc-N-Me-Asp(OBn)-OH) in THF (60 mL) DBU (1.8 mL, 3% v/v) was added. The solution was stirred for 12 min at rt, diluted with DCM (400 mL) and washed 3× with 0.1 M H$_2$SO$_4$ (150 mL) and 3× with brine (150 mL). The aqueous phases were re-extracted with DCM (100 mL). The combined organic phases were dried over Na$_2$SO$_4$ and filtrated. 1c was isolated upon evaporation of the solvent and used in the next reaction without further purification.

MS: m/z 574.31=[M+H]$^+$, (calculated monoisotopic mass=573.30).

1c (5.31 g, 4.52 mmol, crude) was dissolved in acetonitrile (26 mL) and COMU (3.87 g, 9.04 mmol), 6-tritylmercaptohexanoic acid (2.12 g, 5.42 mmol) and 2,4,6-collidine (2.35 mL, 18.08 mmol) were added. The reaction mixture was stirred for 4 h at rt, diluted with DCM (400 mL) and washed 3× with 0.1 M H$_2$SO$_4$ (100 mL) and 3× with brine (100 mL). The aqueous phases were re-extracted with DCM (100 mL). The combined organic phases were dried over Na$_2$SO$_4$, filtered and 1d was isolated upon evaporation of the solvent. Product 1d was purified using flash chromatography.

Yield: 2.63 g (62%, 94% purity)

MS: m/z 856.41=[M+H]$^+$, (calculated monoisotopic mass=855.41).

To a solution of 1d (2.63 g, 2.78 mmol) in i-PrOH (33 mL) and H$_2$O (11 mL) was added LiOH (267 mg, 11.12 mmol) and the reaction mixture was stirred for 70 min at rt. The mixture was diluted with DCM (200 mL) and washed 3× with 0.1 M H$_2$SO$_4$ (50 mL) and 3× with brine (50 mL). The aqueous phases were re-extracted with DCM (100 mL). The combined organic phases were dried over Na$_2$SO$_4$, filtered and 1e was isolated upon evaporation of the solvent. 1e was purified using flash chromatography.

Yield: 2.1 g (88%)

MS: m/z 878.4=[M+Na]$^+$, (calculated monoisotopic mass=837.40).

To a solution of 1e (170 mg, 0.198 mmol) in anhydrous DCM (4 mL) were added DCC (123 mg, 0.59 mmol), and a catalytic amount of DMAP. After 5 min, N-hydroxysuccinimide (114 mg, 0.99 mmol) was added and the reaction mixture was stirred at rt for 1 h. The reaction mixture was filtered, the solvent was removed in vacuo and the residue was taken up in 90% acetonitrile plus 0.1% TFA (3.4 mL). The crude mixture was purified by RP-HPLC. Product fractions were neutralized with 0.5 M pH 7.4 phosphate buffer and concentrated. The remaining aqueous phase was extracted with DCM and if was isolated upon evaporation of the solvent.

Yield: 154 mg (81%)

MS: m/z 953.4=[M+H]$^+$, (calculated monoisotopic mass=952.43).

Example 2

Synthesis of Linker Reagent 2g

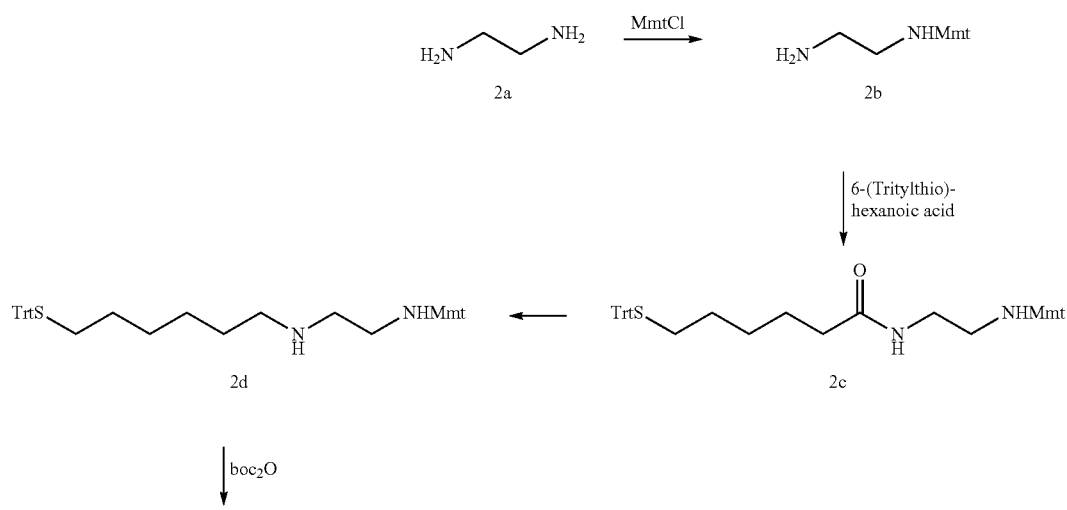

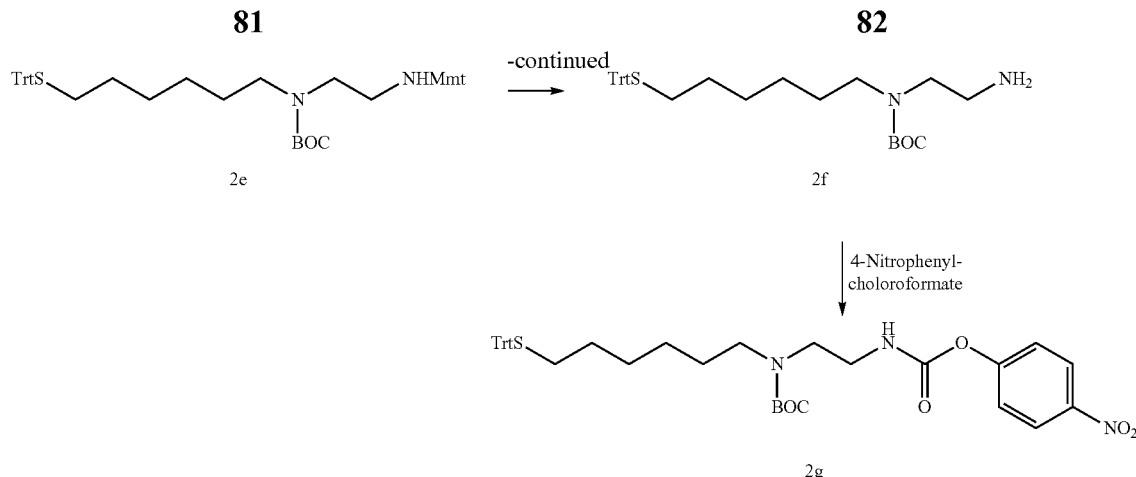

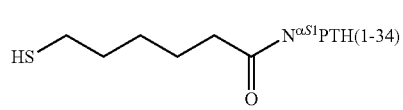

4-Methoxytriphenylmethyl chloride (3.00 g, 9.71 mmol) was dissolved in DCM (20 mL) and added dropwise under stirring to a solution of ethylenediamine 2a (6.5 mL, 97.3 mmol) in DCM (20 mL). The reaction mixture was stirred for 2 h at rt after which it was diluted with diethyl ether (300 mL), washed 3× with brine/0.1 M NaOH 30/1 (v/v) and once with brine. The organic phase was dried over Na$_2$SO$_4$ and 2b was isolated upon evaporation of the solvent.

Yield: 3.18 g (98%)

Mmt protected intermediate 2b (3.18 g, 9.56 mmol) was dissolved in DCM (30 mL). 6-(Tritylthio)-hexanoic acid (4.48 g, 11.5 mmol), PyBOP (5.67 g, 10.9 mmol) and DIPEA (5.0 mL, 28.6 mmol) were added and the mixture was stirred for 30 min at rt. The solution was diluted with diethyl ether (250 mL), washed 3× with brine/0.1 M NaOH 30/1 (v/v) and once with brine. The organic phase was dried over Na$_2$SO$_4$ and the solvent was removed in vacuo. 2c was purified using flash chromatography.

Yield: 5.69 g (85%)

MS: m/z 705.4=[M+H]$^+$, (calculated monoisotopic mass=704.34).

Compound 2c (3.19 g, 4.53 mmol) was dissolved in abhydrous THF (50 mL), 1 M BH$_3$·THF solution in THF (8.5 mL, 8.5 mmol) was added and the mixture was stirred for 16 h at rt. More 1 M BH$_3$·THF solution in THF (14 mL, 14.0 mmol) was added and the mixture was stirred for further 16 h at rt. Methanol (8.5 mL) and N,N'-dimethyl-ethylendiamine (3.00 mL, 27.9 mmol) were added and the mixture was heated under reflux for 3 h. The mixture was allowed to cool down and ethyl acetate (300 mL) was added. The solution was washed 2× with aqueous Na$_2$CO$_3$ and 2× with aqueous NaHCO$_3$. The organic phase was dried over Na$_2$SO$_4$ and the solvent was removed in vacuo to obtain 2d.

Yield: 3.22 g (103%)

MS: m/z 691.4=[M+H]$^+$, (calculated monoisotopic mass=690.36).

Di-tert-butyl dicarbonate (2.32 g, 10.6 mmol) and DIPEA (3.09 mL, 17.7 mmol) were dissolved in DCM (5 mL) and added to a solution of 2d (2.45 g, 3.55 mmol) in DCM (5 mL). The mixture was stirred for 30 min at rt. The solution was concentrated in vacuo and purified by flash chromatography to obtain product 2e.

Yield: 2.09 g (74%)

MS: m/z 791.4=[M+H]$^+$, (calculated monoisotopic mass=790.42).

Compound 2e (5.01 g, 6.34 mmol) was dissolved in acetonitrile (80 mL). 0.4 M aqueous HCl (80 mL) followed by acetonitrile (20 mL) was added and the mixture was stirred for 1 h at rt. The pH was adjusted to pH 5.5 by addition of aqueous 5 M NaOH. The organic solvent was removed in vacuo and the remaining aqueous solution was extracted 4× with DCM. The combined organic phases were dried over Na$_2$SO$_4$ and the solvent was removed in vacuo to obtain product 2f.

Yield: 4.77 g (95%)

MS: m/z 519.3=[M+H]$^+$, (calculated monoisotopic mass=518.30).

Compound 2f (5.27 g, 6.65 mmol) was dissolved in DCM (30 mL) and added to a solution of p-nitrophenyl chloroformate (2.01 g, 9.98 mmol) in DCM (25 mL). 2,4,6-trimethylpyridine (4.38 mL, 33.3 mmol) was added and the solution was stirred for 45 min at rt. The solution was concentrated in vacu and purified by flash chromatography to obtain product 2g.

Yield: 4.04 g (89%)

MS: m/z 706.32=[M+Na]$^+$, (calculated monoisotopic mass=683.30).

Example 3

Synthesis of Permanent S1 PTH(1-34) Conjugate 3

Side chain protected PTH(1-34) on TCP resin having Fmoc protected N-terminus was Fmoc deprotected according to the procedure given in Materials and Methods. A solution of 6-tritylmercaptohexanoic acid (62.5 mg, 160 μmol), PyBOP (80.1 mg, 154 μmol) and DIPEA (53 μL, 306 μmol) in DMF (2 mL) was added to 0.21 g (51 μmol) of the resin. The suspension was agitated for 80 min at rt. The resin was washed 10× with DMF, 10× with DCM and dried in vacuo. Cleavage of the peptide from the resin and removal of protecting groups was achieved by adding 10 mL cleavage cocktail 100/3/3/2/1 (v/w/v/v/v) TFA/DTT/TES/water/thioanisole and agitating the suspension for 1 h at rt. Crude 3 was precipitated in pre-cooled diethyl ether (−18° C.). The precipitate was dissolved in ACN/water and purified by RP-HPLC. The product fractions were freeze-dried.

Yield: 36 mg (14%), 3*8 TFA

MS: m/z 1062.31=[M+4H]$^{4+}$, (calculated monoisotopic mass for [M+4H]$^{4+}$=1062.30).

Example 4

Synthesis of Permanent K26 PTH(1-34) Conjugate 4

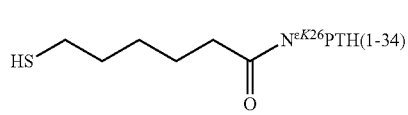

4

Side chain protected PTH(1-34) on TCP resin having Boc protected N-terminus and ivDde protected side chain of Lys26 was ivDde deprotected according to the procedure given in Materials and Methods. A solution of 6-tritylmercaptohexanoic acid (107 mg, 273 µmol), PyBOP (141 mg, 273 µmol) and DIPEA (95 µL, 545 µmol) in DMF (3 mL) was added to 0.80 g (90.9 µmol) of the resin. The suspension was agitated for 1 h at rt. The resin was washed 10× with DMF, 10× with DCM and dried in vacuo. Cleavage of the peptide from the resin and removal of protecting groups was achieved by adding 6 mL cleavage cocktail 100/3/3/2/1 (v/w/v/v/v) TFA/DTT/TES/water/thioanisole and agitating the suspension for 1 h at rt. Crude 4 was precipitated in pre-cooled diethyl ether (−18° C.). The precipitate was dissolved in ACN/water and purified by RP-HPLC. The product fractions were freeze-dried.

Yield: 40 mg (8%), 4*8 TFA

MS: m/z 1062.30=[M+4H]$^{4+}$, (calculated monoisotopic mass for [M+4H]$^{4+}$=1062.30).

Example 5

Synthesis of Transient S1 PTH(1-34) Conjugate

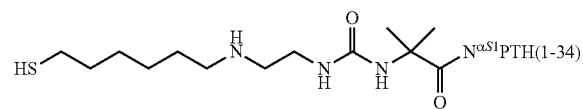

5

Side chain protected PTH(1-34) on TCP resin having Fmoc protected N-terminus was Fmoc deprotected according to the procedure given in Materials and Methods. A solution of Fmoc-Aib-OH (79 mg, 244 µmol), PyBOP (127 mg, 244 µmol) and DIPEA (64 µL, 365 µmol) in DMF (1.5 mL) was added to 0.60 g (61 µmol) of the resin. The suspension was agitated for 16 h at rt. The resin was washed 10× with DMF and Fmoc-deprotected as described above. A solution of 2g (167 mg, 244 µmol) and DIPEA (64 µL, 365 µmol) in DMF (1.5 mL) was added to the resin. The suspension was agitated for 24 h at rt. The resin was washed 10× with DMF, 10× with DCM and dried in vacuo. Cleavage of the peptide from the resin and removal of protecting groups was achieved by adding 7 mL cleavage cocktail 100/3/3/2/1 (v/w/v/v/v) TFA/DTT/TES/water/thioanisole and agitating the suspension for 1 h at rt. Crude 5 was precipitated in pre-cooled diethyl ether (−18° C.). The precipitate was dissolved in ACN/water and purified by RP-HPLC. The product fractions were freeze-dried.

Yield: 78 mg (24%), 5*9 TFA

MS: m/z 1101.59=[M+4H]$^{4+}$, (calculated monoisotopic mass for [M+4H]$^{4+}$=1101.57).

Example 6

Synthesis of Transient S1 PTH(1-34) Conjugate 6

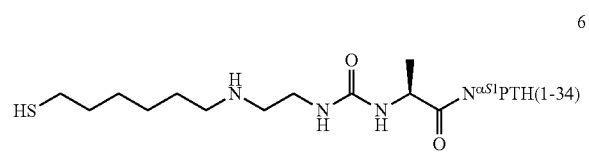

6

Side chain protected PTH(1-34) on TCP resin having Fmoc protected N-terminus was Fmoc deprotected according to the procedure given in Materials and Methods. A solution of Fmoc-Ala-OH (32 mg, 102 µmol), PyBOP (53 mg, 102 µmol) and DIPEA (27 µL, 152 µmol) in DMF (3 mL) was added to 0.25 g (25 µmol) of the resin. The suspension was shaken for 1 h at rt. The resin was washed 10× with DMF, 10× with DCM and dried under vacuum. Fmoc-deprotection was performed as described above. A solution of 2g (69 mg, 102 µmol) and DIPEA (27 µL, 152 µmol) in DMF (3 mL) was added to the resin. The suspension was agitated for 1.5 h at rt. The resin was washed 10× with DMF, 10× with DCM and dried in vacuo. Cleavage of the peptide from the resin and removal of protecting groups was achieved by adding 3 mL cleavage cocktail 100/3/3/2/1 (v/w/v/v/v) TFA/DTT/TES/water/thioanisole and agitating the suspension for 1 h at rt. Crude 6 was precipitated in pre-cooled diethyl ether (−18° C.). The precipitate was dissolved in ACN/water and purified by RP-HPLC. The product fractions were freeze-dried.

Yield: 25 mg (18%), 6*9 TFA

MS: m/z 1098.75=[M+4H]$^{4+}$, (calculated monoisotopic mass for [M+4H]$^{4+}$=1098.07).

Example 7

Synthesis of Transient S1 PTH(1-34) Conjugate 7

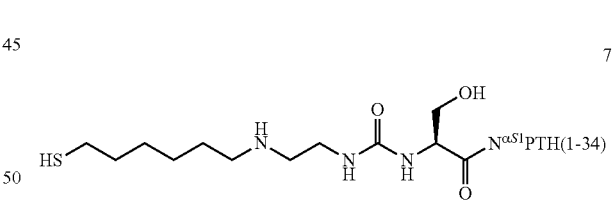

7

Side chain protected PTH(1-34) on TCP resin having Fmoc protected N-terminus was Fmoc deprotected according to the procedure given in Materials and Methods. A solution of Fmoc-Ser(Trt)-OH (117 mg, 205 µmol), PyBOP (108 mg, 207 µmol) and DIPEA (53 µL, 305 µmol) in DMF (2 mL) was added to 0.50 g (51 µmol) of the resin. The suspension was agitated for 1 h at rt. The resin was washed 10× with DMF, 10× with DCM and dried under vacuum. Fmoc-deprotection was performed as described above. A solution of 2g (144 mg, 211 µmol) and DIPEA (53 µL, 305 µmol) in DMF (1.8 mL) was added to the resin. The suspension was shaken for 7 h at rt. The resin was washed 10× with DMF, 10× with DCM and dried in vacuo. Cleavage of the peptide from the resin and removal of protecting groups was achieved by adding 6 mL cleavage cocktail 100/3/3/2/1 (v/w/v/v/v) TFA/DTT/TES/water/thioanisole and agitating the suspension for 1 h at rt. Crude 7 was precipitated in pre-cooled diethyl ether (−18° C.). The precipitate was dissolved in ACN/water and purified by RP-HPLC. The product fractions were freeze-dried.

Yield: 54 mg (20%), 7*9 TFA

MS: m/z 1102.08=[M+4H]$^{4+}$, (calculated monoisotopic mass for [M+4H]$^{4+}$=1102.07).

Example 8

Synthesis of Transient S1 PTH(1-34) Conjugate 8

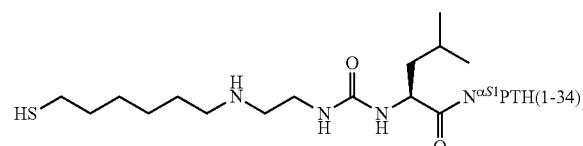

8

Side chain protected PTH(1-34) on TCP resin having Fmoc protected N-terminus was Fmoc deprotected according to the procedure given in Materials and Methods. A solution of Fmoc-Leu-OH (36 mg, 102 µmol), PyBOP (53 mg, 102 µmol) and DIPEA (27 µL, 152 µmol) in DMF (3 mL) was added to 0.25 g (25 µmol) of the resin. The suspension was agitated for 1 h at rt. The resin was washed 10× with DMF, 10× with DCM and dried under vacuum. Fmoc-deprotection was performed as described above. A solution of 2g (69 mg, 102 µmol) and DIPEA (27 µL, 152 µmol) in DMF (3 mL) was added to the resin. The suspension was agitated for 1.5 h at rt. The resin was washed 10× with DMF, 10× with DCM and dried in vacuo. Cleavage of the peptide from the resin and removal of protecting groups was achieved by adding 3 mL cleavage cocktail 100/3/3/2/1 (v/w/v/v/v) TFA/DTT/TES/water/thioanisole and agitating the suspension for 1 h at rt. Crude 8 was precipitated in pre-cooled diethyl ether (−18° C.). The precipitate was dissolved in ACN/water and purified by RP-HPLC. The product fractions were freeze-dried.

Yield: 31 mg (22%), 8*9 TFA

MS: m/z 1109.32=[M+4H]$^{4+}$, (calculated monoisotopic mass for [M+4H]$^{4+}$=1108.58).

Example 9

Synthesis of Transient S1 PTH(1-34) Conjugate 9

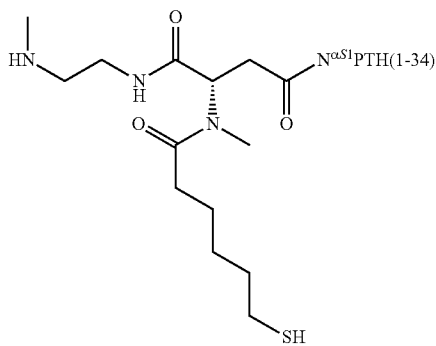

9

Side chain protected PTH(1-34) on TCP resin having Fmoc protected N-terminus was Fmoc deprotected according to the procedure given in Materials and Methods. A solution of 1e (182 mg, 213 µmol), PyBOP (111 mg, 213 µmol) and DIPEA (93 µL, 532 µmol) in DMF (5 mL) was added to 2.00 g (107 µmol) of the resin. The suspension was agitated for 16 h at rt. The resin was washed 10× with DMF, 10× with DCM and dried under vacuum. Cleavage of the peptide from the resin and removal of protecting groups was achieved by adding 20 mL cleavage cocktail 100/3/3/2/1 (v/w/v/v/v) TFA/DTT/TES/water/thioanisole and agitating the suspension for 1 h at rt. Crude 9 was precipitated in pre-cooled diethyl ether (−18° C.). The precipitate was dissolved in ACN/water and purified by RP-HPLC. The product fractions were freeze-dried.

Yield: 47 mg (8%), 9*9 TFA

MS: m/z 1108.58=[M+4H]$^{4+}$, (calculated monoisotopic mass for [M+4H]$^{4+}$=1108.57).

Example 10

Synthesis of Transient K26 PTH(1-34) Conjugate 10

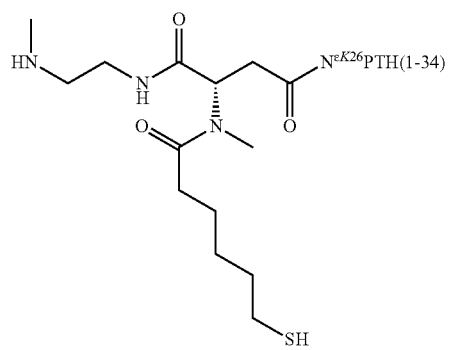

10

Side chain protected PTH(1-34) on TCP resin having Boc protected N-terminus and ivDde protected side chain of Lys26 was ivDde deprotected according to the procedure given in Materials and Methods. A solution of 1f (867 mg, 910 µmol) and DIPEA (0.24 mL, 1.36 mmol) in DMF (5 mL) was added to 1.91 g (227 µmol) of the resin. The suspension was agitated for 1 h at rt. The resin was washed 10× with DMF, 10× with DCM and dried under vacuum. Cleavage of the peptide from the resin and removal of protecting groups was achieved by adding 20 mL cleavage cocktail 100/3/3/2/1 (v/w/v/v/v) TFA/DTT/TES/water/thioanisole and shaking the suspension for 1 h at rt. Crude 10 was precipitated in pre-cooled diethyl ether (−18° C.). The precipitate was dissolved in ACN/water and purified by RP-HPLC. The product fractions were freeze-dried.

Yield: 92 mg (7%), 10*9 TFA

MS: m/z 1108.58=[M+4H]$^{4+}$, (calculated monoisotopic mass for [M+4H]$^{4+}$=1108.57).

Example 11

Synthesis of Low Molecular Weight Transient S1 PEG Conjugate 11b

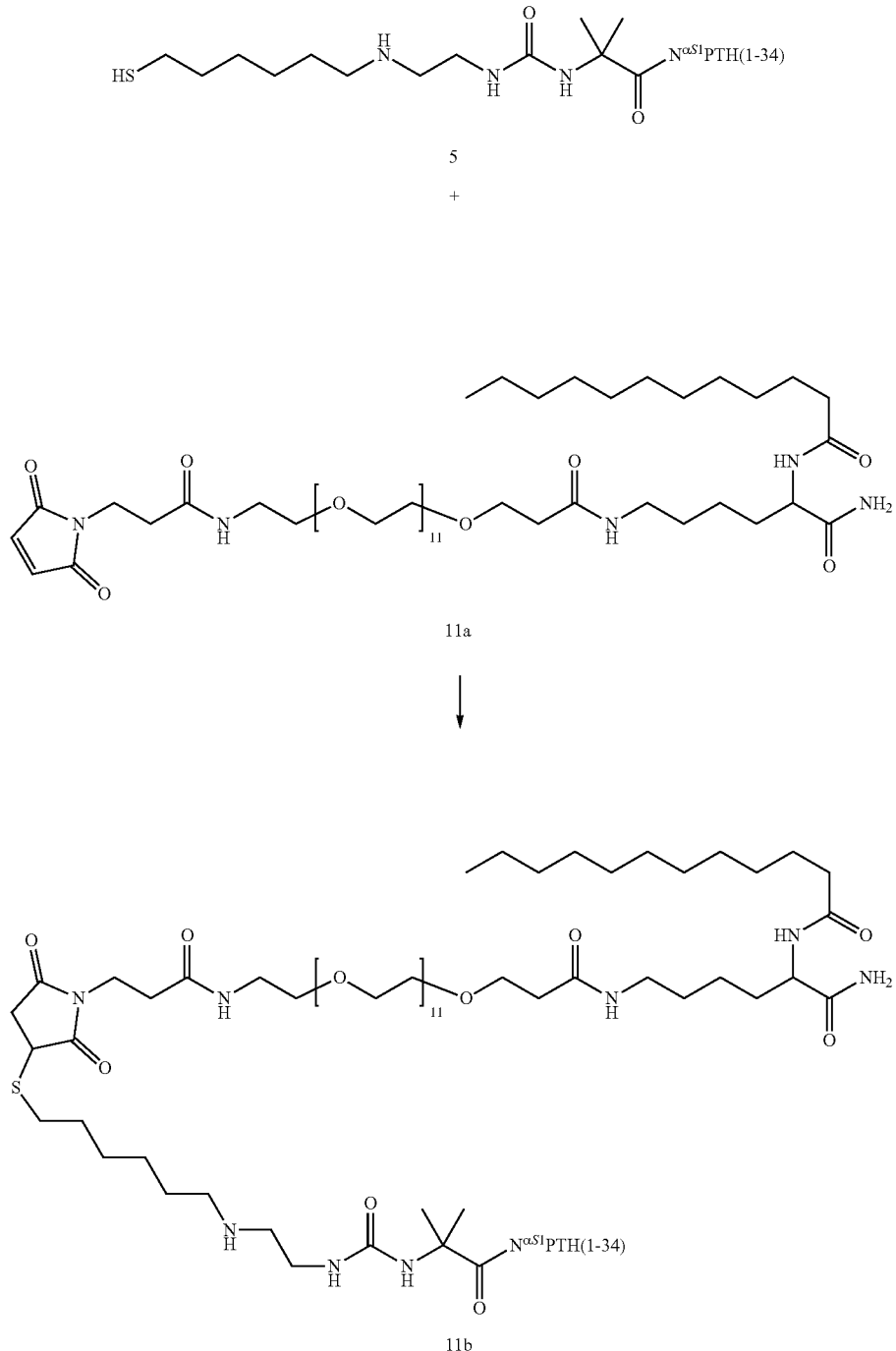

0.15 mL of a 0.5 M NaH$_2$PO$_4$ buffer (pH 7.4) was added to 0.5 mL of a 20 mg/mL solution of thiol 5 (10 mg, 1.84 µmol) in 1/1 (v/v) acetonitrile/water containing 0.1% TFA (v/v). The solution was incubated at rt for 10 min after which 238 µL of a 10 mg/mL solution of maleimide 11a (2.4 mg, 2.21 µmol) in 1/1 (v/v) acetonitrile/water containing 0.1% TFA (v/v) were added. The solution was incubated for 20 min at rt. 10 µL TFA was added and the mixture was purified by RP-HPLC. The product fractions were freeze-dried to obtain 11b.

Yield: 3.1 mg (26%), 11b*9 TFA

MS: m/z 1097.00=[M+4H]$^{4+}$, (calculated monoisotopic mass for [M+5H]$^{5+}$=1096.99).

Example 12

Synthesis of Low Molecular Weight Transient S1 PEG Conjugate 12

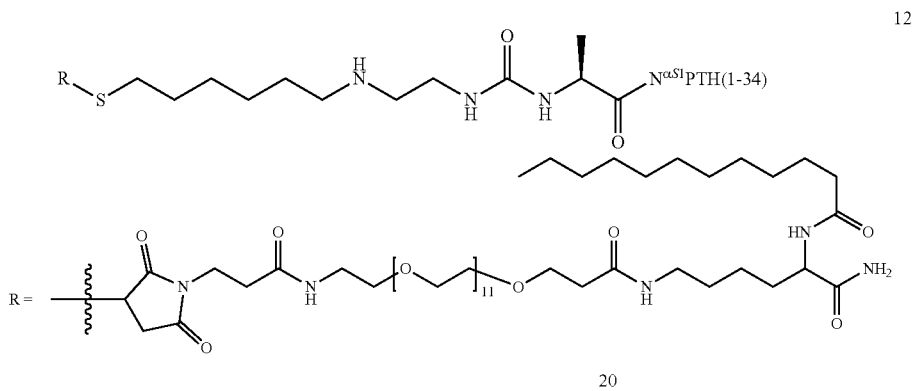

12

Conjugate 12 was synthesized as described for 11b by using thiol 6 (10 mg, 1.85 μmol) and maleimide 11a (2.4 mg, 2.21 μmol).

Yield: 10 mg (83%), 12*9 TFA

MS: m/z 1094.20=$[M+4H]^{4+}$, (calculated monoisotopic mass for $[M+4H]^{4+}$=1094.19).

Example 13

Synthesis of Low Molecular Weight Transient S1 PEG Conjugate 13

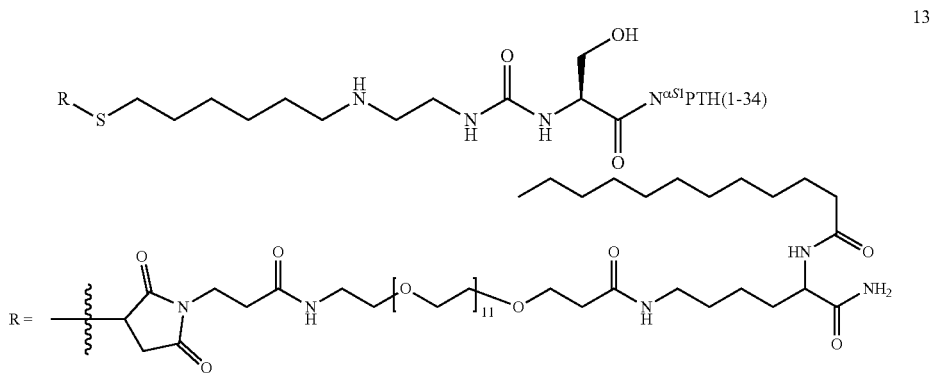

13

Conjugate 13 was synthesized as described for 11b by using thiol 7 (10 mg, 1.84 μmol) and maleimide 11a (2.4 mg, 2.21 μmol).

Yield: 8 mg (67%), 13*9 TFA

MS: m/z 1097.40=$[M+5H]^{5+}$, (calculated monoisotopic mass for $[M+5H]^{5+}$=1097.39).

Example 14

Synthesis of Low Molecular Weight Transient S1 PEG Conjugate 14

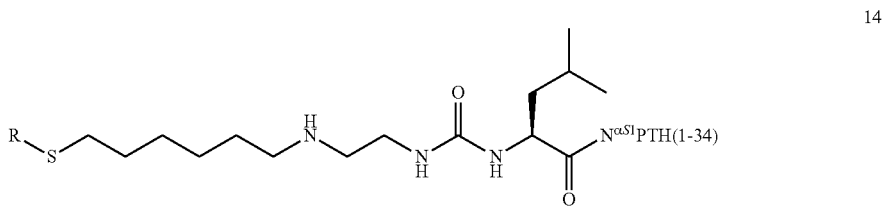

14

-continued

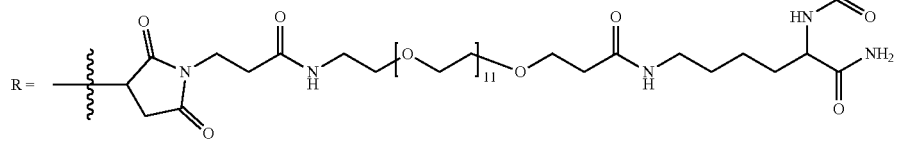

R =

Conjugate 14 was synthesized as described for 11b by using thiol 8 (10 mg, 1.83 μmol) and maleimide 11a (2.4 mg, 2.21 μmol).

Yield: 4 mg (33%), 14*9 TFA

MS: m/z 1378.01=$[M+4H]^{4+}$, (calculated monoisotopic mass for $[M+4H]^{4+}$=1378.00).

Example 15

Synthesis of Low Molecular Weight Transient K26 PEG Conjugate 15

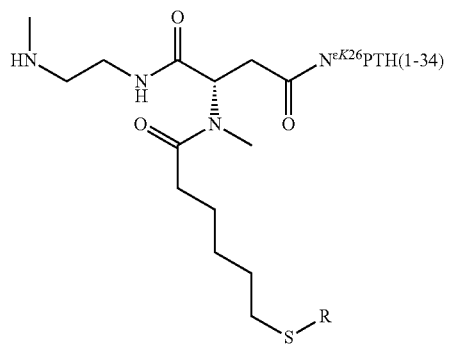

R =

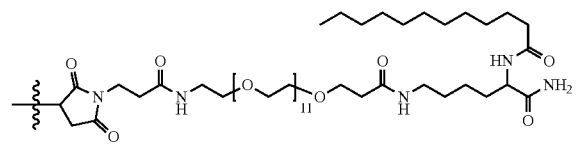

Conjugate 15 was synthesized as described for 11b by using thiol 10 (5.2 mg, 0.95 μmol) and maleimide 11a (1.23 mg, 1.14 μmol).

Yield: 2.1 mg (33%), 15*9 TFA

MS: m/z 1102.60=$[M+5H]^{5+}$, (calculated monoisotopic mass for $[M+5H]^{5+}$=1102.59).

Example 16

Synthesis of Permanent 2×20 kDa S1 PEG Conjugate 16

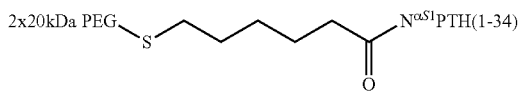

772 μL of a solution containing thiol 3 (19.4 mg/mL, 15 mg, 3.54 μmol) and 2.5 mg/mL Boc-L-Met in 1/1 (v/v) acetonitrile/water containing 0.1% TFA (v/v) were added to 1.87 mL of a solution containing PEG 2×20 kDa maleimide (Sunbright GL2-400MA, 187 mg, 4.32 μmol) and 2.5 mg/mL Boc-L-Met in water containing 0.1% TFA (v/v). 0.5 M $NaH_2PO_4$ buffer (0.66 mL, pH 7.0) was added and the mixture was stirred for 30 min at rt. 10 μL of a 270 mg/mL solution of 2-mercaptoethanol in water was added. The mixture was stirred for 5 min at rt and 0.33 mL 1 M HCl were added. Conjugate 16 was purified by IEX followed by RP-HPLC using a linear gradient of solvent system A (water containing 0.1% AcOH v/v) and solvent system B (acetonitrile containing 0.1% AcOH v/v). The product containing fractions were freeze-dried.

Yield: 97 mg (2.01 μmol, 57%) conjugate 16*8 AcOH

Example 17

Synthesis of Permanent 2×20 kDa K26 PEG Conjugate 17

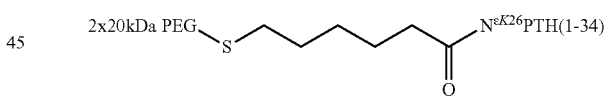

Conjugate 17 was prepared as described for 16 by reaction of thiol 4 (15 mg, 3.53 μmol) and PEG 2×20 kDa maleimide (Sunbright GL2-400MA, 187 mg, 4.32 μmol).

Yield: 80 mg (1.79 μmol, 51%) conjugate 17*8 AcOH

Example 18

Synthesis of Transient 2×20 kDa S1 PEG Conjugate 18

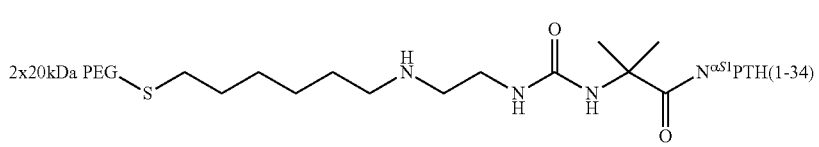

Conjugate 18 was prepared as described for 16 by reaction of thiol 5 (37 mg, 8.40 μmol) and PEG 2×20 kDa maleimide (Sunbright GL2-400MA, 445 mg, 9.24 μmol). The reaction was quenched by addition of 50 μL TFA without prior addition of 2-mercaptoethanol. Conjugate 18 was purified by IEX followed by SEC for desalting. The product containing fractions were freeze-dried.

Yield: 161 mg (3.33 μmol, 40%) conjugate 18*9 AcOH

Example 19

Synthesis of Transient 2×20 kDa S1 PEG Conjugate 19

Conjugate 20 was prepared as described for 16 by reaction of thiol 9 (38 mg, 8.59 μmol) and PEG 2×20 kDa maleimide (Sunbright GL2-400MA, 455 mg, 9.45 μmol). The reaction was quenched by addition of 50 μL TFA without prior addition of 2-mercaptoethanol. Conjugate was purified by IEX followed by SEC for desalting. The product containing fractions were freeze-dried.

Yield: 194 mg (4.01 μmol, 47%) conjugate 20*9 AcOH

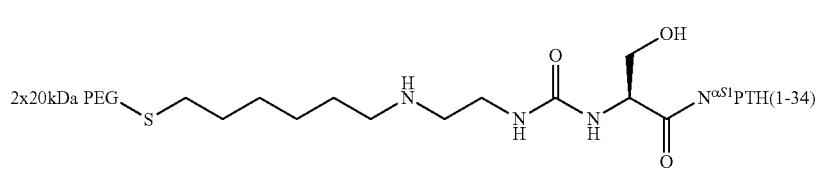

Conjugate 19 was prepared as described for 16 by reaction of thiol 7 (27 mg, 6.14 μmol) and PEG 2×20 kDa maleimide (Sunbright GL2-400MA, 325 mg, 7.50 μmol).

Yield: 249 mg (5.16 μmol, 84%) conjugate 19*9 AcOH

Example 20

Synthesis of Transient 2×20 kDa S1 PEG Conjugate 20

Example 21

Synthesis of Transient 2×20 kDa K26 PEG Conjugate 21

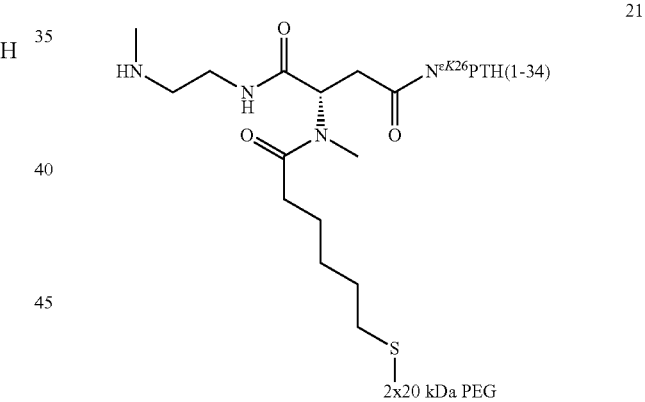

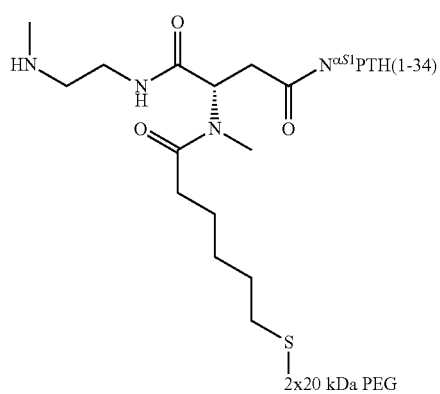

Conjugate 21 was prepared as described for 16 by reaction of thiol 10 (34 mg, 7.58 μmol) and PEG 2×20 kDa maleimide (Sunbright GL2-400MA, 401 mg, 9.26 μmol).

Yield: 256 mg (5.30 μmol, 70%) conjugate 21*9 AcOH

Example 22

In Vitro Release Kinetics of Transient Low Molecular Weight PEG Conjugates

Conjugates 11b, 12, 13, 14, and 15 were dissolved in pH 7.4 phosphate buffer (60 mM NaH$_2$PO$_4$, 3 mM EDTA, 0.01% Tween-20, adjusted to pH 7.4 by NaOH) containing 0.05 mg/mL pentafluorophenol as internal standard at a concentration of approximately 1 mg conjugate/mL. The solutions were filtered sterile and incubated at 37° C. At time points, aliquots were withdrawn and analysed by RP-HPLC and ESI-MS. The fraction of released PTH at a particular time point was calculated from the ratio of UV peak areas of liberated PTH and PEG conjugate. The % released PTH was plotted against incubation time. Curve-fitting software was applied to calculate the corresponding half times of release.
Results:

For conjugate 11b a release half life time of 3.2 d was obtained.

For conjugate 12 a release half life time of 8.7 d was obtained.

For conjugate 13 a release half life time of 10.8 d was obtained.

For conjugate 14 a release half life time of 25.3 d was obtained.

For conjugate 15 a release half life time of 6.9 d was obtained.

Example 23

In Vitro Release Kinetics of Transient 2×20 kDa PEG Conjugates

Conjugates 18, 19, 20, and 21 were dissolved in pH 7.4 phosphate buffer (60 mM NaH$_2$PO$_4$, 3 mM EDTA, 0.01% Tween-20, adjusted to pH 7.4 by NaOH) containing 0.08 mg/mL pentafluorophenol as internal standard at a concentration of approximately 5 mg conjugate/mL.

The solutions were filtered sterile and incubated at 37° C. At time points, aliquots were withdrawn and analysed by RP-HPLC. The fraction of released PTH at a particular time point was calculated from the ratio of UV peak areas of liberated PTH and PEG conjugate. The % released PTH was plotted against incubation time. Curve-fitting software was applied to calculate the corresponding half times of release.
Results:

For conjugate 18 a release half life time of 2.8 d was obtained.

For conjugate 19 a release half life time of 13.4 d was obtained.

For conjugate 20 a release half life time of 1.3 d was obtained.

For conjugate 21 a release half life time of 7.1 d was obtained.

Example 24

PTH Receptor Activity of Permanent 2×20 kDa PEG Conjugates 16 and 17 in Cell Based Assay The residual PTH activity of permanently PEGylated conjugates 16 and 17 was quantified by measuring cAMP production from HEK293 cells over-expressing the PTH/PTHrP1 receptor (Hohenstein A, Hebell M, Zikry H, El Ghazaly M, Mueller F, Rohde, J. Development and validation of a novel cell-based assay for potency determination of human parathyroid hormone (PTH), Journal of Pharmaceutical and Biomedical Analysis September 2014, 98: 345-350). PTH(1-34) from NIBSC (National Institute for Biological Standards and Control, UK) was used as reference standard.
Results:

For conjugate 16 a receptor activity of 0.12% was found relative to PTH(1-34) reference. For conjugate 17 a receptor activity of 0.11% was found relative to PTH(1-34) reference.

The results indicate an effective lowering of receptor activity in the permanent 2×20 kDa PEG conjugates 16 and 17. It can be concluded that similar conjugates with transiently Ser1 or Lys26 linked PTH (like e.g. 18 and 21) are suitable PTH prodrugs providing low residual receptor activity. Direct analysis of transient conjugates in the cell assay is not possible due to linker cleavage under the assay conditions. The released PTH would influence the assay result.

Example 25

Pharmacokinetic Study of Permanent 2×20 kDa PEG Conjugates 16 and 17 in Rats

Male Wistar rats (6 weeks, 230-260 g) received either a single intravenous (2 groups, n=3 animals each) or a single subcutaneous (2 groups, n=3 animals each) administration of 16 or 17 at doses of 29 μg/rat PTH$_{eq}$ and 31 μg/rat PTH$_{eq}$ respectively. Blood samples were collected up to 168 h post dose, and plasma was generated. Plasma PTH(1-34) concentrations were determined by quantification of the N-terminal signature peptide (sequence: IQLMHNLGK (SEQ ID NO:123)) and the C-terminal signature peptide (sequence: LQDVHNF (SEQ ID NO: 124)) after LysC and GluC digestion as described in Materials and Methods.

Results: Dose administrations were well tolerated with no visible signs of discomfort during administration and following administration. No dose site reactions were observed any time throughout the study. After intraveneous injection of 16 and 17 the total PTH(1-34) $t_{max}$ was observed at 15 min (earliest time point analyzed), followed by a slow decay in total PTH(1-34) content with a half life time of approx. 13 h and 11 h respectively. After subcutaneous injection the total PTH(1-34) concentration peaked at a $t_{max}$ of 24 h for both 16 and 17, followed by a slow decay in total PTH(1-34) content with half life times of approx. 1.5 days for both conjugates. The bioavailability was approx. 40% and 60% respectively. Similar PK curves were obtained for the N- and the C-terminal signature peptide up to 168 h post dose, indicating the presence of intact PTH(1-34) in the conjugate.

The favourable long lasting PK and the stability of PTH in the conjugates indicate the suitability of the permanent 2×20 kDa PEG model compounds as slow releasing PTH prodrugs after subcutaneous injection. It can be concluded that similar conjugates with transiently Ser1 (like e.g. 18) or Lys26 linked PTH are suitable PTH prodrugs providing long lasting levels of released bioactive PTH.

Example 26

Pharmacokinetic Study of Transient 2×20 kDa S1 PEG Conjugate 19 in Cynomolgus Monkeys Male non naïve cynomolgus monkeys (2-4 years, 3.7-5.4 kg) received a single subcutaneous (n=3 animals) administration of 19 at a dose of 70 μg/kg PTH$_{eq}$. Blood samples were collected up to 504 h post dose, and plasma was generated. Total plasma PTH(1-34) concentrations were determined by quantification of the N-terminal signature peptide (sequence: IQLMHNLGK (SEQ ID NO:123)) and the C-terminal signature peptide (sequence: LQDVHNF (SEQ ID NO: 124)) after LysC and GluC digestion as described in Materials and Methods. The PEG concentrations were determined using the method described in Materials and Methods.

Results: Dose administrations were well tolerated with no visible signs of discomfort during administration. One animal showed showed visible signs of discomfort 72 h post dose, but recovered the days after. No dose site reactions were observed any time throughout the study. The total PTH(1-34) concentration peaked at a $t_{max}$ of 24 h, followed by a slow decay in total PTH(1-34) content with a half life time of approx. 2.5 d for the N-terminal signature peptide and 0.9 d for the C-terminal signature peptide. The PEG concentration peaked at $t_{max}$ of 24 h, followed by a slow decay in PEG concentration with a half life time of 3.5 d.

It can be concluded that conjugate 19 is a suitable prodrug for sustained delivery of PTH.

Example 27

Pharmacokinetic Study of Transient 2×20 kDa S1 PEG Conjugate 18 in Cynomolgus Monkeys Non naïve cynomolgus monkeys (2-3 years, 2.5-4 kg) received daily subcutaneous (n=2 animals - 1 male/1 female) administration of 18 at dose levels of 0.2, 0.5, and 1 μg/kg $PTH_{eq}$ for 28 days. Blood samples were collected up to 28 days (at days 1, 13, and, 27 samples were collected at pre-dose, 2 h, 4 h, 8 h, 12 h, and 24 h post-dose) and plasma was generated. Plasma PTH(1-34) concentrations were determined by quantification of the N-terminal signature peptide (sequence: IQLMHNLGK (SEQ ID NO:123)) and the C-terminal signature peptide (sequence: LQDVHNF (SEQ ID NO:124)) after LysC and GluC digestion as described in Materials and Methods.

Results: All dose administrations were performed without incident. No dose site reactions were observed any time throughout the study. Dose linearity was observed in the three groups. Dose stacking was observed from day 1 compared with day 13 and day 27. Total PTH(1-34) concentrations were quantified via the N-terminal signature peptide (sequence: IQLMHNLGK (SEQ ID NO: 123)) at steady state (during day 27).

A low peak-to-trough ratio of total PTH(1-34) for all dose groups of below 3 was observed after daily subcutaneous application at steady state in cynomolgus monkeys. As free peptide concentrations at steady state are correlated to total PTH(1-34) concentration, the peak-to-trough ratio for the free peptide is below 4 in cynomolgus monkeys.

Example 28

Pharmacodynamic Actions in Thyroparathyroidectomised (TPTx) Rats During a 28-Days Study with Daily Subcutaneous Injections with Conjugate 18 or PTH(1-84)

This study was performed in order to test and compare the effect of daily subcutaneous injection of compound 18 and PTH(1-84), the current standard of care, in an animal disease model relevant for investigating treatment of hypoparathyroidism (HP). Rats subjected to thyroparathyroidectomy (TPTx) by blunt dissection are unable to produce parathyroid hormone, PTH, the major regulator of calcium homeostasis. Hence, TPTx rats develop hypocalcemia and hyperphosphatemia characteristic of HP. 17 weeks old female SD TPTx rats (n=9/group) were dosed subcutaneously for 28 days with compound 18 (5 μg PTH eq/kg/d; 1.2 nmol/kg/d, in 10 mM succinic acid, 46 g/L mannitol, pH 4.0), PTH(1-84) (70 μg PTH eq/kg/d; 7.3 nmol/kg/d; in 10 mM citrate, mannitol 39.0 g/L, pH 5.0) or vehicle. Additionally, one group of sham operated rats (n=9) representing normophysiological background control were also given vehicle. Serum calcium (sCa) and phosporous (sP) levels in the animals were measured pre- and post-dose on days 1, 6, 12 and 27. Moreover, bone turnover markers (P1NP and CTx) were measured and bone quality assessed by ex vivo pQCT.

Results: The average sCa in the TPTx rats pre-dosing at day 1 was 8.3 mg/dL compared to 10.9 mg/dL in the sham operated control rats. The sP values were 8.7 mg/dL and 5.9 mg/dL, respectively. Compound 18 given daily at 1.2 nmol/kg elevated sCa to near-normal levels while lowering sP within a few days of administration. At day 12 (day 5 at steady state with compound 18) sCa had stabilised at normal level (10.7 mg/dL) in this group of animals (compound 18/sham-control ratio=1.01) as opposed to the hypocalceamic level (8.1 mg/dL) measured in the PTH(1-84) treated rats (PTH(1-84)/sham-control ratio=0.76). Additionally, the 24-hour urinary Ca excretion at day 12 was comparable between the animals treated with compound 18 and sham-control. Bone mineral density (BMD) and bone mineral content (BMC) were increased in TPTx controls as seen in HP patients. Treatment with Compound 18 decreased BMD, BMC and area in parallel with an increase in CTx compared to sham and vehicle-treated TPTx animals. A significant increase in trabecular BMD was observed in animals dosed with PTH(1-84) compared to both control groups.

It was concluded that compound 18 at a dosage even as low as less than 20% of the molar equivalent of the here tested dose of PTH(1-84) was able to maintain sCa at a level comparable to the sCa level in sham-control animals (here representing normal level) over a 24 hour period. In contrast, PTH(1-84) at a dose of 7.3 nmol/kg/d did not lead to increase in sCa as compared to the levels in the vehicle-injected TPTx rats. However, a minimal decrease in sP was observed in the PTH(1-84) dosed animals confirming exposure and response to PTH(1-84) in the rats. Following the 28-days of treatment with compound 18, trabecular and cortical BMD in vertebrae were within normal range, whereas an anabolic effect was observed for PTH(1-84) on trabecular and cortical bone in vertebrae.

Example 29

Synthesis of Linker Reagent 29h

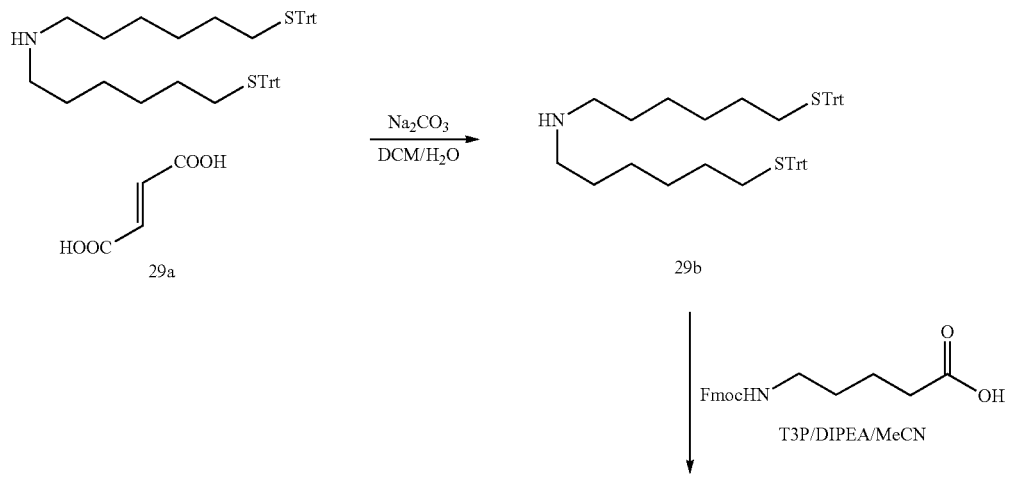

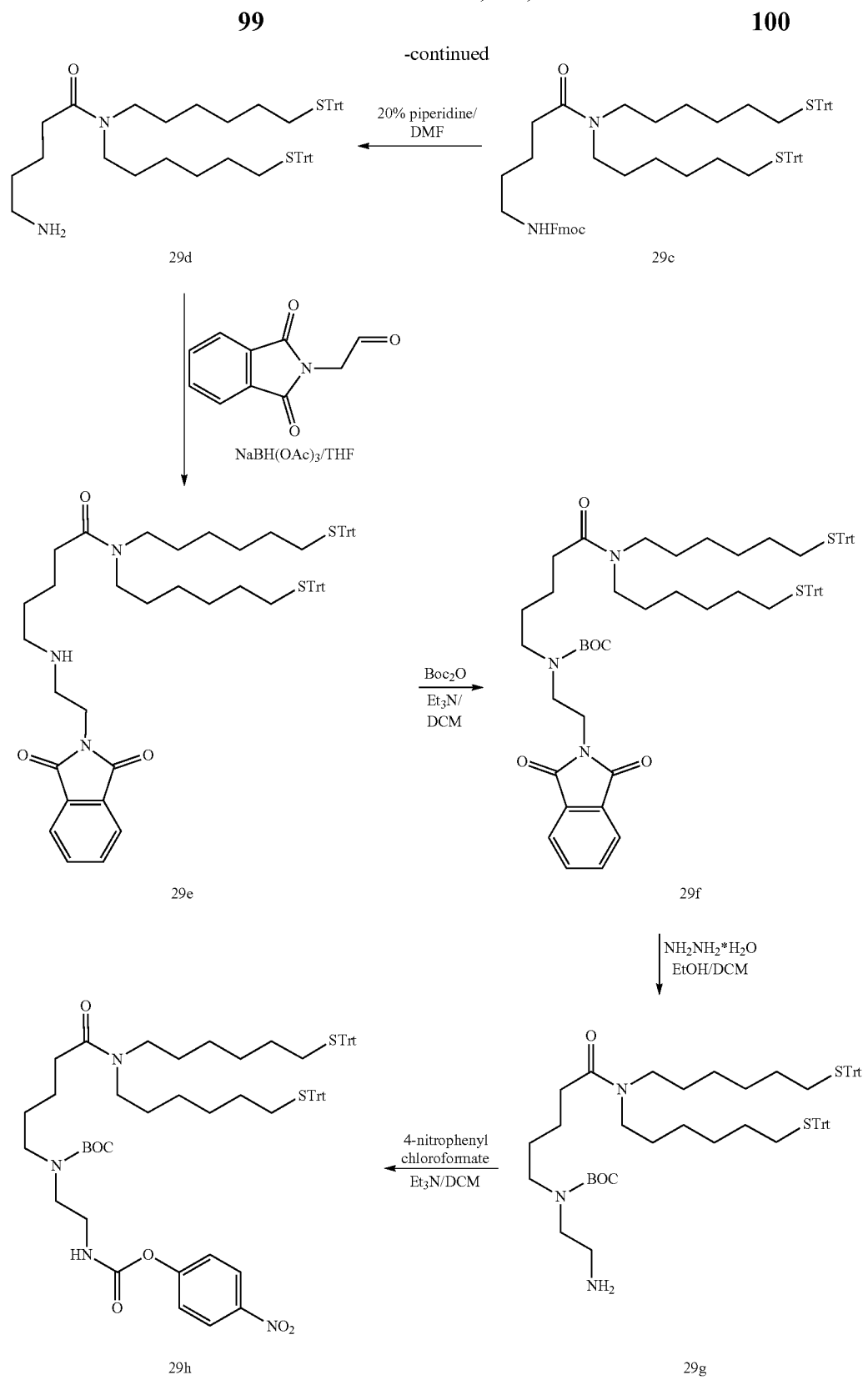

To a solution of compound 29a (250 g, 294 mmol, 1 eq) in dichloromethane (1 L) was added a solution of Na$_2$CO$_3$ (187 g, 1.8 mol, 6 eq) in H$_2$O (1 L). The reaction solution was stirred at 15-30° C. for 0.5 hour. TLC (DCM/MeOH=10:1, R$_f$=0.5) showed the starting material was consumed completely. The organic layer was separated and the aqueous phase was extracted with dichloromethane (1 L). The organic layers were combined and washed with brine (800 mL), then dried with anhydrous Na$_2$SO$_4$, filtered and concentrated in vacuum to give compound 29b as a yellow oil.

Yield: 200 g, 272 mmol, 93%

Four reactions were carried out in parallel.

To a solution of compound 29b (50 g, 68.1 mmol, 1 eq) and Fmoc-5-aminovaleric acid (25.4 g, 74.9 mmol, 1.1 eq), DIPEA (61.6 g, 477 mmol, 83.3 mL, 7 eq) in acetonitrile (500 mL) was added drop-wise T3P 50% [EtOAc] (130 g, 204 mmol, 122 mL, 3 eq) at 15-30° C. for 1 hour. After addition, the reaction mixture was stirred at 15-30° C. for 18 hours. TLC (Petroleum ether/Ethyl acetate=1:1, R$_f$=0.5) showed the starting material was consumed completely. The four reactions were combined for workup. The mixture was diluted with water (3 L), then adjusted to pH=3~4 with 0.5 N HCl solution. The mixture was extracted with EtOAc (3 L), then the aqueous phase was extracted with EtOAc (2 L). The organic layers were combined and washed with brine (1 L), then dried with anhydrous Na$_2$SO$_4$, filtered and concentrated in vacuum to give the crude product as yellow oil. The crude product was purified by column chromatography on silica gel with petroleum ether/ethyl acetate to give compound 29c as a yellow solid.

Yield: 220 g, 199 mmol, 73%

Four reactions were carried out in parallel.

To a solution of compound 29c (55 g, 52 mmol, 1 eq) in dichloromethane (275 mL) was added piperidine (47.3 g, 555 mmol, 55 mL, 10.7 eq). The reaction solution was stirred for 3 hours at 15-30° C. TLC (Petroleum ether/Ethyl acetate=1:1, R$_f$=0) showed the starting material was consumed completely. The four reactions were combined and the mixture was diluted with water (800 mL) and dichloromethane (800 L), then adjusted to pH=3~4 with 0.5 N HCl solution. The organic layer was separated and the aqueous phase was extracted with dichloromethane (800 mL). The organic layers were combined and washed with brine (1 L), then dried with anhydrous Na$_2$SO$_4$, filtered and concentrated in vacuum to give the crude product. The crude product was purified by column chromatography on silica gel with DCM/MeOH to give compound 29d as a white solid.

Yield: 140 g, 168 mmol, 81%

Four reactions were carried out in parallel.

To a solution of compound 29d (30 g, 36 mmol, 1 eq) in THF (300 mL) was added (1,3-dioxo-1,3-dihydro-2H-isoindol-2-yl)acetaldehyde (6.8 g, 36 mmol, 1 eq) and NaBH(OAc)$_3$ (15.3 g, 72 mmol, 2 eq) in one portion. After addition, the reaction mixture was stirred at 15-30° C. for 18 hours. TLC (DCM/MeOH=10:1, R$_f$=0.4) showed the starting material was consumed completely. The four reactions were combined and the mixture was diluted with water (2 L) and EtOAc (1.5 L). The organic layer was separated and the aqueous phase was extracted with EtOAc (1 L). The organic layers were combined and washed with brine (1 L), then dried with anhydrous Na$_2$SO$_4$, filtered and concentrated in vacuum to give compound 29e as yellow oil.

Yield: 164 g, crude

Three reactions were carried out in parallel.

To a solution of compound 29e (50 g, 49.7 mmol, 1 eq) in DCM (150 mL) was added Et$_3$N (25.1 g, 248 mmol, 34.4 mL, 5 eq) and Boc$_2$O (21.7 g, 99.4 mmol, 22.8 mL, 2 eq). After addition, the reaction mixture was stirred at 15-30° C. for 12 hours. TLC (Petroleum ether/Ethyl acetate=1:1, R$_f$=0.4) showed the starting material was consumed completely. The three reactions were combined and the mixture was diluted with water (800 mL), then adjusted to pH=3~4 with 0.5 N HCl solution. The organic layer was separated and the aqueous phase was extracted with dichloromethane (800 mL). The organic layers were combined and washed with brine (800 mL), then dried with anhydrous Na$_2$SO$_4$, filtered and concentrated in vacuum to give the crude product. The crude product was purified by column chromatography on silica gel with petroleum ether/ethyl acetate to give compound 29f as yellow solid.

Yield: 80 g, 72.3 mmol, 48.5%

Three reactions were carried out in parallel.

To a solution of compound 29f (25 g, 22.6 mmol, 1 eq) in DCM (125 mL) and EtOH (300 mL) was added NH$_2$NH$_2$·H$_2$O (28.9 g, 565 mmol, 28 mL, 98% purity, 25 eq) in one portion. After addition, the reaction mixture was stirred at 15-30° C. for 18 hours. TLC (Petroleum ether/Ethyl acetate=1:1, R$_f$=0.03) showed the starting material was consumed completely. The three reactions were combined and the mixture was diluted with water (1 L) and dichloromethane (800 mL), then adjusted to pH=3~4 with 0.5 N HCl solution. The organic layer was separated and the aqueous phase was extracted with dichloromethane (500 mL). The organic layers were combined and washed with brine (800 mL), then dried with anhydrous Na$_2$SO$_4$, filtered and concentrated in vacuum to give the crude product. The crude product was purified by column chromatography on silica gel with DCM/MeOH to give compound 29g as yellow oil.

Yield: 45 g, 46.1 mmol, 68%

Four reactions were carried out in parallel.

To a solution of compound 29g (11 g, 11.3 mmol, 1.0 eq) in THF (100 mL) was added Et$_3$N (3.4 g, 33.8 mmol, 4.7 mL, 3.0 eq) and 4-nitrophenyl carbonochloridate (2.5 g, 12.4 mmol, 1.1 eq). After addition, the reaction mixture was stirred at 15-30° C. for 18 hours. TLC (Petroleum ether/Ethyl acetate=1:1, R$_f$=0.4) showed the starting material was consumed completely. The four reactions were combined and the mixture was diluted with water (800 mL) and EtOAc (800 mL), then adjusted to pH=3~4 with 0.5 N HCl solution. The organic layer was separated and the aqueous phase was extracted with EtOAc (500 mL). The organic layers were combined and washed with brine (800 mL), then dried with anhydrous Na$_2$SO$_4$, filtered and concentrated in vacuum to give the crude product. The crude product was purified by column chromatography on silica gel with petroleum ether:ethyl acetate to give 29h as pale yellow sticky oil.

Yield: 29 g, 25.4 mmol, 56%

Example 30

Synthesis of Transient S1 PTH(1-34) Conjugate 30

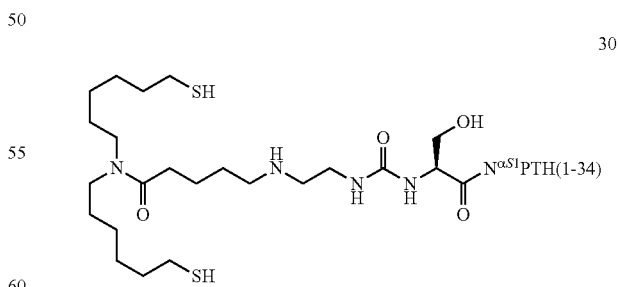

Side chain protected PTH(1-34) on TCP resin having Fmoc protected N-terminus was Fmoc deprotected according to the procedure given in Materials and Methods. A solution of Fmoc-Ser(Trt)-OH (997 mg, 1.75 mmol), PyBOP (911 mg, 1.75 mmol) and DIPEA (305 µL, 1.75 mmol) in DMF (5 mL) was added to 5.0 g (0.58 mmol) of the resin. The suspension was agitated overnight at rt. The resin was washed 10× with DMF and Fmoc-deprotection was performed as described above. A solution of 29h (2.66 g, 2.33 mmol) and DIPEA (611 µL, 3.50 mmol) in DMF (5 mL) was added to the resin. The suspension was agitated overnight at rt. The resin was washed 10× with DMF, 10× with DCM and dried in vacuo. Cleavage of the peptide from the resin and removal of protecting groups was achieved by adding 30 mL cleavage cocktail 100/3/3/2/1 (v/w/v/v/v) TFA/EDT/TES/water/thioanisole and agitating the suspension for 1 h at rt. Crude 30 was precipitated in pre-cooled diethyl ether (−18° C.). The precipitate was dissolved in ACN/water and purified by RP-HPLC. The product fractions were freeze-dried.

Yield: 168 mg (5%), 30*9 TFA

MS: m/z 1155.92=$[M+4H]^{4+}$, (calculated monoisotopic mass for $[M+4H]^{4+}$=1155.85).

Example 31

Synthesis of Transient 4×10 kDa S1 PEG Conjugate 31

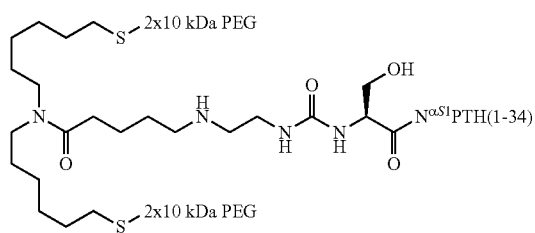

2.3 mL of a solution containing 30 (13 mg/mL, 30 mg, 5.31 µmol) in 8/2 (v/v) water/ethanol containing 0.1% TFA (v/v) and 10 mM methionine were added to 3.4 mL of a solution containing PEG 2×10 kDa maleimide (Sunbright GL2-200MA, 342 mg, 15.9 µmol) in the same solvent. 0.5 M $NaH_2PO_4$ buffer (0.8 mL, pH 7.0) was added and the mixture was stirred for 30 min at rt. 20 µL of TFA was added and the mixture was stored at 4° C. overnight. Conjugate 31 was purified by IEX followed by RP-HPLC using a linear gradient of solvent system A (water containing 0.2% AcOH v/v) and solvent system B (acetonitrile containing 0.2% AcOH v/v).

The product containing fractions were freeze-dried.

Yield: 161 mg (3.55 µmol, 67%) conjugate 31*9 AcOH

Example 32

In Vitro Release Kinetics of Transient 4×10 kDa PEG Conjugate 31

Conjugate 31 (11 mg) was dissolved in 1 vol % acetic acid in water (1.8 mL) at 0.5 mg PTHeq/mL. Buffer exchange to pH 7.4 phosphate buffer (100 mM $NaH_2PO_4$, 10 mM L-methionine, 3 mM EDTA, 0.05% Tween-20, adjusted to pH 7.4 by NaOH) was performed by SEC chromatography. The eluate was further diluted with phosphate buffer to reach a concentration of 0.1 mg PTHeq/mL. The resulting solution was sterile filtered and incubated at 37° C. At time points, aliquots were withdrawn and analysed by RP-HPLC. The fraction of released PTH at a particular time point was calculated from the ratio of UV peak areas of liberated PTH and PEG conjugate. The % released PTH was plotted against incubation time. Curve-fitting software was applied to calculate the corresponding half times of release.

Results:

For conjugate 31 a release half-life time of 14.5 d was obtained.

Example 33

Pharmacodynamic Actions in Cynomolgus Monkeys During a Single Dose PK/PD Study with Compound 18

Compound 18 was administered at 1 µg/kg to male cynomolgus monkeys (N=3) in a single subcutaneous PK/PD study assessing serum calcium (sCa) levels and urinary calcium excretion for 96 hours post-dose.

Results: Following compound 18 administration at 1 µg/kg to cynomolgus monkeys, sCa levels remained within the normal range for 96 hours post-dose and a clear trend for decreased urinary calcium levels over the first 24 hours was observed.

Conclusion: At a dose maintaining sCa in the normocalcemic range, a concurrent decrease in urinary Ca excretion was observed and compound 18 hereby addresses a key unmet medical need in patients with HP.

Example 34

Pharmacokinetic Study of Transient 2×20 kDa S1 PEG Conjugate 18 in Cynomolgus Monkeys Naïve cynomolgus monkeys (2-3.5 years, 2-5 kg) (3-5 males/3-5 females) received daily subcutaneous administrations of 18 at dose levels of 0.2, 0.5 and 1.5 µg PTH/kg. Blood samples were collected at; Day 1: pre-dose, 4 h, 8 h, 12 h, 18 h, and 24 h post-dose, at Day 8: pre-dose, at Day 14: predose, 8h, and 12 h and at Day 28: 3 h, 6 h, 8 h, 12 h, 18 h, 24 h, 72 h, 168 h, and 336 h) and plasma was generated. Total PTH plasma concentrations were determined by quantification of the N-terminal signature peptide (sequence: IQLMHNLGK (SEQ ID NO: 123)) after LysC and GluC digestion as presented earlier in Materials and Methods.

Results: Systemic exposure expressed as $C_{max}$ and AUC increased in an approximately dose proportional manner. Systemic exposure of Total PTH expressed as AUC accumulated approximately 3-fold from Day 1 to Day 28.

A low mean peak-to-trough ratio of Total PTH for all dose groups was observed after daily subcutaneous administration in cynomolgus monkeys at Day 28 (steady state observed from Day 8).

Example 35

Pharmacokinetic Study of Transient 2×20 kDa S1 PEG Conjugate 18 in Sprague-Dawley Rats Sprague-Dawley Crl:CD(SD) rats (initiation of dosing at 8 weeks of age) received daily subcutaneous administrations of 18 at dose levels of 10, 30 and 60 µg PTH/kg for 28 days. A TK group containing of 9 males and 9 females per dose group was divided into 3 subgroups with 3 rats per subgroup. Blood samples were collected up to 28 days with 3 rats per sex, per sampling time point. Samples were collected at Day 1: pre-dose, 4 h, 8 h, 12 h, 18 h, and 24 h post-dose, and at Day 28: 3 h, 6 h, 8 h, 12 h, 18 h, 24 h, and 336 h and plasma was generated. The total PTH plasma concentrations were determined by quantification of the N-terminal signature peptide (sequence: IQLMHNLGK (SEQ ID NO:123)) after LysC and GluC digestion as presented earlier in Materials and Methods.

Results: Systemic exposure expressed as mean $C_{max}$ and AUC increased in an approximately dose proportional manner. Systemic exposure of Total PTH expressed as mean AUC accumulated 3-6 fold from Day 1 to Day 28. Systemic exposure in the female rat was approximately 2-fold higher than in males.

A low mean peak-to-trough ratio of Total PTH for all dose groups was observed after daily subcutaneous administration in Sprague-Dawley rats at Day 28 (steady state observed from Day 8).

Abbreviations

ACN acetonitrile
AcOH acetic acid
Aib 2-aminoisobutyric acid
BMD bone mineral density
Bn benzyl
Boc tert-butyloxycarbonyl
COMU (1-cyano-2-ethoxy-2-oxoethylidenaminooxy)dimethylamino-morpholino-carbenium hexafluorophosphate
cAMP cyclic adenosine monophosphate
d day
DBU 1,3-diazabicyclo[5.4.0]undecene
DCC N,N'-dicyclohexylcarbodiimide
DCM dichloromethane
DIPEA N,N-diisopropylethylamine
DMAP dimethylamino-pyridine
DMF N,N-dimethylformamide
DMSO dimethylsulfoxide
DTT dithiothreitol
EDTA ethylenediaminetetraacetic acid
eq stoichiometric equivalent
ESI-MS electrospray ionization mass spectrometry
Et ethyl
Fmoc 9-fluorenylmethyloxycarbonyl
Glu-C endoproteinase Glu-C
h hour
HATU O-(7-azabenzotriazole-1-yl)-N,N,N',N'-tetramethyluronium hexafluorophosphate
HP hypoparathyroidism
HPLC high performance liquid chromatography
ivDde 4,4-dimethyl-2,6-dioxocyclohex-1-ylidene)-3-methylbutyl
LC liquid chromatography
LTQ linear trap quadrupole
Lys-C endoproteinase Lys-C
LLOQ lower limit of quantification
Mal 3-maleimido propyl
Me methyl
MeOH methanol
min minutes
Mmt monomethoxytrityl
MS mass spectrum/mass spectrometry
m/z mass-to-charge ratio
OtBu tert-butyloxy
PEG poly(ethylene glycol)
pH potentia Hydrogenii
PK pharmacokinetics
Pr propyl
PTH parathyroid hormone
PyBOP benzotriazol-1-yl-oxytripyrrolidinophosphonium hexafluorophosphate
Q-TOF quadrupole time-of-flight
RP-HPLC reversed-phase high performance liquid chromatography
rt room temperature
sCa serum calcium
SIM single ion monitoring
SEC size exclusion chromatography
sc subcutaneous
sP serum phosphate
$t_{1/2}$ half life
TCP tritylchloride polystyrol
TES triethylsilane
TFA trifluoroacetic acid
THF tetrahydrofuran
TK toxicokinetic
Tmob 2,4,6-trimethoxybenzyl
TPTx thyroparathyroidectomy
Trt triphenylmethyl, trityl
ULOQ upper limit of quantification
UPLC ultra performance liquid chromatography
UV ultraviolet
ZQ single quadrupole

---

SEQUENCE LISTING

```
Sequence total quantity: 124
SEQ ID NO: 1            moltype = AA  length = 84
FEATURE                 Location/Qualifiers
source                  1..84
                        mol_type = protein
                        organism = Homo sapiens
SEQUENCE: 1
SVSEIQLMHN LGKHLNSMER VEWLRKKLQD VHNFVALGAP LAPRDAGSQR PRKKEDNVLV  60
ESHEKSLGEA DKADVNVLTK AKSQ                                        84

SEQ ID NO: 2            moltype = AA  length = 83
FEATURE                 Location/Qualifiers
REGION                  1..83
                        note = Human PTH 1-83
source                  1..83
                        mol_type = protein
                        organism = synthetic construct
SEQUENCE: 2
SVSEIQLMHN LGKHLNSMER VEWLRKKLQD VHNFVALGAP LAPRDAGSQR PRKKEDNVLV  60
ESHEKSLGEA DKADVNVLTK AKS                                         83

SEQ ID NO: 3            moltype = AA  length = 82
FEATURE                 Location/Qualifiers
```

```
                            -continued
REGION                  1..82
                        note = human PTH 1-82
source                  1..82
                        mol_type = protein
                        organism = synthetic construct
SEQUENCE: 3
SVSEIQLMHN LGKHLNSMER VEWLRKKLQD VHNFVALGAP LAPRDAGSQR PRKKEDNVLV    60
ESHEKSLGEA DKADVNVLTK AK                                            82

SEQ ID NO: 4            moltype = AA   length = 81
FEATURE                 Location/Qualifiers
REGION                  1..81
                        note = human PTH 1-81
source                  1..81
                        mol_type = protein
                        organism = synthetic construct
SEQUENCE: 4
SVSEIQLMHN LGKHLNSMER VEWLRKKLQD VHNFVALGAP LAPRDAGSQR PRKKEDNVLV    60
ESHEKSLGEA DKADVNVLTK A                                             81

SEQ ID NO: 5            moltype = AA   length = 80
FEATURE                 Location/Qualifiers
REGION                  1..80
                        note = human PTH 1-80
source                  1..80
                        mol_type = protein
                        organism = synthetic construct
SEQUENCE: 5
SVSEIQLMHN LGKHLNSMER VEWLRKKLQD VHNFVALGAP LAPRDAGSQR PRKKEDNVLV    60
ESHEKSLGEA DKADVNVLTK                                               80

SEQ ID NO: 6            moltype = AA   length = 79
FEATURE                 Location/Qualifiers
REGION                  1..79
                        note = human PTH 1-79
source                  1..79
                        mol_type = protein
                        organism = synthetic construct
SEQUENCE: 6
SVSEIQLMHN LGKHLNSMER VEWLRKKLQD VHNFVALGAP LAPRDAGSQR PRKKEDNVLV    60
ESHEKSLGEA DKADVNVLT                                                79

SEQ ID NO: 7            moltype = AA   length = 78
FEATURE                 Location/Qualifiers
REGION                  1..78
                        note = human PTH 1-78
source                  1..78
                        mol_type = protein
                        organism = synthetic construct
SEQUENCE: 7
SVSEIQLMHN LGKHLNSMER VEWLRKKLQD VHNFVALGAP LAPRDAGSQR PRKKEDNVLV    60
ESHEKSLGEA DKADVNVL                                                 78

SEQ ID NO: 8            moltype = AA   length = 77
FEATURE                 Location/Qualifiers
REGION                  1..77
                        note = human PTH 1-77
source                  1..77
                        mol_type = protein
                        organism = synthetic construct
SEQUENCE: 8
SVSEIQLMHN LGKHLNSMER VEWLRKKLQD VHNFVALGAP LAPRDAGSQR PRKKEDNVLV    60
ESHEKSLGEA DKADVNV                                                  77

SEQ ID NO: 9            moltype = AA   length = 76
FEATURE                 Location/Qualifiers
REGION                  1..76
                        note = human PTH 1-76
source                  1..76
                        mol_type = protein
                        organism = synthetic construct
SEQUENCE: 9
SVSEIQLMHN LGKHLNSMER VEWLRKKLQD VHNFVALGAP LAPRDAGSQR PRKKEDNVLV    60
ESHEKSLGEA DKADVN                                                   76

SEQ ID NO: 10           moltype = AA   length = 75
FEATURE                 Location/Qualifiers
REGION                  1..75
                        note = human PTH 1-75
```

```
source                  1..75
                        mol_type = protein
                        organism = synthetic construct
SEQUENCE: 10
SVSEIQLMHN LGKHLNSMER VEWLRKKLQD VHNFVALGAP LAPRDAGSQR PRKKEDNVLV    60
ESHEKSLGEA DKADV                                                    75

SEQ ID NO: 11           moltype = AA  length = 74
FEATURE                 Location/Qualifiers
REGION                  1..74
                        note = human PTH 1-74
source                  1..74
                        mol_type = protein
                        organism = synthetic construct
SEQUENCE: 11
SVSEIQLMHN LGKHLNSMER VEWLRKKLQD VHNFVALGAP LAPRDAGSQR PRKKEDNVLV    60
ESHEKSLGEA DKAD                                                     74

SEQ ID NO: 12           moltype = AA  length = 73
FEATURE                 Location/Qualifiers
REGION                  1..73
                        note = human PTH 1-73
source                  1..73
                        mol_type = protein
                        organism = synthetic construct
SEQUENCE: 12
SVSEIQLMHN LGKHLNSMER VEWLRKKLQD VHNFVALGAP LAPRDAGSQR PRKKEDNVLV    60
ESHEKSLGEA DKA                                                      73

SEQ ID NO: 13           moltype = AA  length = 72
FEATURE                 Location/Qualifiers
REGION                  1..72
                        note = human PTH 1-72
source                  1..72
                        mol_type = protein
                        organism = synthetic construct
SEQUENCE: 13
SVSEIQLMHN LGKHLNSMER VEWLRKKLQD VHNFVALGAP LAPRDAGSQR PRKKEDNVLV    60
ESHEKSLGEA DK                                                       72

SEQ ID NO: 14           moltype = AA  length = 71
FEATURE                 Location/Qualifiers
REGION                  1..71
                        note = human PTH 1-71
source                  1..71
                        mol_type = protein
                        organism = synthetic construct
SEQUENCE: 14
SVSEIQLMHN LGKHLNSMER VEWLRKKLQD VHNFVALGAP LAPRDAGSQR PRKKEDNVLV    60
ESHEKSLGEA D                                                        71

SEQ ID NO: 15           moltype = AA  length = 70
FEATURE                 Location/Qualifiers
REGION                  1..70
                        note = human PTH 1-70
source                  1..70
                        mol_type = protein
                        organism = synthetic construct
SEQUENCE: 15
SVSEIQLMHN LGKHLNSMER VEWLRKKLQD VHNFVALGAP LAPRDAGSQR PRKKEDNVLV    60
ESHEKSLGEA                                                          70

SEQ ID NO: 16           moltype = AA  length = 69
FEATURE                 Location/Qualifiers
REGION                  1..69
                        note = human PTH 1-69
source                  1..69
                        mol_type = protein
                        organism = synthetic construct
SEQUENCE: 16
SVSEIQLMHN LGKHLNSMER VEWLRKKLQD VHNFVALGAP LAPRDAGSQR PRKKEDNVLV    60
ESHEKSLGE                                                           69

SEQ ID NO: 17           moltype = AA  length = 68
FEATURE                 Location/Qualifiers
REGION                  1..68
                        note = human PTH 1-68
source                  1..68
                        mol_type = protein
```

```
                      organism = synthetic construct
SEQUENCE: 17
SVSEIQLMHN LGKHLNSMER VEWLRKKLQD VHNFVALGAP LAPRDAGSQR PRKKEDNVLV    60
ESHEKSLG                                                             68

SEQ ID NO: 18         moltype = AA  length = 67
FEATURE               Location/Qualifiers
REGION                1..67
                      note = human PTH 1-67
source                1..67
                      mol_type = protein
                      organism = synthetic construct
SEQUENCE: 18
SVSEIQLMHN LGKHLNSMER VEWLRKKLQD VHNFVALGAP LAPRDAGSQR PRKKEDNVLV    60
ESHEKSL                                                              67

SEQ ID NO: 19         moltype = AA  length = 66
FEATURE               Location/Qualifiers
REGION                1..66
                      note = human PTH 1-66
source                1..66
                      mol_type = protein
                      organism = synthetic construct
SEQUENCE: 19
SVSEIQLMHN LGKHLNSMER VEWLRKKLQD VHNFVALGAP LAPRDAGSQR PRKKEDNVLV    60
ESHEKS                                                               66

SEQ ID NO: 20         moltype = AA  length = 65
FEATURE               Location/Qualifiers
REGION                1..65
                      note = human PTH 1-65
source                1..65
                      mol_type = protein
                      organism = synthetic construct
SEQUENCE: 20
SVSEIQLMHN LGKHLNSMER VEWLRKKLQD VHNFVALGAP LAPRDAGSQR PRKKEDNVLV    60
ESHEK                                                                65

SEQ ID NO: 21         moltype = AA  length = 64
FEATURE               Location/Qualifiers
REGION                1..64
                      note = human PTH 1-64
source                1..64
                      mol_type = protein
                      organism = synthetic construct
SEQUENCE: 21
SVSEIQLMHN LGKHLNSMER VEWLRKKLQD VHNFVALGAP LAPRDAGSQR PRKKEDNVLV    60
ESHE                                                                 64

SEQ ID NO: 22         moltype = AA  length = 63
FEATURE               Location/Qualifiers
REGION                1..63
                      note = human PTH 1-63
source                1..63
                      mol_type = protein
                      organism = synthetic construct
SEQUENCE: 22
SVSEIQLMHN LGKHLNSMER VEWLRKKLQD VHNFVALGAP LAPRDAGSQR PRKKEDNVLV    60
ESH                                                                  63

SEQ ID NO: 23         moltype = AA  length = 62
FEATURE               Location/Qualifiers
REGION                1..62
                      note = human PTH 1-62
source                1..62
                      mol_type = protein
                      organism = synthetic construct
SEQUENCE: 23
SVSEIQLMHN LGKHLNSMER VEWLRKKLQD VHNFVALGAP LAPRDAGSQR PRKKEDNVLV    60
ES                                                                   62

SEQ ID NO: 24         moltype = AA  length = 61
FEATURE               Location/Qualifiers
REGION                1..61
                      note = human PTH 1-61
source                1..61
                      mol_type = protein
                      organism = synthetic construct
SEQUENCE: 24
```

```
SVSEIQLMHN LGKHLNSMER VEWLRKKLQD VHNFVALGAP LAPRDAGSQR PRKKEDNVLV    60
E                                                                  61

SEQ ID NO: 25           moltype = AA  length = 60
FEATURE                 Location/Qualifiers
REGION                  1..60
                        note = human PTH 1-60
source                  1..60
                        mol_type = protein
                        organism = synthetic construct
SEQUENCE: 25
SVSEIQLMHN LGKHLNSMER VEWLRKKLQD VHNFVALGAP LAPRDAGSQR PRKKEDNVLV    60

SEQ ID NO: 26           moltype = AA  length = 59
FEATURE                 Location/Qualifiers
REGION                  1..59
                        note = human PTH 1-59
source                  1..59
                        mol_type = protein
                        organism = synthetic construct
SEQUENCE: 26
SVSEIQLMHN LGKHLNSMER VEWLRKKLQD VHNFVALGAP LAPRDAGSQR PRKKEDNVL     59

SEQ ID NO: 27           moltype = AA  length = 58
FEATURE                 Location/Qualifiers
REGION                  1..58
                        note = human PTH 1-58
source                  1..58
                        mol_type = protein
                        organism = synthetic construct
SEQUENCE: 27
SVSEIQLMHN LGKHLNSMER VEWLRKKLQD VHNFVALGAP LAPRDAGSQR PRKKEDNV      58

SEQ ID NO: 28           moltype = AA  length = 57
FEATURE                 Location/Qualifiers
REGION                  1..57
                        note = human PTH 1-57
source                  1..57
                        mol_type = protein
                        organism = synthetic construct
SEQUENCE: 28
SVSEIQLMHN LGKHLNSMER VEWLRKKLQD VHNFVALGAP LAPRDAGSQR PRKKEDN       57

SEQ ID NO: 29           moltype = AA  length = 56
FEATURE                 Location/Qualifiers
REGION                  1..56
                        note = human PTH 1-56
source                  1..56
                        mol_type = protein
                        organism = synthetic construct
SEQUENCE: 29
SVSEIQLMHN LGKHLNSMER VEWLRKKLQD VHNFVALGAP LAPRDAGSQR PRKKED        56

SEQ ID NO: 30           moltype = AA  length = 55
FEATURE                 Location/Qualifiers
REGION                  1..55
                        note = human PTH 1-55
source                  1..55
                        mol_type = protein
                        organism = synthetic construct
SEQUENCE: 30
SVSEIQLMHN LGKHLNSMER VEWLRKKLQD VHNFVALGAP LAPRDAGSQR PRKKE         55

SEQ ID NO: 31           moltype = AA  length = 54
FEATURE                 Location/Qualifiers
REGION                  1..54
                        note = human PTH 1-54
source                  1..54
                        mol_type = protein
                        organism = synthetic construct
SEQUENCE: 31
SVSEIQLMHN LGKHLNSMER VEWLRKKLQD VHNFVALGAP LAPRDAGSQR PRKK          54

SEQ ID NO: 32           moltype = AA  length = 53
FEATURE                 Location/Qualifiers
REGION                  1..53
                        note = human PTH 1-53
source                  1..53
                        mol_type = protein
```

```
                                    organism = synthetic construct
SEQUENCE: 32
SVSEIQLMHN LGKHLNSMER VEWLRKKLQD VHNFVALGAP LAPRDAGSQR PRK            53

SEQ ID NO: 33           moltype = AA   length = 52
FEATURE                 Location/Qualifiers
REGION                  1..52
                        note = human PTH 1-52
source                  1..52
                        mol_type = protein
                        organism = synthetic construct
SEQUENCE: 33
SVSEIQLMHN LGKHLNSMER VEWLRKKLQD VHNFVALGAP LAPRDAGSQR PR             52

SEQ ID NO: 34           moltype = AA   length = 51
FEATURE                 Location/Qualifiers
REGION                  1..51
                        note = human PTH 1-51
source                  1..51
                        mol_type = protein
                        organism = synthetic construct
SEQUENCE: 34
SVSEIQLMHN LGKHLNSMER VEWLRKKLQD VHNFVALGAP LAPRDAGSQR P              51

SEQ ID NO: 35           moltype = AA   length = 50
FEATURE                 Location/Qualifiers
REGION                  1..50
                        note = human PTH 1-50
source                  1..50
                        mol_type = protein
                        organism = synthetic construct
SEQUENCE: 35
SVSEIQLMHN LGKHLNSMER VEWLRKKLQD VHNFVALGAP LAPRDAGSQR                50

SEQ ID NO: 36           moltype = AA   length = 49
FEATURE                 Location/Qualifiers
REGION                  1..49
                        note = human PTH 1-49
source                  1..49
                        mol_type = protein
                        organism = synthetic construct
SEQUENCE: 36
SVSEIQLMHN LGKHLNSMER VEWLRKKLQD VHNFVALGAP LAPRDAGSQ                 49

SEQ ID NO: 37           moltype = AA   length = 48
FEATURE                 Location/Qualifiers
REGION                  1..48
                        note = human PTH 1-48
source                  1..48
                        mol_type = protein
                        organism = synthetic construct
SEQUENCE: 37
SVSEIQLMHN LGKHLNSMER VEWLRKKLQD VHNFVALGAP LAPRDAGS                  48

SEQ ID NO: 38           moltype = AA   length = 47
FEATURE                 Location/Qualifiers
REGION                  1..47
                        note = human PTH 1-47
source                  1..47
                        mol_type = protein
                        organism = synthetic construct
SEQUENCE: 38
SVSEIQLMHN LGKHLNSMER VEWLRKKLQD VHNFVALGAP LAPRDAG                   47

SEQ ID NO: 39           moltype = AA   length = 46
FEATURE                 Location/Qualifiers
REGION                  1..46
                        note = human PTH 1-46
source                  1..46
                        mol_type = protein
                        organism = synthetic construct
SEQUENCE: 39
SVSEIQLMHN LGKHLNSMER VEWLRKKLQD VHNFVALGAP LAPRDA                    46

SEQ ID NO: 40           moltype = AA   length = 45
FEATURE                 Location/Qualifiers
REGION                  1..45
                        note = human PTH 1-45
source                  1..45
```

```
                            mol_type = protein
                            organism = synthetic construct
SEQUENCE: 40
SVSEIQLMHN LGKHLNSMER VEWLRKKLQD VHNFVALGAP LAPRD                    45

SEQ ID NO: 41               moltype = AA   length = 44
FEATURE                     Location/Qualifiers
REGION                      1..44
                            note = human PTH 1-44
source                      1..44
                            mol_type = protein
                            organism = synthetic construct
SEQUENCE: 41
SVSEIQLMHN LGKHLNSMER VEWLRKKLQD VHNFVALGAP LAPR                     44

SEQ ID NO: 42               moltype = AA   length = 43
FEATURE                     Location/Qualifiers
REGION                      1..43
                            note = human PTH 1-43
source                      1..43
                            mol_type = protein
                            organism = synthetic construct
SEQUENCE: 42
SVSEIQLMHN LGKHLNSMER VEWLRKKLQD VHNFVALGAP LAP                      43

SEQ ID NO: 43               moltype = AA   length = 42
FEATURE                     Location/Qualifiers
REGION                      1..42
                            note = human PTH 1-42
source                      1..42
                            mol_type = protein
                            organism = synthetic construct
SEQUENCE: 43
SVSEIQLMHN LGKHLNSMER VEWLRKKLQD VHNFVALGAP LA                       42

SEQ ID NO: 44               moltype = AA   length = 41
FEATURE                     Location/Qualifiers
REGION                      1..41
                            note = human PTH-41
source                      1..41
                            mol_type = protein
                            organism = synthetic construct
SEQUENCE: 44
SVSEIQLMHN LGKHLNSMER VEWLRKKLQD VHNFVALGAP L                        41

SEQ ID NO: 45               moltype = AA   length = 40
FEATURE                     Location/Qualifiers
REGION                      1..40
                            note = human PTH 1-40
source                      1..40
                            mol_type = protein
                            organism = synthetic construct
SEQUENCE: 45
SVSEIQLMHN LGKHLNSMER VEWLRKKLQD VHNFVALGAP                          40

SEQ ID NO: 46               moltype = AA   length = 39
FEATURE                     Location/Qualifiers
REGION                      1..39
                            note = human PTH 1-39
source                      1..39
                            mol_type = protein
                            organism = synthetic construct
SEQUENCE: 46
SVSEIQLMHN LGKHLNSMER VEWLRKKLQD VHNFVALGA                           39

SEQ ID NO: 47               moltype = AA   length = 38
FEATURE                     Location/Qualifiers
REGION                      1..38
                            note = human PTH 1-38
source                      1..38
                            mol_type = protein
                            organism = synthetic construct
SEQUENCE: 47
SVSEIQLMHN LGKHLNSMER VEWLRKKLQD VHNFVALG                            38

SEQ ID NO: 48               moltype = AA   length = 37
FEATURE                     Location/Qualifiers
REGION                      1..37
                            note = human PTH 1-37
```

```
                                    -continued
source                   1..37
                         mol_type = protein
                         organism = synthetic construct
SEQUENCE: 48
SVSEIQLMHN LGKHLNSMER VEWLRKKLQD VHNFVAL                              37

SEQ ID NO: 49            moltype = AA   length = 36
FEATURE                  Location/Qualifiers
REGION                   1..36
                         note = human PTH 1-36
source                   1..36
                         mol_type = protein
                         organism = synthetic construct
SEQUENCE: 49
SVSEIQLMHN LGKHLNSMER VEWLRKKLQD VHNFVA                               36

SEQ ID NO: 50            moltype = AA   length = 35
FEATURE                  Location/Qualifiers
REGION                   1..35
                         note = human PTH 1-35
source                   1..35
                         mol_type = protein
                         organism = synthetic construct
SEQUENCE: 50
SVSEIQLMHN LGKHLNSMER VEWLRKKLQD VHNFV                                35

SEQ ID NO: 51            moltype = AA   length = 34
FEATURE                  Location/Qualifiers
REGION                   1..34
                         note = human PTH 1-34
source                   1..34
                         mol_type = protein
                         organism = synthetic construct
SEQUENCE: 51
SVSEIQLMHN LGKHLNSMER VEWLRKKLQD VHNF                                 34

SEQ ID NO: 52            moltype = AA   length = 33
FEATURE                  Location/Qualifiers
REGION                   1..33
                         note = human PTH 1-33
source                   1..33
                         mol_type = protein
                         organism = synthetic construct
SEQUENCE: 52
SVSEIQLMHN LGKHLNSMER VEWLRKKLQD VHN                                  33

SEQ ID NO: 53            moltype = AA   length = 32
FEATURE                  Location/Qualifiers
REGION                   1..32
                         note = human PTH 1-32
source                   1..32
                         mol_type = protein
                         organism = synthetic construct
SEQUENCE: 53
SVSEIQLMHN LGKHLNSMER VEWLRKKLQD VH                                   32

SEQ ID NO: 54            moltype = AA   length = 31
FEATURE                  Location/Qualifiers
REGION                   1..31
                         note = human PTH 1-31
source                   1..31
                         mol_type = protein
                         organism = synthetic construct
SEQUENCE: 54
SVSEIQLMHN LGKHLNSMER VEWLRKKLQD V                                    31

SEQ ID NO: 55            moltype = AA   length = 30
FEATURE                  Location/Qualifiers
REGION                   1..30
                         note = human PTH 1-30
source                   1..30
                         mol_type = protein
                         organism = synthetic construct
SEQUENCE: 55
SVSEIQLMHN LGKHLNSMER VEWLRKKLQD                                      30

SEQ ID NO: 56            moltype = AA   length = 29
FEATURE                  Location/Qualifiers
REGION                   1..29
```

```
SEQ ID NO: 56           moltype = AA  length = 29
FEATURE                 Location/Qualifiers
REGION                  1..29
                        note = human PTH 1-29
source                  1..29
                        mol_type = protein
                        organism = synthetic construct
SEQUENCE: 56
SVSEIQLMHN LGKHLNSMER VEWLRKKLQ                                       29

SEQ ID NO: 57           moltype = AA  length = 28
FEATURE                 Location/Qualifiers
REGION                  1..28
                        note = human PTH 1-28
source                  1..28
                        mol_type = protein
                        organism = synthetic construct
SEQUENCE: 57
SVSEIQLMHN LGKHLNSMER VEWLRKKL                                        28

SEQ ID NO: 58           moltype = AA  length = 27
FEATURE                 Location/Qualifiers
REGION                  1..27
                        note = human PTH 1-27
source                  1..27
                        mol_type = protein
                        organism = synthetic construct
SEQUENCE: 58
SVSEIQLMHN LGKHLNSMER VEWLRKK                                         27

SEQ ID NO: 59           moltype = AA  length = 26
FEATURE                 Location/Qualifiers
REGION                  1..26
                        note = human PTH 1-26
source                  1..26
                        mol_type = protein
                        organism = synthetic construct
SEQUENCE: 59
SVSEIQLMHN LGKHLNSMER VEWLRK                                          26

SEQ ID NO: 60           moltype = AA  length = 25
FEATURE                 Location/Qualifiers
REGION                  1..25
                        note = human PTH 1-25
source                  1..25
                        mol_type = protein
                        organism = synthetic construct
SEQUENCE: 60
SVSEIQLMHN LGKHLNSMER VEWLR                                           25

SEQ ID NO: 61           moltype = AA  length = 84
FEATURE                 Location/Qualifiers
REGION                  1..84
                        note = amidated human PTH 1-84
MOD_RES                 84
                        note = AMIDATION
source                  1..84
                        mol_type = protein
                        organism = synthetic construct
SEQUENCE: 61
SVSEIQLMHN LGKHLNSMER VEWLRKKLQD VHNFVALGAP LAPRDAGSQR PRKKEDNVLV     60
ESHEKSLGEA DKADVNVLTK AKSQ                                            84

SEQ ID NO: 62           moltype = AA  length = 83
FEATURE                 Location/Qualifiers
REGION                  1..83
                        note = amidated human PTH 1-83
MOD_RES                 83
                        note = AMIDATION
source                  1..83
                        mol_type = protein
                        organism = synthetic construct
SEQUENCE: 62
SVSEIQLMHN LGKHLNSMER VEWLRKKLQD VHNFVALGAP LAPRDAGSQR PRKKEDNVLV     60
ESHEKSLGEA DKADVNVLTK AKS                                             83

SEQ ID NO: 63           moltype = AA  length = 82
FEATURE                 Location/Qualifiers
REGION                  1..82
                        note = amidated human PTH 1-82
MOD_RES                 82
                        note = AMIDATION
```

```
source                  1..82
                        mol_type = protein
                        organism = synthetic construct
SEQUENCE: 63
SVSEIQLMHN LGKHLNSMER VEWLRKKLQD VHNFVALGAP LAPRDAGSQR PRKKEDNVLV    60
ESHEKSLGEA DKADVNVLTK AK                                             82

SEQ ID NO: 64           moltype = AA   length = 81
FEATURE                 Location/Qualifiers
REGION                  1..81
                        note = amidated human PTH 1-81
MOD_RES                 81
                        note = AMIDATION
source                  1..81
                        mol_type = protein
                        organism = synthetic construct
SEQUENCE: 64
SVSEIQLMHN LGKHLNSMER VEWLRKKLQD VHNFVALGAP LAPRDAGSQR PRKKEDNVLV    60
ESHEKSLGEA DKADVNVLTK A                                              81

SEQ ID NO: 65           moltype = AA   length = 80
FEATURE                 Location/Qualifiers
REGION                  1..80
                        note = amidated human PTH 1-80
MOD_RES                 80
                        note = AMIDATION
source                  1..80
                        mol_type = protein
                        organism = synthetic construct
SEQUENCE: 65
SVSEIQLMHN LGKHLNSMER VEWLRKKLQD VHNFVALGAP LAPRDAGSQR PRKKEDNVLV    60
ESHEKSLGEA DKADVNVLTK                                                80

SEQ ID NO: 66           moltype = AA   length = 79
FEATURE                 Location/Qualifiers
REGION                  1..79
                        note = amidated human PTH 1-79
MOD_RES                 79
                        note = AMIDATION
source                  1..79
                        mol_type = protein
                        organism = synthetic construct
SEQUENCE: 66
SVSEIQLMHN LGKHLNSMER VEWLRKKLQD VHNFVALGAP LAPRDAGSQR PRKKEDNVLV    60
ESHEKSLGEA DKADVNVLT                                                 79

SEQ ID NO: 67           moltype = AA   length = 78
FEATURE                 Location/Qualifiers
REGION                  1..78
                        note = amidated human PTH 1-78
MOD_RES                 78
                        note = AMIDATION
source                  1..78
                        mol_type = protein
                        organism = synthetic construct
SEQUENCE: 67
SVSEIQLMHN LGKHLNSMER VEWLRKKLQD VHNFVALGAP LAPRDAGSQR PRKKEDNVLV    60
ESHEKSLGEA DKADVNVL                                                  78

SEQ ID NO: 68           moltype = AA   length = 77
FEATURE                 Location/Qualifiers
REGION                  1..77
                        note = amidated human PTH 1-77
MOD_RES                 77
                        note = AMIDATION
source                  1..77
                        mol_type = protein
                        organism = synthetic construct
SEQUENCE: 68
SVSEIQLMHN LGKHLNSMER VEWLRKKLQD VHNFVALGAP LAPRDAGSQR PRKKEDNVLV    60
ESHEKSLGEA DKADVNV                                                   77

SEQ ID NO: 69           moltype = AA   length = 76
FEATURE                 Location/Qualifiers
REGION                  1..76
                        note = amidated human PTH 1-76
MOD_RES                 76
                        note = AMIDATION
source                  1..76
```

```
                              mol_type = protein
                              organism = synthetic construct
SEQUENCE: 69
SVSEIQLMHN LGKHLNSMER VEWLRKKLQD VHNFVALGAP LAPRDAGSQR PRKKEDNVLV    60
ESHEKSLGEA DKADVN                                                    76

SEQ ID NO: 70                 moltype = AA   length = 75
FEATURE                       Location/Qualifiers
REGION                        1..75
                              note = amidated human PTH 1-75
MOD_RES                       75
                              note = AMIDATION
source                        1..75
                              mol_type = protein
                              organism = synthetic construct
SEQUENCE: 70
SVSEIQLMHN LGKHLNSMER VEWLRKKLQD VHNFVALGAP LAPRDAGSQR PRKKEDNVLV    60
ESHEKSLGEA DKADV                                                     75

SEQ ID NO: 71                 moltype = AA   length = 74
FEATURE                       Location/Qualifiers
REGION                        1..74
                              note = amidated human PTH 1-74
MOD_RES                       74
                              note = AMIDATION
source                        1..74
                              mol_type = protein
                              organism = synthetic construct
SEQUENCE: 71
SVSEIQLMHN LGKHLNSMER VEWLRKKLQD VHNFVALGAP LAPRDAGSQR PRKKEDNVLV    60
ESHEKSLGEA DKAD                                                      74

SEQ ID NO: 72                 moltype = AA   length = 73
FEATURE                       Location/Qualifiers
REGION                        1..73
                              note = amidated human PTH 1-73
MOD_RES                       73
                              note = AMIDATION
source                        1..73
                              mol_type = protein
                              organism = synthetic construct
SEQUENCE: 72
SVSEIQLMHN LGKHLNSMER VEWLRKKLQD VHNFVALGAP LAPRDAGSQR PRKKEDNVLV    60
ESHEKSLGEA DKA                                                       73

SEQ ID NO: 73                 moltype = AA   length = 72
FEATURE                       Location/Qualifiers
REGION                        1..72
                              note = amidated human PTH 1-72
MOD_RES                       72
                              note = AMIDATION
source                        1..72
                              mol_type = protein
                              organism = synthetic construct
SEQUENCE: 73
SVSEIQLMHN LGKHLNSMER VEWLRKKLQD VHNFVALGAP LAPRDAGSQR PRKKEDNVLV    60
ESHEKSLGEA DK                                                        72

SEQ ID NO: 74                 moltype = AA   length = 71
FEATURE                       Location/Qualifiers
REGION                        1..71
                              note = amidated human PTH 1-71
MOD_RES                       71
                              note = AMIDATION
source                        1..71
                              mol_type = protein
                              organism = synthetic construct
SEQUENCE: 74
SVSEIQLMHN LGKHLNSMER VEWLRKKLQD VHNFVALGAP LAPRDAGSQR PRKKEDNVLV    60
ESHEKSLGEA D                                                         71

SEQ ID NO: 75                 moltype = AA   length = 70
FEATURE                       Location/Qualifiers
REGION                        1..70
                              note = amidated human PTH 1-70
MOD_RES                       70
                              note = AMIDATION
source                        1..70
                              mol_type = protein
```

```
                              organism = synthetic construct
SEQUENCE: 75
SVSEIQLMHN LGKHLNSMER VEWLRKKLQD VHNFVALGAP LAPRDAGSQR PRKKEDNVLV    60
ESHEKSLGEA                                                          70

SEQ ID NO: 76             moltype = AA  length = 69
FEATURE                   Location/Qualifiers
REGION                    1..69
                          note = amidated human PTH 1-69
MOD_RES                   69
                          note = AMIDATION
source                    1..69
                          mol_type = protein
                          organism = synthetic construct
SEQUENCE: 76
SVSEIQLMHN LGKHLNSMER VEWLRKKLQD VHNFVALGAP LAPRDAGSQR PRKKEDNVLV    60
ESHEKSLGE                                                           69

SEQ ID NO: 77             moltype = AA  length = 68
FEATURE                   Location/Qualifiers
REGION                    1..68
                          note = amidated human PTH 1-68
MOD_RES                   68
                          note = AMIDATION
source                    1..68
                          mol_type = protein
                          organism = synthetic construct
SEQUENCE: 77
SVSEIQLMHN LGKHLNSMER VEWLRKKLQD VHNFVALGAP LAPRDAGSQR PRKKEDNVLV    60
ESHEKSLG                                                            68

SEQ ID NO: 78             moltype = AA  length = 67
FEATURE                   Location/Qualifiers
REGION                    1..67
                          note = amidated human PTH 1-67
MOD_RES                   67
                          note = AMIDATION
source                    1..67
                          mol_type = protein
                          organism = synthetic construct
SEQUENCE: 78
SVSEIQLMHN LGKHLNSMER VEWLRKKLQD VHNFVALGAP LAPRDAGSQR PRKKEDNVLV    60
ESHEKSL                                                             67

SEQ ID NO: 79             moltype = AA  length = 66
FEATURE                   Location/Qualifiers
REGION                    1..66
                          note = amidated human PTH 1-66
MOD_RES                   66
                          note = AMIDATION
source                    1..66
                          mol_type = protein
                          organism = synthetic construct
SEQUENCE: 79
SVSEIQLMHN LGKHLNSMER VEWLRKKLQD VHNFVALGAP LAPRDAGSQR PRKKEDNVLV    60
ESHEKS                                                              66

SEQ ID NO: 80             moltype = AA  length = 65
FEATURE                   Location/Qualifiers
REGION                    1..65
                          note = amidated human PTH 1-65
MOD_RES                   65
                          note = AMIDATION
source                    1..65
                          mol_type = protein
                          organism = synthetic construct
SEQUENCE: 80
SVSEIQLMHN LGKHLNSMER VEWLRKKLQD VHNFVALGAP LAPRDAGSQR PRKKEDNVLV    60
ESHEK                                                               65

SEQ ID NO: 81             moltype = AA  length = 64
FEATURE                   Location/Qualifiers
REGION                    1..64
                          note = amidated human PTH 1-64
MOD_RES                   64
                          note = AMIDATION
source                    1..64
                          mol_type = protein
                          organism = synthetic construct
```

```
SEQUENCE: 81
SVSEIQLMHN LGKHLNSMER VEWLRKKLQD VHNFVALGAP LAPRDAGSQR PRKKEDNVLV    60
ESHE                                                                64

SEQ ID NO: 82           moltype = AA   length = 63
FEATURE                 Location/Qualifiers
REGION                  1..63
                        note = amidated human PTH 1-63
MOD_RES                 63
                        note = AMIDATION
source                  1..63
                        mol_type = protein
                        organism = synthetic construct
SEQUENCE: 82
SVSEIQLMHN LGKHLNSMER VEWLRKKLQD VHNFVALGAP LAPRDAGSQR PRKKEDNVLV    60
ESH                                                                 63

SEQ ID NO: 83           moltype = AA   length = 62
FEATURE                 Location/Qualifiers
REGION                  1..62
                        note = amidated human PTH 1-62
MOD_RES                 62
                        note = AMIDATION
source                  1..62
                        mol_type = protein
                        organism = synthetic construct
SEQUENCE: 83
SVSEIQLMHN LGKHLNSMER VEWLRKKLQD VHNFVALGAP LAPRDAGSQR PRKKEDNVLV    60
ES                                                                  62

SEQ ID NO: 84           moltype = AA   length = 61
FEATURE                 Location/Qualifiers
REGION                  1..61
                        note = amidated human PTH 1-61
MOD_RES                 61
                        note = AMIDATION
source                  1..61
                        mol_type = protein
                        organism = synthetic construct
SEQUENCE: 84
SVSEIQLMHN LGKHLNSMER VEWLRKKLQD VHNFVALGAP LAPRDAGSQR PRKKEDNVLV    60
E                                                                   61

SEQ ID NO: 85           moltype = AA   length = 60
FEATURE                 Location/Qualifiers
REGION                  1..60
                        note = amidated human PTH 1-60
MOD_RES                 60
                        note = ACETYLATION
source                  1..60
                        mol_type = protein
                        organism = synthetic construct
SEQUENCE: 85
SVSEIQLMHN LGKHLNSMER VEWLRKKLQD VHNFVALGAP LAPRDAGSQR PRKKEDNVLV    60

SEQ ID NO: 86           moltype = AA   length = 59
FEATURE                 Location/Qualifiers
REGION                  1..59
                        note = amidated human PTH 1-59
MOD_RES                 59
                        note = AMIDATION
source                  1..59
                        mol_type = protein
                        organism = synthetic construct
SEQUENCE: 86
SVSEIQLMHN LGKHLNSMER VEWLRKKLQD VHNFVALGAP LAPRDAGSQR PRKKEDNVL     59

SEQ ID NO: 87           moltype = AA   length = 58
FEATURE                 Location/Qualifiers
REGION                  1..58
                        note = amidated human PTH 1-58
MOD_RES                 58
                        note = AMIDATION
source                  1..58
                        mol_type = protein
                        organism = synthetic construct
SEQUENCE: 87
SVSEIQLMHN LGKHLNSMER VEWLRKKLQD VHNFVALGAP LAPRDAGSQR PRKKEDNV      58
```

```
SEQ ID NO: 88            moltype = AA   length = 57
FEATURE                  Location/Qualifiers
REGION                   1..57
                         note = amidated human PTH 1-57
MOD_RES                  57
                         note = AMIDATION
source                   1..57
                         mol_type = protein
                         organism = synthetic construct
SEQUENCE: 88
SVSEIQLMHN LGKHLNSMER VEWLRKKLQD VHNFVALGAP LAPRDAGSQR PRKKEDN      57

SEQ ID NO: 89            moltype = AA   length = 56
FEATURE                  Location/Qualifiers
REGION                   1..56
                         note = amidated human PTH 1-56
MOD_RES                  56
                         note = AMIDATION
source                   1..56
                         mol_type = protein
                         organism = synthetic construct
SEQUENCE: 89
SVSEIQLMHN LGKHLNSMER VEWLRKKLQD VHNFVALGAP LAPRDAGSQR PRKKED       56

SEQ ID NO: 90            moltype = AA   length = 55
FEATURE                  Location/Qualifiers
REGION                   1..55
                         note = amidated human PTH 1-55
MOD_RES                  55
                         note = AMIDATION
source                   1..55
                         mol_type = protein
                         organism = synthetic construct
SEQUENCE: 90
SVSEIQLMHN LGKHLNSMER VEWLRKKLQD VHNFVALGAP LAPRDAGSQR PRKKE        55

SEQ ID NO: 91            moltype = AA   length = 54
FEATURE                  Location/Qualifiers
REGION                   1..54
                         note = amidated human PTH 1-54
MOD_RES                  54
                         note = AMIDATION
source                   1..54
                         mol_type = protein
                         organism = synthetic construct
SEQUENCE: 91
SVSEIQLMHN LGKHLNSMER VEWLRKKLQD VHNFVALGAP LAPRDAGSQR PRKK         54

SEQ ID NO: 92            moltype = AA   length = 53
FEATURE                  Location/Qualifiers
REGION                   1..53
                         note = amidated human PTH 1-53
MOD_RES                  53
                         note = AMIDATION
source                   1..53
                         mol_type = protein
                         organism = synthetic construct
SEQUENCE: 92
SVSEIQLMHN LGKHLNSMER VEWLRKKLQD VHNFVALGAP LAPRDAGSQR PRK          53

SEQ ID NO: 93            moltype = AA   length = 52
FEATURE                  Location/Qualifiers
REGION                   1..52
                         note = amidated human PTH 1-52
MOD_RES                  52
                         note = AMIDATION
source                   1..52
                         mol_type = protein
                         organism = synthetic construct
SEQUENCE: 93
SVSEIQLMHN LGKHLNSMER VEWLRKKLQD VHNFVALGAP LAPRDAGSQR PR           52

SEQ ID NO: 94            moltype = AA   length = 51
FEATURE                  Location/Qualifiers
REGION                   1..51
                         note = amidated human PTH 1-51
MOD_RES                  51
                         note = AMIDATION
source                   1..51
```

```
                        mol_type = protein
                        organism = synthetic construct
SEQUENCE: 94
SVSEIQLMHN LGKHLNSMER VEWLRKKLQD VHNFVALGAP LAPRDAGSQR P        51

SEQ ID NO: 95           moltype = AA  length = 50
FEATURE                 Location/Qualifiers
REGION                  1..50
                        note = amidated human PTH 1-50
MOD_RES                 50
                        note = AMIDATION
source                  1..50
                        mol_type = protein
                        organism = synthetic construct
SEQUENCE: 95
SVSEIQLMHN LGKHLNSMER VEWLRKKLQD VHNFVALGAP LAPRDAGSQR          50

SEQ ID NO: 96           moltype = AA  length = 49
FEATURE                 Location/Qualifiers
REGION                  1..49
                        note = amidated human PTH 1-49
MOD_RES                 49
                        note = AMIDATION
source                  1..49
                        mol_type = protein
                        organism = synthetic construct
SEQUENCE: 96
SVSEIQLMHN LGKHLNSMER VEWLRKKLQD VHNFVALGAP LAPRDAGSQ           49

SEQ ID NO: 97           moltype = AA  length = 48
FEATURE                 Location/Qualifiers
REGION                  1..48
                        note = amidated human PTH 1-48
MOD_RES                 48
                        note = AMIDATION
source                  1..48
                        mol_type = protein
                        organism = synthetic construct
SEQUENCE: 97
SVSEIQLMHN LGKHLNSMER VEWLRKKLQD VHNFVALGAP LAPRDAGS            48

SEQ ID NO: 98           moltype = AA  length = 47
FEATURE                 Location/Qualifiers
REGION                  1..47
                        note = amidated human PTH 1-47
MOD_RES                 47
                        note = AMIDATION
source                  1..47
                        mol_type = protein
                        organism = synthetic construct
SEQUENCE: 98
SVSEIQLMHN LGKHLNSMER VEWLRKKLQD VHNFVALGAP LAPRDAG             47

SEQ ID NO: 99           moltype = AA  length = 46
FEATURE                 Location/Qualifiers
REGION                  1..46
                        note = amidated human PTH 1-46
MOD_RES                 46
                        note = AMIDATION
source                  1..46
                        mol_type = protein
                        organism = synthetic construct
SEQUENCE: 99
SVSEIQLMHN LGKHLNSMER VEWLRKKLQD VHNFVALGAP LAPRDA              46

SEQ ID NO: 100          moltype = AA  length = 45
FEATURE                 Location/Qualifiers
REGION                  1..45
                        note = amidated human PTH 1-45
MOD_RES                 45
                        note = AMIDATION
source                  1..45
                        mol_type = protein
                        organism = synthetic construct
SEQUENCE: 100
SVSEIQLMHN LGKHLNSMER VEWLRKKLQD VHNFVALGAP LAPRD               45

SEQ ID NO: 101          moltype = AA  length = 44
FEATURE                 Location/Qualifiers
```

```
REGION                   1..44
                         note = amidated human PTH 1-44
MOD_RES                  44
                         note = AMIDATION
source                   1..44
                         mol_type = protein
                         organism = synthetic construct
SEQUENCE: 101
SVSEIQLMHN LGKHLNSMER VEWLRKKLQD VHNFVALGAP LAPR                           44

SEQ ID NO: 102           moltype = AA  length = 43
FEATURE                  Location/Qualifiers
REGION                   1..43
                         note = amidated human PTH 1-43
MOD_RES                  43
                         note = AMIDATION
source                   1..43
                         mol_type = protein
                         organism = synthetic construct
SEQUENCE: 102
SVSEIQLMHN LGKHLNSMER VEWLRKKLQD VHNFVALGAP LAP                            43

SEQ ID NO: 103           moltype = AA  length = 42
FEATURE                  Location/Qualifiers
REGION                   1..42
                         note = amidated human PTH 1-42
MOD_RES                  42
                         note = AMIDATION
source                   1..42
                         mol_type = protein
                         organism = synthetic construct
SEQUENCE: 103
SVSEIQLMHN LGKHLNSMER VEWLRKKLQD VHNFVALGAP LA                             42

SEQ ID NO: 104           moltype = AA  length = 41
FEATURE                  Location/Qualifiers
REGION                   1..41
                         note = amidated human PTH 1-41
MOD_RES                  41
                         note = AMIDATION
source                   1..41
                         mol_type = protein
                         organism = synthetic construct
SEQUENCE: 104
SVSEIQLMHN LGKHLNSMER VEWLRKKLQD VHNFVALGAP L                              41

SEQ ID NO: 105           moltype = AA  length = 40
FEATURE                  Location/Qualifiers
REGION                   1..40
                         note = amidated human PTH 1-40
MOD_RES                  40
                         note = AMIDATION
source                   1..40
                         mol_type = protein
                         organism = synthetic construct
SEQUENCE: 105
SVSEIQLMHN LGKHLNSMER VEWLRKKLQD VHNFVALGAP                                40

SEQ ID NO: 106           moltype = AA  length = 39
FEATURE                  Location/Qualifiers
REGION                   1..39
                         note = amidated human PTH 1-39
MOD_RES                  39
                         note = AMIDATION
source                   1..39
                         mol_type = protein
                         organism = synthetic construct
SEQUENCE: 106
SVSEIQLMHN LGKHLNSMER VEWLRKKLQD VHNFVALGA                                 39

SEQ ID NO: 107           moltype = AA  length = 38
FEATURE                  Location/Qualifiers
REGION                   1..38
                         note = amidated human PTH 1-38
MOD_RES                  38
                         note = AMIDATION
source                   1..38
                         mol_type = protein
                         organism = synthetic construct
```

```
SEQUENCE: 107
SVSEIQLMHN LGKHLNSMER VEWLRKKLQD VHNFVALG                                        38

SEQ ID NO: 108          moltype = AA   length = 37
FEATURE                 Location/Qualifiers
REGION                  1..37
                        note = amidated human PTH 1-37
MOD_RES                 37
                        note = AMIDATION
source                  1..37
                        mol_type = protein
                        organism = synthetic construct
SEQUENCE: 108
SVSEIQLMHN LGKHLNSMER VEWLRKKLQD VHNFVAL                                         37

SEQ ID NO: 109          moltype = AA   length = 36
FEATURE                 Location/Qualifiers
REGION                  1..36
                        note = amidated human PTH 1-36
MOD_RES                 36
                        note = AMIDATION
source                  1..36
                        mol_type = protein
                        organism = synthetic construct
SEQUENCE: 109
SVSEIQLMHN LGKHLNSMER VEWLRKKLQD VHNFVA                                          36

SEQ ID NO: 110          moltype = AA   length = 35
FEATURE                 Location/Qualifiers
REGION                  1..35
                        note = amidated human PTH 1-35
MOD_RES                 35
                        note = AMIDATION
source                  1..35
                        mol_type = protein
                        organism = synthetic construct
SEQUENCE: 110
SVSEIQLMHN LGKHLNSMER VEWLRKKLQD VHNFV                                           35

SEQ ID NO: 111          moltype = AA   length = 34
FEATURE                 Location/Qualifiers
REGION                  1..34
                        note = amidated human PTH 1-34
MOD_RES                 34
                        note = AMIDATION
source                  1..34
                        mol_type = protein
                        organism = synthetic construct
SEQUENCE: 111
SVSEIQLMHN LGKHLNSMER VEWLRKKLQD VHNF                                            34

SEQ ID NO: 112          moltype = AA   length = 33
FEATURE                 Location/Qualifiers
REGION                  1..33
                        note = amidated human PTH 1-33
MOD_RES                 33
                        note = AMIDATION
source                  1..33
                        mol_type = protein
                        organism = synthetic construct
SEQUENCE: 112
SVSEIQLMHN LGKHLNSMER VEWLRKKLQD VHN                                             33

SEQ ID NO: 113          moltype = AA   length = 32
FEATURE                 Location/Qualifiers
REGION                  1..32
                        note = amidated human PTH 1-32
MOD_RES                 32
                        note = AMIDATION
source                  1..32
                        mol_type = protein
                        organism = synthetic construct
SEQUENCE: 113
SVSEIQLMHN LGKHLNSMER VEWLRKKLQD VH                                              32

SEQ ID NO: 114          moltype = AA   length = 31
FEATURE                 Location/Qualifiers
REGION                  1..31
                        note = amidated human PTH 1-31
```

```
MOD_RES                31
                       note = AMIDATION
source                 1..31
                       mol_type = protein
                       organism = synthetic construct
SEQUENCE: 114
SVSEIQLMHN LGKHLNSMER VEWLRKKLQD V                                              31

SEQ ID NO: 115         moltype = AA  length = 30
FEATURE                Location/Qualifiers
REGION                 1..30
                       note = amidated human PTH 1-30
MOD_RES                30
                       note = AMIDATION
source                 1..30
                       mol_type = protein
                       organism = synthetic construct
SEQUENCE: 115
SVSEIQLMHN LGKHLNSMER VEWLRKKLQD                                                30

SEQ ID NO: 116         moltype = AA  length = 29
FEATURE                Location/Qualifiers
REGION                 1..29
                       note = amidated human PTH 1-29
MOD_RES                29
                       note = AMIDATION
source                 1..29
                       mol_type = protein
                       organism = synthetic construct
SEQUENCE: 116
SVSEIQLMHN LGKHLNSMER VEWLRKKLQ                                                 29

SEQ ID NO: 117         moltype = AA  length = 28
FEATURE                Location/Qualifiers
REGION                 1..28
                       note = amidated human PTH 1-28
MOD_RES                28
                       note = AMIDATION
source                 1..28
                       mol_type = protein
                       organism = synthetic construct
SEQUENCE: 117
SVSEIQLMHN LGKHLNSMER VEWLRKKL                                                  28

SEQ ID NO: 118         moltype = AA  length = 27
FEATURE                Location/Qualifiers
REGION                 1..27
                       note = amidated human PTH 1-27
MOD_RES                27
                       note = AMIDATION
source                 1..27
                       mol_type = protein
                       organism = synthetic construct
SEQUENCE: 118
SVSEIQLMHN LGKHLNSMER VEWLRKK                                                   27

SEQ ID NO: 119         moltype = AA  length = 26
FEATURE                Location/Qualifiers
REGION                 1..26
                       note = amidated human PTH 1-26
MOD_RES                26
                       note = AMIDATION
source                 1..26
                       mol_type = protein
                       organism = synthetic construct
SEQUENCE: 119
SVSEIQLMHN LGKHLNSMER VEWLRK                                                    26

SEQ ID NO: 120         moltype = AA  length = 25
FEATURE                Location/Qualifiers
REGION                 1..25
                       note = amidated human PTH 1-25
MOD_RES                25
                       note = AMIDATION
source                 1..25
                       mol_type = protein
                       organism = synthetic construct
SEQUENCE: 120
SVSEIQLMHN LGKHLNSMER VEWLR                                                     25
```

```
SEQ ID NO: 121         moltype = AA  length = 141
FEATURE                Location/Qualifiers
source                 1..141
                       mol_type = protein
                       organism = Homo sapiens
SEQUENCE: 121
AVSEHQLLHD KGKSIQDLRR RFFLHHLIAE IHTAEIRATS EVSPNSKPSP NTKNHPVRFG    60
SDDEGRYLTQ ETNKVETYKE QPLKTPGKKK KGKPGKRKEQ EKKKRRTRSA WLDSGVTGSG   120
LEGDHLSDTS TTSLELDSRR H                                            141

SEQ ID NO: 122         moltype = AA  length = 20
FEATURE                Location/Qualifiers
REGION                 1..20
                       note = Artificial random coil
source                 1..20
                       mol_type = protein
                       organism = synthetic construct
SEQUENCE: 122
GGPGGPGPGG PGGPGPGGPG                                               20

SEQ ID NO: 123         moltype = AA  length = 9
FEATURE                Location/Qualifiers
REGION                 1..9
                       note = Signature peptide used in analysis
source                 1..9
                       mol_type = protein
                       organism = synthetic construct
SEQUENCE: 123
IQLMHNLGK                                                            9

SEQ ID NO: 124         moltype = AA  length = 7
FEATURE                Location/Qualifiers
REGION                 1..7
                       note = Signature peptide used in analysis
source                 1..7
                       mol_type = protein
                       organism = synthetic construct
SEQUENCE: 124
LQDVHNF                                                              7
```

The invention claimed is:

1. A method of treating a patient having hypoparathyroidism comprising administering to the patient a therapeutically effective amount of a compound according to formula 31

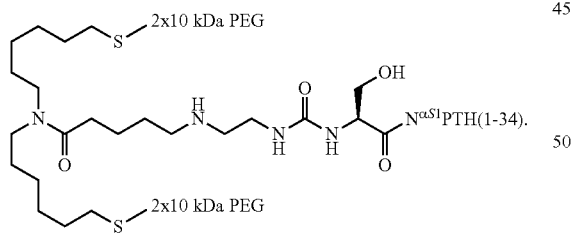

or a pharmaceutically acceptable salt thereof, thereby treating hypoparathyroidism in the patient, wherein PTH(1-34) is parathyroid hormone of the amino acid sequence SEQ ID NO:51, $N^{\alpha S1}$ is the alpha amino group of the N-terminal serine of SEQ ID NO:51 and 2×10 kDa PEG comprises a branched polyethylene glycol polymer of two arms in which each arm has a molecular weight of about 10 kDa and is a moiety of formula (b)

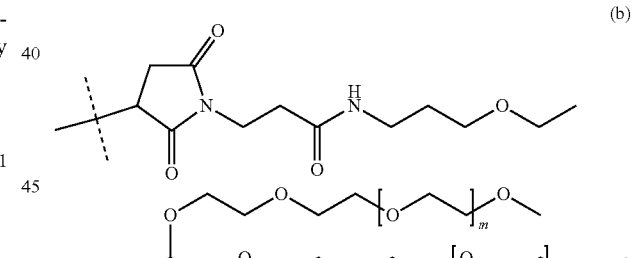

wherein the dashed line indicates attachment to —S— in compound 31, and each of m and p of each moiety is independently an integer.

2. The method of claim 1, wherein the compound or the pharmaceutically acceptable salt thereof is administered to the patient by subcutaneous administration.

3. The method of claim 2, wherein the subcutaneous administration is with a pen injector.

4. The method of claim 2, wherein the subcutaneous administration is with a syringe and needle.

5. The method of claim 1, wherein the compound or the pharmaceutically acceptable salt thereof is administered at intervals of at least 24 hours.

6. The method of claim 1, wherein the compound or the pharmaceutically acceptable salt thereof is administered at intervals of one week.

7. The method of claim 1, wherein the compound 31 is formed by reaction of the compound of formula 30:

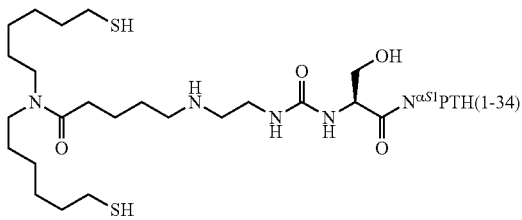

with PEG 2×10 kDa maleimide.

8. A method of parathyroid hormone replacement therapy, comprising administering a compound according to formula 31:

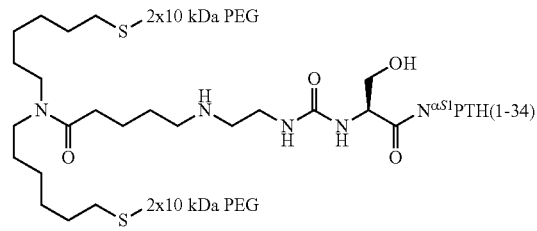

or a pharmaceutically acceptable salt thereof to a patient in need of the therapy, thereby alleviating symptoms relating to hypocalcemia, hypercalciuria, and hyperphosphatemia, without causing hypercalcemia, wherein PTH(1-34) is parathyroid hormone of the amino acid sequence SEQ ID NO:51, $N^{\alpha s1}$ is the alpha amino group of the N-terminal serine of SEQ ID NO:51 and 2×10 kDa PEG comprises a branched polyethylene glycol polymer of two arms in which each arm has a molecular weight of about 10 kDa and is a moiety of formula (b)

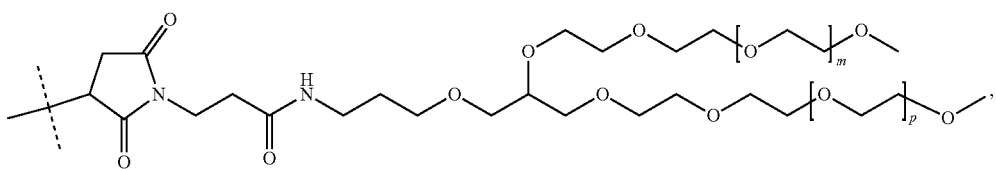

(b)

wherein the dashed line indicates attachment to —S— in compound 31, and each of m and p of each moiety is independently an integer.

9. The method of claim 8, wherein the compound 31 is formed by reaction of the compound of formula 30:

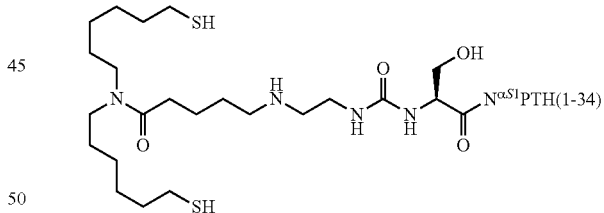

with PEG 2×10 kDa maleimide.

* * * * *

UNITED STATES PATENT AND TRADEMARK OFFICE
CERTIFICATE OF CORRECTION

PATENT NO. : 12,214,020 B2
APPLICATION NO. : 18/464046
DATED : February 4, 2025
INVENTOR(S) : Kennett Sprogøe et al.

Page 1 of 1

It is certified that error appears in the above-identified patent and that said Letters Patent is hereby corrected as shown below:

In the Claims

In Column 141, Lines 44-55, Claim 1, immediately following the structure of compound 31, please delete "." and insert -- , --, therefor.

In Column 144, Line 18, Claim 8, delete "$N^{\alpha s1}$" and insert -- $N^{\alpha S1}$ --, therefor.

Signed and Sealed this
Second Day of September, 2025

Coke Morgan Stewart
*Acting Director of the United States Patent and Trademark Office*